(12) United States Patent
Mumm et al.

(10) Patent No.: US 6,395,966 B1
(45) Date of Patent: *May 28, 2002

(54) FERTILE TRANSGENIC MAIZE PLANTS CONTAINING A GENE ENCODING THE PAT PROTEIN

(75) Inventors: Rita Hogan Mumm, Tolono, IL (US); T. Michael Spencer, Mystic, CT (US)

(73) Assignee: DeKalb Genetics Corp., Dekalb, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/357,497

(22) Filed: Dec. 16, 1994

Related U.S. Application Data

(60) Continuation-in-part of application No. 08/233,067, filed on Apr. 26, 1994, now Pat. No. 5,489,520, and a continuation-in-part of application No. 08/113,561, filed on Aug. 25, 1993, said application No. 08/113,561, is a continuation-in-part of application No. 07/565,844, filed on Aug. 9, 1990, now Pat. No. 5,550,318, said application No. 08/233,067, is a division of application No. 07/565,844.

(51) Int. Cl.⁷ .......................... A01H 5/00; C12N 15/00
(52) U.S. Cl. ................... 800/302; 800/288; 800/265; 800/267; 800/320.1
(58) Field of Search ................... 800/205; 438/172.3, 438/172.1; 47/58

(56) References Cited

U.S. PATENT DOCUMENTS

| | | | |
|---|---|---|---|
| 4,370,160 A | * 1/1983 | Ziemelis | |
| 4,399,216 A | 8/1983 | Axel et al. | 435/6 |
| 4,520,113 A | 5/1985 | Gallo et al. | 436/504 |
| 4,535,060 A | 8/1985 | Comai | 435/172.3 |
| 4,536,475 A | 8/1985 | Anderson | 435/172.3 |
| 4,559,301 A | 12/1985 | Ingolia et al. | 435/172.3 |
| 4,581,847 A | 4/1986 | Hibberd | 47/58 |
| 4,634,665 A | 1/1987 | Axel et al. | 435/68 |
| 4,642,411 A | 2/1987 | Hibberd et al. | 800/1 |
| 4,665,030 A | * 5/1987 | Close | 435/240 |
| 4,666,844 A | * 5/1987 | Cheng | 435/240 |
| 4,683,202 A | 7/1987 | Mullis | 435/91 |
| 4,708,818 A | 11/1987 | Montagnier et al. | 435/5 |
| 4,727,028 A | 2/1988 | Santerre | 435/240.2 |
| 4,743,548 A | 5/1988 | Crossway et al. | 435/172.3 |
| 4,761,373 A | 8/1988 | Anderson et al. | 435/172.3 |
| 4,806,483 A | 2/1989 | Wang | 435/240.49 |
| 4,885,357 A | 12/1989 | Larkins et al. | 530/373 |
| 4,886,878 A | 12/1989 | Larkins et al. | 536/26 |
| 4,940,835 A | * 7/1990 | Shah et al. | 800/205 |
| 4,945,050 A | 7/1990 | Sanford et al. | 435/172.1 |
| 4,956,282 A | 9/1990 | Goodman et al. | 435/69.51 |
| 4,971,908 A | 11/1990 | Kishore et al. | 435/172.1 |
| 5,001,060 A | 3/1991 | Peacock et al. | 435/172.3 |
| 5,004,863 A | 4/1991 | Umbeck | 800/205 |
| 5,013,658 A | * 5/1991 | Dooner et al. | 435/172.3 |
| 5,015,580 A | 5/1991 | Christou et al. | 435/172.3 |
| 5,034,322 A | 7/1991 | Rogers et al. | 435/172.3 |
| 5,036,006 A | 7/1991 | Sanford et al. | 435/170.1 |

(List continued on next page.)

FOREIGN PATENT DOCUMENTS

| | | | |
|---|---|---|---|
| AU | 80893/87 | 12/1988 | |
| CA | 2032443 A1 | 6/1991 | C12N/15/87 |
| DE | 37 38 874 A1 | 11/1988 | A01H/1/06 |
| DE | 40 13 099 A1 | 10/1991 | |
| EP | 0131623 B1 | 1/1984 | |
| EP | 0 126 537 A2 | 11/1984 | A61K/9/52 |
| EP | 0141373 | 5/1985 | |
| EP | 0 142 924 A2 | 5/1985 | C12N/15/00 |
| EP | 0 154 204 A2 | 9/1985 | C12N/15/00 |
| EP | 0160390 | 11/1985 | |
| EP | 0 174 791 A2 | 3/1986 | C12N/15/00 |
| EP | 86400521 | 3/1986 | |
| EP | 0 189 707 A2 | 8/1986 | C12N/15/00 |
| EP | 0193259 | 9/1986 | |
| EP | 0204549 | 10/1986 | |

(List continued on next page.)

OTHER PUBLICATIONS

Christou et al. "Production of trnasgenic rice plants from agronomically important indica and japonica varieties vai electric discharge particle acceleration of exogenous DNA into immature zygotic embryos" Biotechnology pp 957–962, 1991.*

Fromm et al. "Inheritance and expression of chimeric genes in the progeny of transgenic maize plants." Biotechnology vol. 8 pp 833–839, 1990.*

Somers et al. "Fertile, transgenic oat plants." Biotechnology vol. 10. pp 1589–1593, 1992 .*

Kogami et al. Abstract No. 94:499252 Biosis, 1994 .*

Moffat, "Corn Transformed," *Science*, 249:630, Aug. 10, 1990.*

Vasil, "Transgenic Cereals Becoming a Reality," *Bio/Technology*, 8:797, 1990.*

Fromm et al., "Inheritance and Expression of Chimeric Genes in the Progeny of Transgenic Maize Plants," *Bio/Technology*, 8:833–839, 1990.*

Ludwig et al., "Maize R Gene Family: Tissue–Specific Helix–Loop–Helix Proteins," *Cell*, 62:849–851, 1990.*

Potrykus, "Gene Transfer to Cereals: An Assessment," *Bio/Technology*, 8:535–542, Jun. 1990.*

Stanford, "Biolistic Plant Transformation," *Physiol. Plantarum*, 79:206–209, 1990.*

(List continued on next page.)

*Primary Examiner*—Gary Benzion
(74) *Attorney, Agent, or Firm*—Schwegman, Lundberg, Woessner & Kluth, P.A.

(57) ABSTRACT

The present invention provides methods for increasing yield in plants by introducing a gene encoding phosphinothricin acetyltransferase. The invention further involves a method of transferring said increased yield phenotype to other lines of plants by crossing. A maize transformant is identified in which the phosphinothricin acetyltransferase gene integration event is correlated with increased yield.

37 Claims, 11 Drawing Sheets

U.S. PATENT DOCUMENTS

| | | |
|---|---|---|
| 5,049,500 A | 9/1991 | Arnizen et al. ........... 435/172.3 |
| 5,077,399 A | 12/1991 | Brauer et al. .................. 536/27 |
| 5,082,767 A | 1/1992 | Hatfield et al. ................. 435/6 |
| 5,094,945 A | 3/1992 | Comai ..................... 435/172.3 |
| 5,110,732 A | 5/1992 | Benfey et al. ............ 435/172.3 |
| 5,134,074 A | 7/1992 | Gordon et al. ............ 435/240.4 |
| 5,145,777 A | 9/1992 | Goodman et al. ........ 435/172.3 |
| 5,164,310 A | 11/1992 | Smith et al. .............. 435/172.3 |
| 5,177,010 A | 1/1993 | Goldman et al. ......... 435/172.3 |
| 5,187,073 A | 2/1993 | Goldman et al. ......... 435/172.3 |
| 5,187,267 A | 2/1993 | Comai et al. ............... 536/23.1 |
| 5,188,642 A | 2/1993 | Shah et al. ..................... 47/58 |
| 5,188,958 A | 2/1993 | Moloney et al. .......... 435/240.4 |
| 5,196,342 A | 3/1993 | Donovan ................. 435/320.1 |
| 5,215,912 A | 6/1993 | Hoffman .................. 435/240.4 |
| 5,240,841 A | 8/1993 | Johnston et al. .......... 435/172.3 |
| 5,250,515 A | 10/1993 | Fuchs et al. .................. 514/12 |
| 5,254,799 A | 10/1993 | DeGreve et al. ............. 800/205 |
| 5,258,300 A | 11/1993 | Glassman et al. ........ 435/240.4 |
| 5,268,463 A | 12/1993 | Jefferson ..................... 536/23 |
| 5,272,072 A | 12/1993 | Kaneko et al. ............ 435/172.3 |
| 5,273,894 A | 12/1993 | Strauch et al. .............. 435/129 |
| 5,276,268 A | 1/1994 | Strauch et al. .............. 800/205 |
| 5,278,325 A | 1/1994 | Strop et al. .................. 554/12 |
| 5,290,924 A | 3/1994 | Last et al. .................. 536/24.1 |
| 5,302,523 A | 4/1994 | Coffee et al. ............. 435/172.1 |
| 5,310,667 A | 5/1994 | Eichholtz et al. ......... 435/172.3 |
| 5,350,689 A | 9/1994 | Shillito et al. .......... 435/240.47 |
| 5,352,605 A | 10/1994 | Fraley et al. .............. 435/240.4 |
| 5,367,110 A | 11/1994 | Galili et al. ................. 800/205 |
| 5,371,003 A | 12/1994 | Murry et al. .............. 435/172.3 |
| 5,371,015 A | 12/1994 | Sanford et al. .............. 435/287 |
| 5,380,831 A | 1/1995 | Adang et al. ............. 536/23.71 |
| 5,384,253 A | 1/1995 | Krzyzek et al. .......... 435/172.3 |
| 5,405,765 A | 4/1995 | Vasil et al. ................ 435/172.3 |
| 5,422,254 A | 6/1995 | Londesborough et al. ..... 435/97 |
| 5,436,389 A * | 7/1995 | Pfund ......................... 800/200 |
| 5,436,393 A | 7/1995 | Rocha-Sosa et al. ......... 800/205 |
| 5,451,513 A | 9/1995 | Maliga et al. ............. 438/172.3 |
| 5,464,763 A | 11/1995 | Schilperoort et al. ..... 435/172.3 |
| 5,472,869 A | 12/1995 | Krzyzek et al. .......... 435/240.4 |
| 5,484,956 A | 1/1996 | Lundquist et al. ........... 800/205 |
| 5,489,520 A | 2/1996 | Adams et al. ............. 435/172.3 |
| 5,491,288 A | 2/1996 | Chaubet et al. .............. 800/205 |
| 5,495,071 A | 2/1996 | Fischoff et al. .............. 800/205 |
| 5,500,365 A | 3/1996 | Fischoff et al. ........... 435/240.4 |
| 5,508,468 A | 4/1996 | Lundquist et al. ........... 800/205 |
| 5,516,668 A | 5/1996 | Maruta et al. ............. 435/172.3 |
| 5,538,877 A | 7/1996 | Lundquist et al. ........ 435/172.3 |
| 5,538,880 A | 7/1996 | Lundquist et al. ........ 435/172.3 |
| 5,545,545 A | 8/1996 | Gengenbach et al. ..... 435/172.3 |
| 5,550,318 A | 8/1996 | Adams et al. ................ 800/205 |
| 5,554,798 A | 9/1996 | Lundquist et al. ........... 800/205 |
| 5,559,223 A | 9/1996 | Falco et al. ................. 536/23.1 |
| 5,561,236 A | 10/1996 | Leemans et al. ............. 800/205 |
| 5,563,324 A | 10/1996 | Tarczynski et al. .......... 800/205 |
| 5,565,347 A | 10/1996 | Fillatti et al. .............. 435/172.3 |
| 5,567,600 A | 10/1996 | Adang et al. ............. 536/23.71 |
| 5,567,862 A | 10/1996 | Adang et al. ................ 800/205 |
| 5,576,203 A | 11/1996 | Hoffman .................. 435/172.3 |
| 5,578,702 A | 11/1996 | Adang ........................ 530/350 |
| 5,580,716 A | 12/1996 | Johnston et al. ................ 435/5 |
| 5,589,615 A | 12/1996 | De Clercq et al. ........... 800/205 |
| 5,589,616 A | 12/1996 | Hoffman ..................... 800/205 |
| 5,591,616 A | 1/1997 | Hiei et al. ................. 435/172.3 |
| 5,593,963 A | 1/1997 | Van Ooijen et al. .......... 514/12 |
| 5,595,733 A | 1/1997 | Carswell et al. ........... 424/93.21 |
| 5,596,131 A | 1/1997 | Horn et al. .................. 800/205 |
| 5,623,067 A | 4/1997 | Vanderkerchkove et al. .......... 536/24.1 |
| 5,625,136 A | 4/1997 | Koziel et al. ................ 800/205 |
| 5,641,664 A | 6/1997 | D'Halluin et al. ........ 435/172.3 |
| 5,641,876 A | 6/1997 | McElroy et al. ............ 536/24.1 |
| 5,693,507 A | 12/1997 | Daniell et al. ............ 435/172.3 |
| 5,743,477 A | 4/1998 | Walsh et al. ................ 424/94.6 |
| 5,773,691 A | 6/1998 | Falco et al. .................. 800/205 |
| 5,780,708 A | 7/1998 | Lundquist et al. ........... 800/205 |
| 5,780,709 A | 7/1998 | Adams et al. ................ 800/205 |
| 5,886,244 A | 3/1999 | Tomes et al. ................ 800/293 |
| 5,990,387 A | 11/1999 | Tomes et al. ................ 800/293 |
| 5,990,390 A | 11/1999 | Lundquist et al. ........... 800/302 |
| 6,013,863 A | 1/2000 | Lundquist et al. ........... 800/293 |
| 6,020,539 A | 2/2000 | Goldman et al. ............ 800/294 |
| 6,022,846 A | 2/2000 | Van Ooijen et al. ............. 512/5 |
| 6,025,545 A | 2/2000 | Lundquist et al. ........... 800/293 |
| 6,258,999 B1 | 7/2001 | Tomes et al. ............. 800/300.1 |

FOREIGN PATENT DOCUMENTS

| | | | |
|---|---|---|---|
| EP | 0202668 | 11/1986 | |
| EP | 292435 * | 11/1986 | |
| EP | 0242236 | 10/1987 | |
| EP | 242246 * | 10/1987 | |
| EP | 0257472 A2 | 3/1988 | |
| EP | 0262971 | 5/1988 | |
| EP | 0 269 601 A2 | 6/1988 | ........... C12N/15/00 |
| EP | 0270356 | 6/1988 | |
| EP | 0 271 408 A2 | 6/1988 | ........... C12N/15/00 |
| EP | 0 275 069 A2 | 7/1988 | ........... C12N/15/00 |
| EP | 0282164 | 7/1988 | |
| EP | 0280400 | 8/1988 | |
| EP | 0289479 | 11/1988 | |
| EP | 290395 | 11/1988 | |
| EP | 0290395 | 11/1988 | |
| EP | 0 299 552 A1 | 1/1989 | ........... C12N/15/00 |
| EP | 301749 * | 2/1989 | |
| EP | 0353908 A2 | 7/1989 | |
| EP | 0 359 617 | 8/1989 | |
| EP | 0 331 083 A2 | 9/1989 | ........... C12N/15/00 |
| EP | 0331855 | 9/1989 | |
| EP | 0 334 539 A2 | 9/1989 | ........... C12N/15/00 |
| EP | 0 335 528 A2 | 10/1989 | ........... C12N/15/00 |
| EP | 0348348 A2 | 12/1989 | |
| EP | 0385962 A1 | 2/1990 | |
| EP | 0 359 472 A2 | 3/1990 | ........... C12N/15/32 |
| EP | 0360750 A2 | 3/1990 | |
| EP | 0408403 A1 | 5/1990 | |
| EP | 0 420 358 A1 | 4/1991 | ........... C12N/15/55 |
| EP | 0422174 | 4/1991 | |
| EP | 0424047 A1 | 4/1991 | |
| EP | 0459643 A2 | 5/1991 | |
| EP | 0442175 A1 | 8/1991 | |
| EP | 0452269 A2 | 10/1991 | |
| EP | 0 452 269 A2 | 10/1991 | ........... C12N/15/82 |
| EP | 0469273 A1 | 2/1992 | |
| EP | 0 485 970 A3 | 5/1992 | |
| EP | 0 589 110 A1 | 3/1994 | |
| EP | 0 620 281 A2 | 10/1994 | ........... C12N/15/82 |
| FR | 2 661 421 | 10/1991 | |
| GB | 2159173 | 11/1985 | |
| GB | 8810120 | 4/1988 | |
| JP | 61-134343 | 6/1986 | |
| NL | 8801444 | 1/1990 | ........... C12N/15/87 |
| WO | 85/01856 | 5/1985 | ........... A01B/76/00 |
| WO | 85/02972 | 7/1985 | ........... A01C/1/06 |
| WO | WO 85/02973 | 7/1985 | |
| WO | 86/01536 | 3/1986 | ........... C12P/15/00 |
| WO | 86/03776 | 7/1986 | ........... C12N/15/00 |
| WO | 87/04181 | 7/1987 | ........... C12N/1/00 |
| WO | WO 87/05629 | 9/1987 | |
| WO | 88/08034 | 10/1988 | ........... C12P/21/00 |
| WO | WO 89/04371 | 5/1989 | |

| | | | | |
|---|---|---|---|---|
| WO | 89/10396 | 11/1989 | ............ | C12N/5/00 |
| WO | WO89/10396 | 11/1989 | | |
| WO | 89/11789 | 12/1989 | ............ | A01H/1/00 |
| WO | WO 89/12102 | * 12/1989 | | |
| WO | 90/01551 | 2/1990 | ............ | C12N/15/82 |
| WO | 90/01869 | 3/1990 | ............ | A01H/1/04 |
| WO | WO 90/02801 | 3/1990 | | |
| WO | 90/10691 | 9/1990 | ............ | C12N/5/00 |
| WO | WO 90/10725 | 9/1990 | | |
| WO | WO 91/10725 | 9/1990 | | |
| WO | WO 91/02071 | 2/1991 | | |
| WO | 91/04270 | 4/1991 | ............ | C07K/13/00 |
| WO | 91/04323 | 4/1991 | ............ | C12N/9/10 |
| WO | PCT/US91/00183 | 5/1991 | | |
| WO | WO 91/10725 | 7/1991 | | |
| WO | WO 91/16432 | 10/1991 | | |
| WO | WO 92/06205 | 4/1992 | | |
| WO | WO 92/09696 | 6/1992 | | |
| WO | WO 92/12250 | 7/1992 | | |
| WO | 92/14822 | 9/1992 | ............ | C12N/15/29 |
| WO | 92/17580 | 10/1992 | ............ | C12N/5/10 |
| WO | WO 92/19731 | 11/1992 | | |
| WO | 93/06220 | 4/1993 | ............ | C12N/15/82 |
| WO | WO 93/07278 | 4/1993 | | |
| WO | WO 93/08682 | 4/1993 | | |
| WO | WO 93/07278 | 5/1993 | | |
| WO | 93/09237 | 5/1993 | ............ | C12N/15/82 |
| WO | WO/ 9314210 | 7/1993 | ............ | C12N/15/82 |
| WO | WO 93/19190 | 9/1993 | | |
| WO | WO 93/21335 | 10/1993 | ............ | C12N/15/87 |
| WO | 94/08031 | 4/1994 | ............ | C12P/13/22 |
| WO | 94/10315 | 5/1994 | ............ | C12N/15/29 |
| WO | 94/14970 | 7/1994 | ............ | C12N/15/82 |
| WO | 94/20628 | 9/1994 | ............ | C12N/15/82 |
| WO | 94/21805 | 9/1994 | ............ | C12N/15/82 |

OTHER PUBLICATIONS

Cristou et al., "Soybean Genetic Engineering—Commercial Production of Transgenic Plants," *Trends Biotech Techniques*, 8:145–151, 1990.*

Creissen et al., "Agrobacterium—and Microprojectile—Mediated Viral DNA Delivery into Barley Microspore–Derived Cultures," *Plant Cell Reports*, 8:680–683, Apr., 1990.

Tomes et al., "Transgenic Tobacco Plants and Their Progeny Derived by Microprojectile Bombardment of Tobacco Leaves," *Plant Mol Biol.*, 14:261–268, Feb., 1990.

Tomes, "Status Of Corn Transformation." 26th Annual Corn Breeders School, Annual Meeting Proceedings, U. Illinois, Feb. 26–27, 1990, p 7–8.

Ludwig et al., "A Regulatory Gene as a Novel Visible Marker for Maize Transformation," *Science*, 247:449–450, 1990.

Spencer et al.,"Bialaphos Selection of Stable Transformants from Maize Cell Culture," *Theor. Appl. Genet.*, 79:625–631, May, 1990.

Christou et al., "Cotransformation Frequencies of Foreign Genes in Soybean Cell Cultures," *Theor. Appl. Genet.*, 79:337–341, 1990.

White et al., "A Cassette Containing the Bar Gene of *Streptomyces hygroscopicus*: A Selectable Marker for Plant Transformation," *Nucleic Acids Res.*, 18:1062, 1989.

Prioli et al., "Plant Regeneration and Recovery of Fertile Plants from Protoplasts of Maise (*Zea mays* L.)," *Bio/Technology*, 7:589–594, 1989.

Shimamoto et al., "Fertile Transgenic Rico Plants Regenerated from Transformed Protoplasts," *Nature*, 338:274–276, 1989.

Potrykus, "Gene Transfer to Cereals: An Assessment," *Tibtech*, 7:269–273, 1989.

Shillito et al., "Regeneration of Fertile Plants from Protoplasts of Elite Inbred Maize," *Bio/Technology*, 7:581–587, 1989.

Dekeyser et al., "Genetic Transformation of Maize Cells by Particle Bombardment," *Plant Physiol.*, 90:217–223, 1989.

De Greef et al., "Evaluation of Selectable Markers for Rice Transformation," *Bio/Technology*, 7:61–64, 1989.

Kartha et al., "Transient Expression of Chloramphenicol Acetyltransferase (CAT) Gene in Barley Cell Cultures and Immature Embryos through Microprojectile Bombardment," *Plant Cell Reports*, 8:429–432, 1989.

Mendel et al., "Delivery of Foreign Genes to Intact Barley Cells by High–Velocity Microprojectiles," *Theor. Appl. Genet.*, 78:31–34, 1989.

Twell et al., "Transient Expression of Chimeric Genes Delivered into Pollen by Microprojectile Bombardment," *Plant Physiol.*, 91:1270–1274, 1989.

Chandler et al., "Two Regulatory Genes of the Maize Anthocyanin Pathway Are Homologous: Isolation of B Utilizing R Genomic Sequences," *The Plant Cell*, 1:1175–1183, 1989.

Ludwig et al., "Lc, A Member of the Maize R Gene Family Responsible for Tissue–Specific Anthocyanin Production, Encodes a Protein Similar to Transcriptional Activators and Contains the myc–homology Region," *Proc. Natl. Acad. Sci. USA*, 86:7092–7096, 1989.

Klein et al., "Regulation of Anthocyanin Biosynthetic Genes Introduced into Intact Maize Tissued by Microprojectiles," *Proc. Natl. Acad. Sci. USA*, 86:6681–6685, 1989.

Hooykaas, "Transformation of Plant Cells via Agrobacterium," *Plant Mol. Biol.*, 13: 327–336 1989.

Evans, "Somaclonal Variation–Genetic Basis and Breeding Applications," *Trends Genet.*, 5:46–50, 1989.

Klein et al., "Genetic Transformation of Maize Cells by Particle Bombardment," *Plant Physiol.*, 91:440–444, 1989. *Cytodifferentiation During Callus Initiation and Somatic Embryogenesis in Zea Mays L.*, Fransz, P.F., Ph.D. Thesis, U. of Wageningen Press, the Netherlands, 1988.

Rhodes et al., "Genetically Transformed Maize Plants from Protoplasts," *Science*, 240:204–207, 1988.

Ulian et al., "Transformation of Plants via the Shoot Apex," *In Vitro Cellul. & Dev. Biol.*, No. 9:951–954, 1988.

Hauptmann et al., "Evaluation of Selectable Markers for Obtaining Stable Transformants in the Gramineae" *Plant Physiol.*, 86:602–606, 1988.

Klein et al., "Factors Influencing Gene Delivery into *Zea mays* Cells by High Velocity Microprojectiles," *Bio/Technology*, 6:559–563, 1988.

Christou et al., "Stable Transformation of Soybean Callus by DNA–Coated Gold Particles," *Plant Physiol.*, 87:671–674, 1988.

McCabe et al., "Stable Transformation of Soybean (Glycine Max) by Particle Acceleration," *Bio/Technology*, 6:923–926, 1988.

Stanford, "The Biolistic Process," *Trends in Biotechnology*, 6:299–302, 1988.

Wang et al., "Transient Expression of Foreign Genes in Rice, Wheat and Soybean Cells Following Particle Bombardment," *Plant Mol. Biol.*, 11:433–439, 1988.

Klein et al., "Transfer of Foreign Genes into Intact Maize Cells with High–Velocity Microprojectiles" *Proc. Natl. Acad. Sci. USA*, 85:4305–4309, 1988.

Rhodes et al., "Plant Regeneration from Protoplasts Isolated from Embryogenic Maize Cell Cultures," *Bio/Technology*, 6:56–60, 1988.

Smith et al., "Plant Physiology," *Plant Physiology*, (Suppl), 86:108, Abstract 646, 1988.

Gould et al., "Shoot Tip Culture as a Potential Transformation System," Beltwide Cotton Production Research Conferences, Jan. 3–8, 1988, New Orleans, La, Abstract on p 91.

Lutchke et al., "Selection of AUG Initiation Codons Differs in Plants and Animals," *EMBO J.*, 6:43–48, 1987.

Jefferson, "Assaying Chimeric Genes in Plants: The GUS Gene Fusion System," *Plant Mol. Biol. Reporter*, 5:387–405, 1987.

Callis et al., "Introns Increase Gene Expression in Cultured Maize Cells," *Genes & Devel.*, 1:1183–1200, 1987.

Thompson et al., "Characterization of the Herbicide–Resistance Gene Bar from *Streptomyces hygroscopicus*," *EMBO J.*, 6:2519–2523, 1987.

De Block et al., "Engineering Herbicide Resistance in Plants by Expression of a Detoxifying Enzyme," *EMBO J.*, 6:2513–2518, 1987.

Stanford et al., "Delivery of Substance into Cells and Tissue Using Particle Bombardment Process," *Particulate Sci. & Technology*, 5:27–37 1987.

Klein et al., "High–Velocity Microprojectiles for Delivering Nucleic Acids in Living Cells," *Nature*, 327:70–73, 1987.

""Bullets" Transform Plant Cells," News article in *Agricell Report*, Jul., 1987, p 5.

"Shotgunning DNA into Cells" News brief in *Gen. Eng. News*, Jul./Aug., 1987.

Kamo et al., "Establishment and Characterization of Long–Term Embryogenic Maize Callus and Cell Suspension Cultures," *Plant Science*, 45:111–117, 1986.

Vasil et al., "Plant Regeneration from Friable Embryogenic Callus and Cell Suspension Cultures of Aea mays L," *J. Plant Physiol.*, 124:399–408.

Kozak, "Oint Mutations Define a Sequence Flanking the AUG Initiator Codon That Modulates Translation by Eukaryotic Ribosomes," *Cell*, 44:283–292, 1986.

Jefferson et al., "B–Glucuronidase from *Escherichia coli* as a Gene–Fusi Marker" *Proc. Natl. Acad. Sci. USA*, 83:8447–8451, 1986.

Poehlman, *Breeding Field Crops*, Third Edition, AVI Publ. Co., Inc. Westport, CT, 1986, Chapter 18, pp. 469–481.

Murakami et al., "The Bialaphos Biosynthetic Genes of *Streptomyces hygroscopicus*: Molecular Cloning and Characterization of the Gene Cluster," *Mol. Gen. Genet.*, 205:42–50, 1986.

Ludwig et al., "High Frequency Callus Formation from Maize Protoplasts," *Theor. Appl. Genet.*, 71:344–350, 1985.

Odell et al., "Identification of DNA Sequences Required for Activity of the Cauliflower Mosaic Virus 35S Promoter," *Nature*, 313:810–811, 1985.

Ozias–Akins et al., "Progress and Limitations in the Culture of Cereal Protoplasts," *Trends in Biotechnology*, 2:119–123, 1984.

Vasil et al., "Improved Efficiency of Somatic Embryogenesis and Plant Regeneration in Tissue Cultures of Maize (*Zea mays* L.)," *Theor. Appl. Genet.*, 66:285–289, 1983.

Barker et al., "Nucleotide Sequence of the T–DNA Region from the *Agrobacterium tumefaciens* octopine Ti plasmid pTil5955," *Plant Mol. Biol.*, 2:335–350, 1983.

Bevan et al., "A Chimaeric Antibiotic Resistance Gene as a Selectable Marker for Plant Cell Transformation," *Nature*, 304:184–187, 1983.

Bevan et al., "Structure and Transcription of the Nopaline Synthase Gene Region of T–DNA," *Nucl. Acid Res.*, 11:369–385, 1983.

Green et al., "Somatic Cell Genetic Systems in Corn," *Advances in Gene Technology: Molecular Genetics of Plants and Animals*, Academic Press, Inc., 1983, pp 147–157.

Meadows, "Characterization of Cells and Protoplasts of the B73 Maize Cell Line," *Plant Sci. Letters*, 28:337–348, 1982/1983.

Green et al., "Callus Formation from Stem Protoplasts of Corn (*Zea mays* L.)" *Maize for Biological Research*, by Charles Ellis Cohen, a special publication of the Plant Molecular Biology Assoc., 1982, pp 367–372.

Potrykus et al., "Maize for Biological Research," *Theor. Appl. Genet.*, 54:209–214, 1979.

Potrykus et al., "Callus Formation from Cell Protoplasts of Corn (*Zea mays* L.)," *Molec. Gen. Genet.*, 156:347–350, 1977.

Sprague et al., "Corn and Corn Improvement," *Corn and Corn Improvement*, Ed. G.F. Sprague, No. 18 in Agronomy Series, Pub. by American Soc. of Agronomy, Inc, Madison, WI, 1977, pp 305, 320–323.

Green et al., "Plant Regeneration from Tissue Cultures of Maize'" *Crop Science*, 15:417–421, 1975.

Cao et al., "Transformation of Rice and Maize Using the Biolistic Process," *Plant Gene Transfer*, p 21–33, 1990.

Gordon–Kamm et al., "Stable Transformation of Embryogenic Maize Cultures by Microprojectile Bombardment," *Journal of Cellular Biochemistry*, Suppl 13D, Mar. 27—Apr. 7, 1989, p 259, Abstract M122.

Armstrong et al., "Genetic Cytogenetic Variation in Plants Regenerated from Organogenic and Friable, Embryogenic Tissue Cultures Maize," *Biol. Abstracts*, vol. 85, 1988, Abstract 117662.

Ross et al., "Transient and Stable Transgenic Cells and Calli of Tobacco and Maize Following Microprojectile Bombardment," *J. Cell Biochem.*, Suppl. 13D, 1989, Abstract M149.

Gordon–Kamm et al., "Transformation of Maize Cells and Regeneration of Fertile Transgenic Plants," *The Plant Cell*, 2:603–618, 1990.

Robbins–Roth et al., "They Make it Happen in Biotech," *Bioworld*, Nov./Dec., 1990, pp 30–36.

"Genetically Engineered Corn: Breakthrough Brings Market Closer," Market Forecast article in *Genetic Technology News*, Oct. 1990, pp 8 & 11.

Murphy, "New DeKalb–Pfizer Seed Chief to Harvest R & D Breakthroughs," *Crain's Business Weekly*, pp 38–39, 1990.

PCT Search Report, mailed Jan. 15, 1991.

Potrykus, "Gene Transfer to Plants: Assessment and Perspectives," *Physiologia Plantarum*, 79:125–134, 1990.

Lazzeri & Lorz, "In Vitro Genetic manipulation of Cerals and Grasses," *Advances in Cell Culture*, 6:291–325, 1988.

Ahokas, "Transfection of Germinating Barley Seed Electrophoretically with Exogenous DNA," *Theor. Appl. Genet.*, 77:460–472, 1989.

Klein et al., "Genetic Transformation of Maize Cells by Particle Bombardment and the Influence of Methylation on Foreign–Gene Expression," *Gene Manipulation in Plant Improvement II*, Ed. Gustafson, J.P., Plenum Press, New York, 1990, pp. 265–266 only supplied.

Schmidt et al., "Media and Environmental Effects on Phenolics Production from Tobacco Cell Cultures," *Chem. Abstracts*, 110:514–515, Abstract 230156, 1989.

Horn et al., "Transgenic Plants of Orchard Grass," *Chem. Abstracts*, 110:208, Abstract 89869A, 1989.

Crossway et al., "Integration of Foreign DNA Following Microinjection of Tobacco Mesophyll Protoplasts," *Mol. Gen. Genet.*, 202:179–185, 1986.

Jähne et al., "Regeneration of Fertile Plants from Protoplasts Derived from Embryogenic Cell Suspensions of Barley (*Hordeum vulgare* L.)," *Plan Cell Reports*, 10:1–6, 1991.

Ozias–Akins and Vasil, "In Vitro Regeneration and Genetic Manipulation Grasses," *Physiologia Plantarum*, 73:565–569, 1988.

Fromm et al., "Expression of Genes Transferred into Monocot and Dicot Plant Cells by Electroporation," *Proc. Natl. Acad. Sci. USA*, 82:5824–5828, 1985.

Lorz et al., "Advances in Tissue Culture and Progress Towards Genetic Transformation of Cereals," *Plant Breeding*, 100:1, 1988.

Brunke and Meeusen, "Insect Control with Genetically Engineered Crops," *Trends in Biol. Sci.*, 16, 1991.

DeWalk et al., "International Congress on Plant Tissue and Cell Culture, Amsterdam," Abstract A1–36, *7th International Congress on Plant Tissue and Cell Culture*, Amsterdam, Jun. 24–29, 1990.

Ahokes, "Electrophoretic Transfection of Cereal Grains with Exogenous Nucleic Acid," *Soc. Biochem. Biophys. Microbiol. Fenn., Biotieteen Päivät (Bioscience Days)*, Abstracts, Techn Univ of Helsinki, Espoo, p. 2, 1989.

Francois et al., "Chromosomal Location and Nucleotide Sequence of the *Escherichia coli* dapA gene," *Biol. Abstrs.*, 82:(1):AB–391, Abstract 3396.

Graves and Goldman, "The Transformation of *Zea mays* Seedings with *Agrobacterium tumefaciens*," *Plant Mol. Biol.*, 7:43–50, 1986.

*Genetic Technology News*, Mar. 1990.

*Genetic Engineering Letter*, Apr. 1990.

*Genetic Technology News*, May 1990.

*Genetic Technology News*, Jul. 1990.

*Genetic Technology News*, Jul. 1991.

Clark, "Biotech Advance in Corn: Gunslinging Researchers Fire Marker Genes into Corn," *AG Consultant*, Jul. 1990.

Freiberg, "More Researchers Discover Corn Transformation Technology," *AG Biotechnology News*, p. 26.

*Bio/Technology*, p. 490, Jun. 1990.

"Gene Guns Succeed in Altering Corn," *Biotechnology News*, p. 2, Apr. 1990.

Szoka, "Sticky Ends," *Genetic Engineering News*, May 1990.

Nelson, "New Horses for Monocot Gene Jockeys," *The Plant Cell*, 2:589, 1990.

"DeKalb Researchers Produce Fertile Corn Plants with Foreign Genes," *Agri. Newsletter*, Oct./Nov., 1990.

"Ecogen and Evans Biocontrol: The Failure of a "Low–Risk" Strategy" *Agricultural Genetics Report*, Mar./Apr. 1990.

"Food & Agriculture" *Connecticut Academy of Science and Engineering*, 5(4), 1990.

Spencer et al., "Selection of Stable Transformants from Maize Suspension Cultures Using the Herbicide Bialaphos," Poster Presentation, *Faseb Plant Gene Expression Conference*, Copper Mountain, Colorado, Aug. 6–11, 1989.

"Genetic Engineering Advance Announced for Corn Plants," *Investor's Daily*, Apr. 1990.

"Corn Farmers See Economic, Environmental Gold in Designer Genes," *Chicago Tribune*, Jan. 1991.

Steimel, "New Gun will Custom–Design Corn: Breeding Technique Expected by End of '90s Will Let Crop Grow Without Pesticides or Much Water,".

"Genetic Advance May Transform Corn" *Chicago Tribune*, Apr. 1990.

Looker, "DeKalb Claims Success in Effort to Alter Genetic Makeup of Corn," *The Des Moines Register*, Apr. 1990.

"Two Teams Place Genes into Corn," *The Wall Street Journal*, Apr. 1990.

"Corn Breeders Stalk Perfect Hybrid," *Rockford Register Star*, Aug. 1990.

"Cornell U. Gene Gun Hits Biotech Bullseye," *Agriculture Technology*, p. 13.

"Genetic Engineering 'Breakthrough' Disputed," *Cedar Rapids Gazette*, Apr. 1990.

Sanford et al., "Attempted Pollen–Mediated Plant Transformation Employing Genomic Donor DNA," *Theor. Appl. Genet.*, 69:571–574, 1985.

Booy et al., "Attempted Pollen–Mediated Transformation of Maize," *J. Plant Physiol.*, 135:319–324, 1989.

Walbot et al., "Molecular Genetics of Corn," *Ag. Mono.*, 18:389–430, 1988.

McDaniel et al., "Cell–Lineage Patterns in the Shoot Apical Meristem of the Germinating Maize Embryo," *Planta*, 175:13–22, 1988.

Merck Index, 11th ed., pp 405–406, Abstract No. 2795.

*Aldrich Chemical Company Catalogue*, p. 508, 1988.

Freeling et al., "Developmental Potentials of Maize Tissue Cultures," *Maydica*, 21:97–112, 1976.

Chourey et al., "Callus Formation from Protoplasts of a Maize Cell Culture," *Theor. Appl. Genetics*, 59:341–344, 1981.

Guilley et al., "Transcription of Cauliflower Mosaic Virus DNA: Detection of Promoter Sequences, and Characterization of Transcripts," *Cell*, 30:763–773, 1982.

Gritz & Davies, "Plasmid–Encoded Hygromycin B Resistance: The Sequence of Hygromycin B Phosphotransferase Gene and Its Expression in *Escherichia coli* and *Saccharomyces cerevisiae*" *Gene*, 25:179–188, 1983.

de Wet et al., "Cloning of Firefly Luciferase cDNA and the Expression of Active Luciferase in *Escherichia coli*," *Proc. Natl. Acad. Sci. USA*, 82:7870–7873, 1985.

Kamo et al., "Regeneration of *Zea mays* L. from Embryogenic Callus," *Bot. Gaz.*, 146:327–334, 1985.

Richaud et al., "Cromosomal Location and Nucleotide Sequence of the *Escherichia coli* dapA Gene," *J. Bacteriol.*, 166(1):297–300, 1986.

Ampe et al., "The Amino–Acid Sequence of the 2S Sulphur–Rich from Seeds of Brazil nut (*Bertholletia excelsa* H.B.K.)," *Eur. J. Biochem.*, 159:597–604, 1986.

Fromm et al., "Stable Transformation of Maize after Gene Transfer by Electroporation," *Nature*, 319:791–793, 1986.

Pedersen et al., "Sequence Analysis and Characterization of a Maize Gene Encoding a High–Sulfur Zein Protein of $M_r$ 15,000," *J. Biol. Chem.*, 261(14):6279–6284, 1986.

Vasil et al., "Somatic Embryogenesis," *IAPTC Abstracts*, 443, 1986.

Imbrie–Milligan et al., "Microcallus Growth from Maize Protoplasts," *Planta*, 171:58–64, 1987.

Altenbach et al., "Cloning and Sequence Analysis of a cDNA Encoding a Brazil Nut Protein Exceptionally Rich in Methionine," *Plant Mol. Biol.*, 8:239–250, 1987.

Cocking et al., "Gene Transfer in Cereals," *Science*, 236:1259–1262, 1987.

Hoffman et al., "Synthesis and Protein Body Deposition of Maize 15kd Zein in Transgenic Tobacco Seeds," *EMBO J.*, 6:3212–3221, 1987.

Jefferson et al., GUS Fusions: B–glucuronidase as a Sensitive and Versatile Gene Fusion Marker in Higher Plants, *EMBO J.*, 6:3901–3907, 1987.

Hoffman et al., "A Modified Storage Protein is Synthesized, Processed, and Degraded in the Seeds of Transgenic Plants," *Plant Molecular Biology* 11:717–729, 1988.

Kirihara et al., "Isolation and Sequence of a Gene Encoding a Methionine–Rich 10–kDa Zein Protein from Miaze," *Gene*, 71:359–370, 1988.

Kirihara et al., "Differential Expression of a Gene for a Methionine–Rich Storage Protein in Maize," *Mol. Gen. Genet.*, 211:477–484, 1988.

Neuffer, "Growing Maize for Genetic Purposes," *Maize for Biological Research, Plant Mol. Biol. Assoc.*, 1988.

Phillips et al., "Cell/Tissue Culture and In Vitro Manipulation," *Corn and Corn Improvement*, Agronomy Monograph No. 18, Agronomy Society of America et al., 3rd ed., Chapter 5, 1988.

Weising et al., "Foreign Genes In Plants: Transfer, Structure, Expression and Applications," *Ann. Rev. of Genetics*, 22:421–477, 1988.

Altenbach et al., "Enhancement of the Methionine Content of Seed Proteins by the Expression of a Chimeric Gene Encoding a Methionin–Rich Protein in Transgenic Plants," *Plant Mol. Biol.*, 13:513–522, 1989.

Benner et al., "Genetic Analysis of Methionine–Rich Storage Protein Accumulation in Maize," *Theor. Appl. Genet.*, 78:761–767, 1989.

Grimsley et al., "DNA Transfer from Agrobacterium to *Zea mays* or Brassica by Agroinfection is Dependent on Bacterial Virulence Functions," *Molec. Gen. Genet.*, 217:309–316, 1989.

Masumura et al., "cDNA Cloning of an mRNA Encoding of Sulfur–Rich 10 kDa Prolamin Polypeptide in Rice Seeds," *Plant Mol. Biol.*, 12:123–130, 1989.

Rhodes, "Corn: From Protoplasts to Fertile Plants," *Biotechnology*, 7:548, 1989.

Christou et al., "Soybean Genetic Engineering—Commercial Production of Transgenic Plants," *Trends in Biotechnology*, 8:145, 1990.

Okta et al., Gene Manifestation of Exogenous DNA Applied to Self–Propagating Stigma *Jap. J. Breed*, 30 (Suppl. 2) pp 184–185, 1980.

Messing, "Corn Storage Protein: A Molecular Genetic Model," *Division of Energy BioSciences –Summaries of FY 1990 Activities*, Abstract #135, p. 70, 1990.

Morocz et al., "Two Approaches to Rendering *Zea mays* L. Applicable to Tissue Culture Manipulations," IAPTC Conference Proceedings, Abstract 209, p. 190, 1990.

"Chipping Away at Old Weed Enemies," *Farm Science Outlook, Prairie Farmer*, Feb. 20, 1990.

Dialog Search Abstract of a Japanese Patent, No. 61,1324, 343, 1986.

Brill, "Agricultural Microbiology," *Scientific American*, 199–215, 1981.

U.S. Application Serial No. 07/635,279, filed Dec. 28, 1990.

Waldron et al., "Resistance to Hygromycin B," *Plant Mol. Biol.*, 5:103–108, 1985.

Phillips and McClure, "Elevated Protein–Bound Methionine in Seeds of a Maize Line Resistant to Lysine Plus Threonine," *Cereal Chemists*, 62(3):213–218, 1985.

Horn et al., "Transgenic Plants of Orchardgrass (*Dactylis glomerata* L.) from Protoplasts," *Plant Cell Reports*, 7:469–472, 1988.

Lindsey et al., "Electroporation of Cells," *Physiologia Plantarum*, 79: 168–172, 1990.

Patent Family Record for Austalian Patent 87 80 893.

Chasan, "Transforming Maize Transformation," *The Plant Cell*, 4:1463–1464, 1992.

Coe and Neuffer, "The Genetics of Corn" In: *Corn and Corn Improvement* Chapter 4, p. 138, 1977.

D'Halluin et al., "Transgenic Maize Plants by Tissue Electroporation," *The Plant Cell*, 4:1495–1505, 1992.

Koziel et al., "Field Performance of Elite Transgenic Maize Plants Expressing an Insecticidal Protein Derived from Bacillus," *Bio/Technology*, 11:194–200, 1993.

Levitt, "Growth Regulators"In: *Introduction to Plant Physiology*, The C.V. Mosby Company, Saint Louis, publishers, p. 241, 1969.

Ohta, "High–Efficiency Genetic Transformation of Maize by a Mixture of Pollen and Exogenous DNA," *Proc. Natl. Acad. Sci. USA*, 83:715–719, 1986.

Phillips et al., "Cell/Tissue Culture and In Vitro Manipulation" In: *Corn and Corn Improement*, Third Edition, Sprague and Dudley, eds., No. 18 in the series AGROMOMY, Chapter 5, pp. 345–387, 1988.

Robertson, "Loss of Mu Mutator Activity when Active Mu Systems are Transferred to Inbred Lines," *Maize Genetics Cooperation New Letter*, vol. 60, p. 10, 1986.

Sass, "Morphology: Development of the Caryopsis" In: *Corn and Corn Improvement*, 2nd Ed., No. 18 in the series AGROMONY, Chapter 3, p. 98, 1977.

Walters et al., "Transformation and Inheritance of Hygromycin Phosphotransferase Gene in Maize Plants," *Plant Molecular Biology*, 18:189–200, 1992.

Brunke, K.J. and Meeusen, R.L., Insect control with genetically engineered crops, *TIBTECH*, 9:197–200, 1991.

Christou, P., Genetic transformation of crop plants using microprojectile bombardment, *The Plant Journal*, 2:(3)275–281, 1992.

Dupuis, I. and Pace, G.M., Gene transfer to maize male reproductive structure by particle bombardment of tassel primordia, *Plant Cell Reports*, 12:607–611, 1933.

Fitzpatrick, T., Pleiotropic Gene Found In Barley Plant, *Genetic Engineering News*, 13:(5), 1993.

Gould et al., Transformation of *Zea mays* L. Using *Agrobacterium tumefaciens* and the Shoot Apex, *Plant Physiol.*, 95:426–434, 1991.

Gould et al., Transformation of the Graminae by *Agrobacterium tumefaciens, ISPMB*, Abstract #1277, 1991.

Hong et al., Developmental and organ–specific expression of an ABA– and stress–induced protein in barley, *Plant Molecular Biology*, 18:663–1992.

Howe et al., Development of Glyphosate as a Selectable Marker for the Production of Fertile Transfenic Corn Plants, Abstract #P–1136.

Kaeppler et al., Silicon carbice fiber–mediated DNA delivery into plant cells, *Plant Cell Reports*, 9:415–418, 1990.

Langridge et al., Transformation of cereals via Agrobacterium and the pollen pathway: a critical assessment, *The Plant Journal*, 2:(4)631–638, 1992.

Leemans, J., Genetic Engineering For Fertility Control, *Invitro Cellular & Developmental Biology*, 28:(3) Abstract #Y016, 1992.

Laursen et al., Production of fertile transgenic maize by electroporation of suspension culture cells, *Plant Molecular Biology*, 24:51–61, 1994.

Morocz et al., An Improved system to obtain fertile regenerants via maize protoplasles isolated from a highly embryogenic suspension culture, *Theor Appl Genet*, 80:721–726, 1990.

Murry et al., Transgenic Corn Plants Expressing MDMV Strain B Coat Protein are Resistant to Mixed Infections of Maize Dwarf Mosaic Virus and Maize Chlorotic Mottle Virus, *Bio/Technology*, 11:1559–1564, 1993.

Omirulleh et al., Activity of a chimeric promoter with the doubled CaMV 35S enhancer element in protoplast–derived cells and transgenic plants in maize, *Plant Molecular Biology*, 21:415–428, 1993.

Park, S.H. and Smith, R.H., Selection of Maize Transformants from Shoot Apex Cultures Cocultivated with Agrobacterium Containing the Bar Gene, In Vitro, 29A:(3) Abstract #P–1102, 1993.

Rasmussen et al., Biolistic transformation of tobacco and maize suspension cells using bacterial cells as microprojectiles, *Plant Cell Reports*, 13:212–217, 1994.

Sahi et al., Metabolites in Maize Which Affect Virulence Induction in *Agrobacterium tumefaciens, Plant Physiology*, Abstract #514, 1989.

Shen, W. and Hohn, B., Excision of a transposable element from a viral vector introduced into maize plants by agroinfection, *The Plant Journal*, 2:(1)35–42, 1992.

Spencer et al., Segragation of transgenes in maize, *Plant Molecular Biology*, 18:201–210, 1992.

Spencer et al., Fertile Transgenic Maize, *Mid–Atlantic Plant Molecular Biology Society*, p. 30.

Tarczynski et al., Expression of a bacterial mt1D gene in transgenic tobacco leads to production and accumulation of mannitol, *Proc. Natl. Acad. Sci. USA*, 89:2600–2604, 1992.

Tarczynski et al., Stress Protection of Transgenic Tobacco by Production of the Osmolyte Mannitol, *Science*, 259:508–510, 1993.

Vain et al., Osmotic treatment enhances particle bombardment–mediated transient and stable transformation of maize, *Plant Cell Reports*, 12:84–88, 1993.

Wang et al., Characterization of cis–Acting Elements Regulating Transcription from the Promoter of a Constitutively Active Rice Actin Gene, *Molecular and Cellular Biology*, 12:(8)3399–3406, 1992.

Pioneer Hi–Bred International, Inc., Release of Genetically Engineered Corn Plants.

In Vitro Cellular & Developmental Biology, *Journal of the Tissue Culture Association*, 28:(3)ISSN 0883–8364, 1992.

The International Society for Plant Molecular Biology, Program and Abstracts, Molecular Biology of Plant Growth and Development, Tucson, Arizona, Oct. 6–11, 1991.

Ellis et al., "Does the ocs–element occur as a functional component of the promoters of plant genes?" *The Plant Journal*, 4(3):433–443, 1933.

Goff et al., "Transactivation of anthocyanin biosynthetic genes following transfer of B regulatory genes into maize tissues," *The EMBO Journal*, 9(8):2517–2522, 1990.

Green & Rhodes, "Plant Regeneration in Tissue Cultures of Maize," In: *Maize for Biological Research*, William F. Sheridan, Ed., University of North Dakota, Grand Forks, North Dakota, 1982.

Shen & Hohn, "Amplification and expression of the β–glucuronidase gene in maize plants by vectors based on maize streak virus," *The Plant Journal*, 5(2):227–236, 1994.

Wan & Lemaux, "Generation of Large Numbers of Independently Transformed Fertile Barley Plants," *Plant Physiol.*, 104:37–48, 1994.

EPO Notice regarding publication of bibliographic data for EPO 485506.

Casas et al., "Transgenic sorghum plants via microprojectile bombardment," *Proc. Natl. Acad. Sci. USA*, 90:11212–11216, 1993.

Castillo et al., "Rapid Production of Fertile Transgenic Plants of Rye (*Secale cereale* L.)," *Bio/Technology*, 12:1366–1371, 1994.

Christou et al., "Production of Transgenic Rice (*Oryza sativa* L.) Plants from Agronomically Important Indica and Japonica Varieties Via Electric Discharge Particle Acceleration of Exogenous DNA into Immature Zygotic Embryos," *Bio/Technology*, 9:957–962, 1991.

Dröge–Laser et al., "The Metabolites of the Herbicide L–Phosphinothricin (Glufosinate)", *Plant Physiol.*, 105:159–166, 1994.

Frame et al., Production of fertile transgenic maize plants by silicon carbide whisker–mediated transformation, *The Plant Journal*, 6(6):941–948, 1994.

Hartman et al., "Herbicide Resistant Turfgrass (*Agrostis palustris* Huds.) by Biolistic Transformation", *Bio/Technology*, 12:919–923, (1994).

Becker et al., "Regeneration of transgenic, microspore–derived, fertile barley," *Theor Appl Genet*, 89:525–533, 1994.

Weeks et al., Rapid Production of Multiple Independent Lines of Fertile Transgenic Wheat (*Triticum aestivum*), *Plant Physiol.*, 102:1077 1084, 1993.

Beermann et al., "Tyrosinase as a marker for transgenic mice," *Nucleic Acids Research*, 19(4):958, 1991.

Gordon–Kamm et al., "Transformation of Maize Cells and Regeneration of Fertile Transgenic Plants," *The Plant Cell*, 2:603–618, Jul., 1990.

Perl et al., "Bacterial Dihydrodipicolinate Synthase and Desensitized Aspartate Kinase: Two Novel Selectable Markers for Plant Transformation," *Bio/Technology*, 11:715–718, Jun., 1993.

Perlak et al., "Modification of the coding sequence enhances plant expression of insect control protein genes," *Proc. Natl. Acad. Sci. USA*, 88:3324–3328, Apr., 1991.

Spencer et al., "Segregation of transgenes in maize," *Plant Molecular Biology*, 18:201–210, 1992.

Sugiyama et al., "Use of the Tyrosinase Gene from Streptomyces to Probe Promoter Sequences for *Escherichia coli,*" *Plasmid*, 23:237–241, 1990.

Wong et al., "*Arabidopsis thaliana* small subunit leader and transit peptide enhance the expression of *Bacullus thuringiensis* proteins in transgenic plants," *Plant Molecular Biology*, 20:81–93, 1992.

International Search Report dated Aug. 16, 1995.

Botterman and Leemans, "Engineering herbicide resistance in plants," *TIG*, 4(8):219–222, 1988.

Mariani et al., "Engineered male sterility in plants," *Symposia of the Society for Experimental Biology*, pp. 271–279, 1991.

*In Vitro Cellular & Developmental Biology*, 21, Program Issue: Thirty–Sixth Annual Meeting of the Tissue Culture Association, New Orleans, LA, 88 p., (Mar. 1985).

*In Vitro Cellular & Developmental Biology*, 23, Program Issue: Thirty–Eighth Annual Meeting of the Tissue Culture Association, Washington, D.C., 93 p., (Mar. 1987).

*In Vitro Cellular & Development Biology*, 24, Program Issue: Thirty–Ninth Annual Meeting of the Tissue Culture Association, Las Vegas, NV, 92 p., (Mar. 1988).

*In Vitro Cellular & Developmental Biology*, 25, Program Issue: Fortieth Annual Meeting of the Tissue Culture Association, Orlando, Fl, 73 p., (Mar. 1989).

*In Vitro Cellular & Developmental Biology*, 26, Program Issue: Forty–First Annual Meeting of the Tissue Culture Association, Houston, TX, 88 p., (Mar. 1990).

"Ciba–Geigy Joins Maize Transformers",*AGROW*, No. 118, 20, (Aug. 31, 1990).

"European Firm Devises Insect–Resistant Plants", *Agricultural Biotechnology News*, 1, 6, (Mar.–Apr. 1986).

"Molecular Strategies for Crop Improvement", *Journal of Cellular Biochemistry*, Supplement 14e, List of Plenary and Poster Sessions, organized by Arntzen, C., et al., for The Keystone Conference on Molecular Strategies for Crop Plant Improvement, held at the 19th UCLA Symposia, 257, (1990).

"Monsanto, DeKalb Gunning for Insect–, Disease–Resistant Corn", *Biotechnology Newswatch*, 4–5, (May 7, 1990).

"Plant Science Produces Transformed Corn", *Chemical and Engineering News*, 7, (Jan. 29, 1990).

Abbe, E.C., et al., "The Growth of the Shoot Apex in Maize: Embryogeny", *American Journal of Botany*, 41, 285–293, (Apr. 1954).

Adang, M.J., et al., "Expression of a *Bacillus thuringiensis* Insecticidal Crystal Protein Gene in Tobacco Plants", *Molecular Strategies for Crop Protection*, Arntzen, C.J., et al. (eds.), Alan R. Liss, Inc., New York, 345–353, (1987).

Anderson, P.C., et al., "Herbicide–Tolerant Mutants of Corn", *Genome*, 31, 994–999, (1989).

Angus, T.A., "Implications of Some Recent Studies of *Bacillus thuringiensis* —A Personal Purview", *Proceedings of the 4th International Colloquium on Insect Pathology*, College Park, MD, 183–189, (Aug. 25–28, 1970).

Armaleo, D., et al., "Biolistic Nuclear Transformation of *Saccharomyces cerevisiae* and Other Fungi", *Curr. Genet.*, 17, 97–103, (1990).

Armstrong, C.L., et al., "Development and Availability of Germplasm with High Type II Culture Formation Response", *Maize Genetics Cooperation Newsletter*, 65, 92–93, (Mar. 1, 1991).

Aronson, A.I., et al., "*Bacillus thuringiensis* and Related Insect Pathogens", *Microbiological Reviews*, 50, 1–24, (Mar. 1986).

Aronson, J.N., et al., "Toxic Trypsin Digest Fragment from the *Bacillus thuringiensis* Parasporal Protein", *Applied and Environmental Microbiology*, 53, 416–421, (Feb. 1987).

Bartels, D., et al., "An ABA and GA Modulated Gene Expressed in the Barley Embryo Encodes an Aldose Reductase Related Protein", *EMBO Journal*, 10, 1037–1043, (May 1991).

Barton, K.A., et al., "*Bacillus thuringiensis* δ–Endotoxin Expressed in Transgenic *Nicotiana tabacum* Provides Resistance to Lepidopteran Insects", *Plant Physiol.*, 85, 1103–1109, (1987).

Barton, K.A., et al., "Production of *Bacillus thuringiensis* Insecticidal Proteins in Plants", *Transgenic Plants*, vol. 1, Kung, S.–D., et al., (eds.), Academic Press, Inc., San Diego, CA, 297–315, (1993).

Birk, Y., et al., "Separation of a Tribolium–Protease Inhibitor from Soybeans on a Calcium Phosphate Column", *Biochem. Biophys. Acta*, 67, 326–328, (Feb. 12, 1963).

Bishop, D.H., et al., "Genetically Engineered Viral Insecticides—A Progress Report 1986–1989", *Pestic. Sci.*, 27, 173–189, (1989).

Boylan–Pett, W., et al., "Effectiveness of *Bacillus thuringiensis*–Transgenic Potato Plants for Control of Colorado Potato Beetles, 1991", *Insecticide & Acaricide Tests*: 1992, 17, 124–125, (1992).

Boynton, J.E., et al., "Chloroplast Transformation in Chlamydomonas with High Velocity Microprojectiles", *Science*, 240, 1534–1537, (Jun. 10, 1988).

Bryant, J.A., "At Last: Transgenic Cereal Plants from Genetically Engineered Protoplasts", *Trends in Biotechnology*, 6, 291–292, (Dec. 1988).

Burgerjon, A., et al., "Industrial and International Standardization of Microbial Pesticides—I. *Bacillus thuringiensis*", *Entomophaga*, 22, 121–129, (1977).

Busvine, J.R., *A Critical Review of the Techniques for Testing Insecticides*, Table of Contents, Commonwealth Agricultural Bureaus, Slough, England, iii–xi, (1971).

Bytebier, B., et al., "T–DNA Organization in Tumor Cultures and Transgenic Plants of the Monocotyledon *Asparagus officinalis*", *Proc. Natl. Acad. Sci. USA*, 84, 5345–5349, (Aug. 1987).

Calabrese, D.M., et al., "A Comparison of Protein Crystal Subunit Sized in *Bacillus thuringiensis*", *Canadian Journal of Microbiology*, 26, 1006–1010, (Aug. 1980).

Caplan, A., et al., "Introduction of Genetic Material into Plant Cells", *Science*, 222, 815–821, (Nov. 18, 1983).

Carozzi, N.B., et al., "Expression of a Chimeric CaMV 35S *Bacillus thuringiensis* Insecticidal Protein Gene in Transgenic Tobacco",*Plant Molecular Biology*, 20, 539–548, (1992).

Chaleff, R.S., "Induction, Maintenance, and Differentiation of Rice Callus Cultures on Ammonium as Sole Nitrogen Source", *Plant Cell Tissue Organ Culture*, 2, 29–37, (1983).

Christou, P., et al., "Inheritance and Expression of Foreign Genes in Transgenic Soybean Plants", *Proc. Natl. Acad. Sci. USA*, 86, 7500–7504, (Oct. 1989).

Cooksey, K.E., "Purification of a Protein from *Bacillus thuringiensis* Toxic to Larvae of Lepidoptera", *Biochem. J.*, 106, 445–454, (1968).

De Block, M., et al., "Expression of Foreign Genes in Regenerated Plants and Their Progeny", *EMBO J.*, 3, 1681–1689, (1984).

De Block, M., et al., "The Use of Phosphinothricin Resistance as a Selectable Marker in Tobacco Protoplast Transformation", In: *Progress in Plant Protoplast Research*, Proceedings of the 7th International Protoplast Symposium, Wageningen, The Netherlands, Puite, K.J., et al., (eds.), Kluwer Academic Publishers, Dordrecht, The Neterlands, 389–390, (Dec. 6–11, 1987).

Denecke, J., et al., "Quantification of Transient Expression Levels of Genes Transferred to Plant Protoplasts by Electroporation", *Progress in Plant Protoplast Research*, Puite, K.J., (eds.), Proceedings of the 7th International Protoplast Symposium, Wageningen, The Netherlands, 337–338, (Dec. 6–11, 1987).

Denholm, I., et al., "Tactics for Managing Pesticide Resistance in Arthropods: Theory and Practice", *Annu. Rev. Entomol.*, 37, 91–112, (1992).

Di, R., et al., "Transformation of Soybean with Bean Pod Mottle Virus Coat Proteins–Precursor Gene using the Biolistic Method", *Phytopathology*, 83, Abstract No. A394, p. 1374, (Dec. 1993).

Duncan, D.R., et al., "The Production of Callus Capable of Plant Regeneration for Immature Embryos of Numerous *Zea mays* Genotpyes", *Planta*, 165, 322–332, (1985).

Dunder, E., et al., "High Frequency Transformation of Maize by Microprojectile Bombardment of Immature Embryos", *Abstracts, 35 Annual Maize Genetics Conference*, St. Charles, IL, Poster No. 16, p. 30 (Mar. 18–21, 1993).

Dunder, E., et al., "Transgenic Anthocyanin Color Phenotypes Produced in Callus, Plants and Progeny of Maize", *Abstracts, 35th Annual Maize Genetics Conference*, St. Charles, IL, Poster No. 15, p. 30 (Mar. 18–31, 1993).

Dunleavy, J.M., "*Curtobacterium plantarum* sp. nov. Is Ubiquitous in Plant Leaves and Is Seed Transmitted in Soybean and Corn", *International Journal of Systematic Bacteriology*, 39, 240–249, (Jul. 1989).

Dybvig, K., et al., "Transposition of Gram–Positive Transposon Tn916 in *Acholeplasma laidlawii* and *Mycoplasma pulmonis*", *Science*, 235, 1392–1394, (Mar. 13, 1987).

Edallo, S., et al., "Chromosomal Variation and Frequency of Spontaneous Mutation Associated with in vitro Culture and Plant Regeneration in Maize", *Maydica*, 26, 39–56, (1981).

European Patent Office, Decision T153/88 (Stahlwerke Peine–Salzgitter/Hot strip) Issued by Technical Board of Appeal 3.3.3 on Jan. 9, 1991 (Not Published in the Official Journal): English Translation from [1997] EPOR pp. 371 to pp. 378, 371–378, (1997).

Fast, P.G., et al., "*Bacillus thuringiensis* δ–Endotoxin: Evidence that Toxin Acts at the Surface of Susceptible Cells", *Experientia*, 34, 762–763, (1978).

Faust, R.M., et al., "Bacteria and Their Toxins as Insecticides", In: *Microbial and Viral Pesticides*, Kurstak, E., (ed.), Marcel Dekker, Inc., New York, 75–208, (1982).

Finkle, B.J., et al., "Growth and Regeneration of Alfalfa Callus Lines After Freezing in Liquid Nitrogen", *Plant Science*, 42, 133–140, (1985).

Finney, D.J., in: *Probit Analysis: A Statistical Treatment of the Sigmoid Response Curve*, iii–ix, (1952).

Fischhoff, D.A., et al., "Insect Tolerant Transgenic Tomato Plants", *Bio/technology*, 5, 807–812, (1987).

Fromm, M., et al., "Transient Expression and Stable Transformation of Maize Using Microprojectiles", *In: Plant Molecular Biology*, vol. 2, Herrmann, R.G., et al., (eds.), Plenum Press, New York, 219, (1991).

Fukuto, T.R., "Physicochemical Aspects of Insecticidal Action", In: *Insecticidal Biochemistry and Physiology*, Wilkinson, C.F., (ed.), Plenum Press, New York, 397–428, (1976).

Gallagher, S., "Progress and Promise of the Particle Gun", *Ag Biotechnology News*, 6, 12–13, (Mar.–Apr. 1989).

Gallie, D.R., et al., "The 5'–leader Sequence of Tobacco Mosaic Virus RNA Enhances the Expression of Foreign Gene Transcripts in Vitro and in Vivo", *Nucleic Acids Research*, 15, 3257–3273, (1987).

Gatehouse, A.M.R., et al., "Assessment of the Antimetabolic Effects of Trypsin Inhibitors from Cowpea (*Vigna unguiculata*) and Other Legumes on Development of the Bruchid Beetle *Callosobruchus maculatus*", *J. Sci. Food Agric.*, 34, 345–350, (1983).

Genovesi, A.D., et al., "Embryogenesis in Callus Derived from Rice Microspores", *Plant Cell Reports*, 1, 257–260, (1982).

Georghiou, G.P., et al., "Factors Influencing the Evolution of Resistance", In: *Pesticide Resistance: Strategies and Tactics for Management*, Committee on Strategies for the Management of Pesticide Resistant Pest Populations, Board on Agriculture, National Research Council, National Academy Press, Washington, D.C., 157–169, (1986).

Gerlach, W.L., "Genetic Engineering: Its Place in Plant Breeding", In: *Plant Breeding and Genetic Engineering*, Zakri, A.H., (ed.), Society for the Advancement of Breeding Researches in Asia and Oceania, Bangi, Malaysia, 269–277, (1988).

Goff, S.A., et al., "Transactivation of Anthocyanin Biosynthetic Genes Following Transfer of β Regulatory Genes into Maize Tissues", *EMBO Journal*, 9, 2517–2522, (1990).

Goldburg, R.J., et al., "Are B.T.K. Plants Really Safe to Eat?", *Bio/technology*, 8, 1011–1015, (Nov. 1990).

Goldfarb, B., et al., "Transient Expression of Microprojectile–Introduced DNA in Douglas–Fir", *J. Cell. Biochem.*, 13D, Abstract No. M121, p. 259 (1989).

Goldman, S.L., et al., "Transformation of *Zea mays* by *Agrobacterium tumefaciens*: Evidence for Stable Genetic Alterations", *Journal of Cellular Biochemistry*, 11B, Abstract No. F 202, p. 26, (1987).

Gordon, P.N., et al., "Plant Regeneration from Tissue Cultures of Maize", *Maize Genetics Cooperation Newsletter*, 51, 79–80, (Mar. 1, 1977).

Gordon–Kamm, W.J., et al., "Transformation of Maize Using Microprojectile Bombardment: An Update and Perspective", *In Vitro Cellular and Developmental Biology*, 27, 21–27, (Jan. 1991).

Green, C.E., "New Developments in Plant Tissue Culture and Plant Regeneration", In: *Basic Biology of New Developments in Biotechnology*, Hollaender, A., et al., (eds.), Plenum Press, New York, 195–209, (1983).

Green, C.E., "Somatic Embryogenesis and Plant Regeneration from the Friable Callus of *Zea mays*", *Proceedings of the 5th International Congress on Plant Tissue & Cell Culture*, Tokyo, Japan, 107–108, (1982).

Haccius, B., "Question of Unicellular Origin of Non–Zygotic Embryos in Callus Cultures", *Phytomorphology*, 28, 74–81, (1978).

Hallborn, J., et al., "Xylitol Production By Recombinant *Saccharomyces cerevisiae*", *Bio/Technology*, 9, 1090–1095, (Nov. 1991).

Harms, C.T., et al., "Regeneration of Plantlets from Callus Cultures of *Zea mays* L.", *Z. Ptlanzenzuchtg.* 77, 347–351, (1976).

Hartree, E.F., "Determination of Protein: A Modification of the Lowry Method that Gives a Linear Photometric Response", *Analytical Biochemistry*, 48, 422–427, (1972).

Harvey, W.R., et al., "Potassium Ion Transport ATPase in Insect Epithelia", *J. Exp. Biol.*, 106, 91–117, (1983).

Heimpel, A.M., et al., "Recent Advances in the Knowledge of Some Bacterial Pathogens of Insects", *Proceedings of the Tenth International Congress of Entomology*, vol. 4, 711–722, (1956).

Heimpel, A.M., et al., "The Site of Action of Crystalliferous Bacteria in Lepidoptera Larvae", *Journal of Insect Pathology*, 1, 152–170, (1959).

Hernalsteens, J.–P., et al., "An Agrobacterium–Transformed Cell Culture from the Monocot *Asparagus officinalis*", *The EMBO Journal*, 3, 3039–3041, (Dec. 1984).

Hibberd, K.A., "Induction, Selection, and Characterization of Mutants in Maize Cell Cultures", In: *Cell Culture and Somatic Cell Genetics of Plants*, vol. 1, Vasil, I.K., (ed.), Academic Press, Inc., Orlando, FL, 571–576, (1984).

Hickle, L.A., et al., "Analytical Chemistry of *Bacillus thuringiensis*: An Overview", *In: Analytical Chemistry of Bacillus thuringiensis*, Hickle, L.A., et al., (eds.), Developed from a Symposium Sponsored by the Division of Agrochemicals at the 198th National Meeting of the American Chemical Society, Miami Beach, FL, vii–ix, 1–8, (Sep. 10–15, 1989).

Hilder, V.A., et al., "A Novel Mechanism of Insect Resistance Engineered into Tobacco", *Nature*, 330, 160–163, (Nov. 12, 1987).

Hodges, T.K., et al., "Genotpye Specificity of Somatic Embryogenesis and Regeneration in Maize", *Bio/technology*, 4, 219–223, (Mar. 1986).

Hodges, T.K., et al., "Regeneration of Maize", In: *Biotechnology in Plant Science*, Zaitlin, M., et al., (ed.), Academic Press, Inc., Orlando, FL, 15–33, (1985).

Hoekema, A., et al., "Codon Replacement in the PKG1 Gene of *Saccharomyces cerevisiae*: Experimental Approach to Study the Role of Biased Codon Uaage in Gene Expression", *Molecular and Cellular Biology*, 7, 2914–2924, (Aug. 1987).

Hofmann, C., et al., "Binding of the Delta Endotoxin from *Bacillus thuringiensis* to Brush–Border Membrane Vesicles of the Cabbage Butterfly (*Pieris brassicae*)", *Eur. J. Biochem.*, 173, 85–91, (1988).

Hofmann, C., et al., "Specificity of *Bacillus thuringiensis* δ–Endotoxins is Correlated with the Presence of High–Affinity Binding Sites in the Brush Border Membrane of Target Insect Midguts", *Proc. Natl. Acad. Sci. USA*, 85, 7844–7848, (Nov. 1988).

Höfte, H., et al., "Monoclonal Antibody Analysis and Insecticidal Spectrum of Three Types of Lepidopteran–Specific Insecticidal Crystal Proteins of *Bacillus thuringiensis*", *Applied and Environmental Microbiology*, 54, 2010–2017, (Aug. 1988).

Höfte, H., et al., "Structural and Functional Analysis of a Cloned Delta Endotoxin of *Bacillus thuringiensis berliner* 1715", *Eur. J. Biochem.*, 161, 273–280, (1986).

Hollingworth, R.M., "The Biochemical and Physiological Basis of Selective Toxicity", In: *Insecticidal Biochemistry and Physiology*, Wilkinson, C.F., (ed.), Plenum Press, New York, 431–506, (1976).

Horsch, R.B., et al., "A Simple and General Method for Transferring Genes into Plants", *Science*, 227, 1229–1231, (Mar. 8, 1985).

Hu, C.C., et al., "Factors Contributing to the Anomalous Electrophoretic Mobility of Cucumoviruses Coat Proteins in SDS/Polyacrylamide Gels", *Phytopathology*, 83, Abstract No. A393, 1374, (Dec. 1993).

Huber, H.E., et al., "*Bacillus thuringiensis* δ–Endotoxin: Composition and Activation", In: *Pathogenesis of Invertebrate Microbial Diseases*, Davidson, E.W., (ed.), Allanheld, Osmun & Co. Publishers, Inc., Totowa, NJ, 209–234, (1981).

Huber–Lukac, M., et al., "Characterization of Monoclonal Antibodies to a Crystal Protein of *Bacillus thuringiensis* subsp. kurstaki", *Infection and Immunity*, 54, 228–232, (Oct. 1986).

Imbrie–Milligan, C.W., et al., "Microcallus Formation from Maize Protoplasts Prepared from Embryogenic Callus", *Planta*, 168, 395–401, (1986).

Jarrett, P., "Potency Factors in the delta–Endotoxin of *Bacillus thuringiensis* var. *aizawi* and the Significance of Plasmids in their Control", *Journal of Applied Bacteriology*, 58, 437–448, (1985).

Johnson, D.E., "Toxicity of *Bacillus thuringiensis* Entomocidal Protein Toward Cultured Insect Tissue", *Journal of Invertebrate Pathology*, 38, 94–101, (1981).

King, P., et al., "Maize", In: *Handbook of Plant Cell Culture*, vol. 2, Sharp, W.R., et al., (eds.), Macmillan Publishing Company, New York, 69–91, (1984).

Klein, T.M., "Transformation of Maize Through Particle Bombardment", In: *Biotechnology in Agriculture and Forestry*, 25, Maize, Bajaj, Y.P.S., (ed.), Springer–Verlag, Berlin, 241–251, (1994).

Klein, T.M., et al., "Advances in Direct Gene Transfer into Cereals", *In: Genetic Engineering: Principles and Methods*, vol. 11, Setlow, J.K., (ed.), Plenum Publishing Corp., New York, 13–31, (1989).

Klein, T.M., et al., "Particle Bombardment: A Universal Approach for Gene Transfer to Cells and Tissues", *Current Opinion in Biotechnology*, 4, 583–590, (1993).

Klein, T.M., et al., "Particle Gun Technology: A Novel Method for the Introduction of DNA into Living Cells", *Program and Abstracts for an International Symposium: "Biotechnology in Plant Science: Relevance to Agriculture in the Eighties"*, Poster, #28, Ithaca, NY, 25, (Jun. 23–27, 1985).

Klein, T.M., et al., "Progress in the Genetic Transformation of Recalcitrant Crop Species", *Aspects of Applied Biology*, 39, 35–44, (1994).

Klein, T.M., et al., "Stable Genetic Transformation of Intact Nicotiana Cells by the Particle Bombardment Process", *Proc. Natl. Acad. Sci. USA*, 95, 5502–5505, (Nov. 1988).

Klein, T.M., et al., "Transformation of Microbes, Plants and Animals by Particle Bombardment", *Biotechnology*, 10, 286–291, (Mar. 1992).

Knowles, B.H., et al., "Characterization and Partial Purification of a Plasma Membrane Receptor for *Bacillus thuringiensis* var. Kurstaki Lepidopteran–Specific δ–Endotoxin", *J. Cell Sci.*, 83, 89–101, (1986).

Knowles, B.H., et al., "Lectin–Like Binding of *Bacillus thuringiensis* var. Kurstaki Lepidopteran–Specific Toxin is an Initial Step in Insecticidal Action", *FEBS Letters*, 168, 197–202, (Mar. 1984).

Koziel, M.G., et al., "The Insecticidal Crystal Proteins of *Bacillus thuringiensis*: Past, Present and Future Uses", *Biotechnology and Genetic Reviews*, 11, 171–228, (Dec. 1993).

Lamark, T., et al., "DNA Sequence and Analysis of the bet Genes Encoding the Osmoregulatory Choline–Glycine Betaine Pathway of *Escherichia coli*", *Molecular Microbiology*, 5, 1049–1064, (1991).

Langridge, W.H., et al., "Electric Field Mediated DNA Transformation in Plant Protoplasts", *Program and Abstracts for an International Symposium: "Biotechnology in Plant Science: Relevance to Agriculture in the Eighties"*, Ithaca, NY, Poster #30, p. 25, (Jun. 23–27, 1985).

Leason, M., et al., "Inhibition of Pea Leaf Glutamine Synthetase by Methionine Sulphoximine, Phosphinothricin and Other Glutamate Analogues", *Biochemistry*, 21, 855–857, (1982).

Lee, B., "Cereal Transformation", *Plants Today*, 9–11, (Jan.–Feb. 1989).

Lin, F.–F., et al., "Transformation and Analysis of Inducible PAL Genes in Potato", *In Vitro Cellular and Developmental Biology*, 28, Absract No. p–1129, p. 123A, (Mar. 1992).

Lörz, H., et al., "Gene Transfer to Cereal Cells Mediated by Protoplast Transformation", *Mol. Gen. Genet.*, 199, 178–182, (1985).

Lowe, K., et al., "Plant Regeneration via Organogenesis and Embryogenesis in the Maize Inbred Line B73", *Plant Science*, 41, 125–132, (1985).

Luckow, V.A., et al., "Trends in the Development of Baculovirus Expression Vectors", *Bio/Technology*, 6, 47–55, (Jan. 1988).

Lüthy, P., "Insecticidal Toxins of *Bacillus thuringiensis*", *FEMS Microbiology Letters*, 8, 1–7, (1980).

Mackey, C.J., et al., "Transgenic Maize", In: *Transgenic Plants*, vol. 2, Kung, S.–D., et al., (eds.), Academic Press, Inc., 21–33, (Oct. 1992).

Mangano, M.L., et al., "Long–Term Cold Storage of Regenerable Maize Callus", *In Vitro Cellular and Developmental Biology*, 25, Abstract No. 224, p. 66A, (Mar. 1989).

Mariana, T., et al., "The Production and Analysis of Genetically–Engineered Male–Sterile Plants of Maize", *Abstracts, 35th Annual Maize Genetics Conference*, St. Charles, IL, Poster No. 46, p. 45 (Mar. 18–21, 1993).

Martens, J.W.M., et al., "Insecticidal Activity of a Bacterial Crystal Protein Expressed by a Recombinant Baculovirus in Insect Cells", *Applied and Environmental Microbiology*, 56, 2764–2770, (Sep. 1990).

McElroy, D., et al., "Isolation of an Efficient Actin Promoter for Use in Rice Transformation", *The Plant Cell*, 2, 163–171, (Feb. 1990).

Merryweather, A.T., et al., "Construction of Genetically Engineered Baculovirus Insecticides Containing the *Bacillus thuringiensis* subsp. Kurstaki HD–73 Delta Endotoxin", *Journal of General Virology*, 71, 1535–1544, (1990).

Mikula, B.C., "Programming Heritable Epigenetic Change in Gene Expression with Temperature and Light", *Abstracts, 35th Annual Maize Genetics Conference*, St. Charles, IL, p. 5 (Mar. 81–21, 1993).

Mink, G.I., "Pollen– and Seed–Transmetted Viruses and Viroids", *Annu. Rev. Phytopathol.*, 31, 375–402, (1993).

Molnar, S.J., et al., "Initiation of Totipotent Tissue Cultures from Undeveloped Axillary and Secondary Ears", *Maize Genetics Cooperation Newsletter*, 54, 52–53, (Mar. 31, 1980).

Morris, G.D., "Ciba–Geigy Enters the $1.5–Billion/Year Corn Biotech Race", *Chemical Week*, (Sep. 12, 1990).

Murphy, D.W., et al., "*Bacillus thuringiensis* Enzyme–Digested Delta Endotoxin: Effect on Cultured Insect Cells", *Science*, 194, 954–956, (Nov. 26, 1976).

Murray, E.E., et al., "Analysis of Unstable RNA Transcripts of Insecticidal Crystal Protein Genes of *Bacillus thuringiensis* in Transgenic Plants and Electroporated Protoplasts", *Plant Molecular Biology*, 16, 1035–1050, (1991).

Nishiitsutsuji–Uwo, J., et al., "Mode of Action of *Bacillus thuringiensis* δ–Endotoxin: Effect on TN–368 Cells", *Journal of Invertebrate Pathology*, 34, 267–275, (1979).

Ochatt, S.J., et al., "Selection for Salt/Drought Tolerance using Isolated Protoplasts and Protoplast–Derived Calli of Colt Cherry (*Prunis avium x pseudocerasus*)", In: *Progress in Plant Protoplast Research*, Puite, K.J., et al., (eds.), Kluwer Academic Publishers, Dordrecht, The Netherlands, p. 391–392 (1988).

Oeda, K., et al., "Formation of Crystals of the Insecticidal Proteins of *Bacillus thuringiensis* subsp. *aizawai* IPL7 in *Escherichia coli*", *Journal of Bacteriology*, 171, 3568–3571, (Jun. 1989).

Pang, Y., et al., "Synthesis and Toxicity of Full–Length and Truncated Bacterial CryIVD Mosquitocidal Proteins Expressed in Lepidopteran Cells Using a Baculovirus Vector", *Journal of General Virology*, 73, 89–101, (1992).

Park, W.D., et al., "High–Level, Sucrose–Inducible Expression of a Chimeric Patatin–GUS Gene In Leaf Explants of Transgenic Tobacco Plants", *Journal of Cellular Biochemistry*, 13D, Abstract No. M 343, p. 310. (Mar. 27–Apr. 7, 1989).

Perlak, F.J., et al., "Expression of *Bacillus thuringiensis* Proteins in Transgenic Plants", *In: Biotechnology, Biological Pesticides and Novel Plant–Pest Resistance for Insect Pest Management*, Roberts, D.W., et al., (eds.), Insect Pathology Resource Center, Boyce Thompson Institute for Plant Research, Cornel University, Ithaca, NY, 77–81, (1988).

Perlak, F.J., et al., "Genetically Improved Potatoes: Protection from Damage by Colorado Potato Beetles", *Plant Molecular Biology*, 22, 313–321, (1993).

Perlak, F.J., et al., "Insect Resistant Cotton Plants", *Bio/technology*, 8, 939–943, (Oct. 1990).

Poehlman, J.M., et al., In: *Breeding Field Crops*, 3rd Edition, AVI Publishing Company, Inc., Westport, CT, 149–152, (1987).

Poethig, R.S., "Maize—The Plant and Its Parts", In: *Maize for Biological Research*, Sheridan, W.F., (ed.), Plant Molecular Biology Association., Charlottesville, VA, 9–18, (1982).

Porobo–Dessai, A., et al., "Expression of gusA Gene with an Intron in Sweet Potato and Garden Egg Plant", *In Vitro Cellular and Developmental Biology*, 13D, Abstract No. P–1130, p. 123A, (Mar. 1992).

Potrykus, I., et al., "Direct Gene Transfer: State of the Art and Future Potential", *Plant Molecular Biology Reporter*, 3, 117–128, (Summer 1985).

Randolph, L.F., et al., "Developmental Morphology of the Caryopsis in Maize", *Journal of Agricultural Research*, 53, 881–916, (Dec. 15, 1936).

Register III, J.C., et al., "Structure and Function of Selectable and Non–Selectable Transgenes in Maize after Introduction by Particle Bombardment", *Plant Molecular Biology*, 25, 951–961, (1994).

Rhodes, C.A., et al., "Cytogenetic Stability of Aneuploid Maize Tissue Cultures", *Can. J. Genet. Cytol.*, 28, 374–384, (1986).

Rhodes, C.A., et al., "Factors Affecting Tissue Culture Initiation from Maize Tassels", *Plant Science*, 46, 225–232, (1986).

Rice, T.B., "Tissue Culture Induced Genetic Variation in Regenerated Maize Inbreds", *Proceedings of the 37th Annual Corn & Sorghum Industry Research Conference*, 148–162, (1982).

Rosahl, S., et al., "Expression of a Tuber–Specific Storage Protein In Transgenic Tobacco Plants: Demonstration Of An Esterase Activity", *EMBO. J*6, Press Limited, Oxford, England, 1155, (1987).

Roth, B.A., et al., "C1– and R–Dependent Expression of the Maize Bz1 Gene Requires Sequences with Homology to Mammalian myb and myc Binding Sites", *The Plant Cell*, 3, 317–325, (Mar. 1991).

Roth, B.A., et al., "Genetic Regulation of Transient Expression of Maize Anthocyanin Pathway Genes Introduced into Intact Maize Tissues by Microprojectile Bombardment", *Journal of Cellular Biochemistry*, 13D, Abstract No. M 344, p. 310, (Mar. 27–Apr. 7, 1989).

Roush, R.T., et al., "Ecological Genetics of Insecticidal and Acaricide Resistance", *Ann. Rev. Entomol.*, 32, 361–380, (1987).

Rout, J.R., et al., "Agrobacterium–Mediated Gene Transfer to Rice (*Oryza sativa* L.)", *In Vitro Cellular and Developmental Biology*, 31, Abstract No. W–19, 28A, (Mar. 1995).

Russell, J.A., et al., "Physical Trauma and Tungsten Toxicity Reduce the Efficiency of Biolistic Transformation", *Plant Physiol.*, 98, 1050–1056, (1992).

Ruan, A.J., et al., "The Expression of the Napin Gene Under the Control of Its Own Promoter in Transgenic Tobacco Plants", *Journal of Cellular Biochemistry*, 13D, Abstract No. M 345, p. 310, (Mar. 27–Apr. 7, 1989).

Sanford, J.C., "The Biolistic Process", *Plant Physiology*, 89, Abstract No. 9, p. 2, (Apr. 1989).

Sanford, J.C., et al., "Delivery of DNA into Regenerable Tissues of Monocots, Using High–Velocity Microprojectiles", Grant Application No. 86–0183, United States Department of Agriculture, Science and Education, 57 p., (Feb. 27, 1986).

Sass, J.E., "Comparative Leaf Number in the Embryos of Some Types of Maize", *Iowa State Coll. J. Sci.*, 25, 509–512, (1951).

Schafer, W., et al., "T–DNA Integration and Expression in a Monocot Crop Plant after Induction of Agrobacterium", *Nature*, 327, 529–532, (Jun. 11, 1987).

Schardl, C.L., et al., "Design and Construction of a Versatile System for the Expression of Foreign Genes in Plants", *Gene*, 61, 1–11, (1987).

Schnepf, H.E., et al., "Delineation of a Toxin–Encoding Segment of a *Bacillus thuringiensis* Crystal Protein Gene", *The Journal of Biological Chemistry*, 260, 6273–6280, (1985).

Schnepf, H.E., et al., "Specificity–Determining Regions of a Lepidopteran–Specific Insecticidal Protein Produced by *Bacillus thuringiensis*", *The Journal of Biological Chemistry*, 265, 20923–20930, (Dec. 5, 1990).

Scorza, R., et al., "Transformation of Grape (*Vitis vinifera* L.) Somatic Embryos and Regeneration of Transgenic Plants", *Journal of Cellular Biochemistry*, Supplement 18A, Abstract No. X1–310, 102, (Jan. 4–27, 1994).

Sewell, G.H., et al., "Irish Potato, Control of Potato–Infesting Aphids, 1991", *Insecticidal and Acaricide Tests*: 1992, 17, 138–139, (1992).

Sewell, G.H., et al., "Transgenic Potato Plants, Control of Colorado Potato Beetle, 1991", *Insecticidal and Acaricide Tests*: 1992, 17, 138, (1992).

Shaner, D.L., et al., "Mechanism of Action of the Imidazolinones and Cell Culture Selection of Tolerant Maize", In: *Biotechnology in Plant Sciences*, Zaitlin, M., et al., (eds.), Academic Press, Orlando, FL, 287–299, (1985).

Sharman, B.C., "Developmental Anatomy of the Shoot of *Zea mays* L.", *Annals of Botany*, VI, 246–281, (Apr. 1942).

Shatters, Jr., R.G., et al., "Particle Gun Bombardment of Embryogenic Bahiagrass Callus Culture", *Journal of Cellular Biochemistry*, Supplement 18A, Abstract No. X1–311, 102, (Jan. 4–23, 1994).

Shields, R., "Towards Insect–Resistant Plants", *Nature*, 328, 12–13, (Jul. 2, 1987).

Shivakumar, A.G., et al., "Vegetative Expression of the δ–Endotoxin Genes of *Bacillus thuringiensis* subsp. *kurstaki* in *Bacillus subtilis*", *Journal of Bacteriology*, 166, 194–204, (Apr. 1986).

Smith, G.E., et al., "Molecular Engineering of the *Autographa californica* Nuclear Polyhedrosis Virus Genome: Deletion Mutations Within the Polyhedrin Gene", *Journal of Virology*, 46, 584–593, (May 1983).

Somers, D.A., et al., "In Vitro Selection for Herbicide Tolerance in Maize", In: *Biotechnology in Agriculture and Forestry*, 25, Maize, Bajaj, Y.P.S., (ed.), Springer–Verlag, Berlin, 21 p., (1994).

Sorenson, K.A., et al., "Colorado Potato Beetle Control with Bioinsecticides, 1991", *Insecticide and Acaricide Tests*: 1992, 17, 139, (1992).

Spangenberg, G., et al., "Gene Transfer and Regeneration of Transgenic Plants in Forage Grasses", *Journal of Cellular Biochemistry*, Supplement 18A, Abstract No. X1–312, p. 102, (Jan. 4–23, 1994).

Spencer, T.M., et al., "Production of Fertile Transgenic Maize by Electroporation", *In Vitro Cellular and Developmental Biology*, Program Issue, Congress on Tissue and Cell Culture, Abstract No. P–11, 34, (Jun. 4–7, 1994).

St. Julian, G., et al., "Bacteria, Spirochetes, and Rickettsia as Insecticides", *Annals of the New York Academy of Sciences*, 217, 65–75, (1973).

Stolle, C.A., et al., "Cellular Factor Affecting the Stability of β–globulin mRNA", *Gene*, 62, 65–74, (1988).

Strauch, E., et al., "Cloning of a Phosphinothricin N–Acetyltransferase Gene from *Streptomyces viridochromogenes* Tu494 and its Expression in *Streptomyces lividans* and *Escherichia coli*", *Gene*, 63, 65–74, (1988).

Stroo, H.F., et al., "Heterotrophic Nitrification in an Acid Forest Soil and by an Acid–Tolerant Fungus", *Applied and Environmental Microbiology*, 52, 1107–1111, (Nov. 1986).

Sukhapinda, K., et al., "Maize Haploid Protoplast Transformation and Regeneration of Transgenic Plants", *In Vitro Cellular and Developmental Biology*, 28, Abstract No. P–1132, p. 123A, (Mar. 1992).

Suprasanna, P., et al., "Plantlet Regeneration from Glume Calli of Maize (*Zea mays* L.)", *Theor. Appl. Genet.*, 72, 120–122, (1986).

Teeri, T.H., et al., "Mendelian Inheritance of Transgenes in Barley", *Journal of Cellular Biochemistry*, Supplemental 18A, Abstract No. X1–313, p. 102, (Jan. 4–23, 1994).

Thomas, W.E., et al., "Mechanism of Action of *Bacillus thuringiensis* var. *israelensis* Insecticidal δ–Endotoxin", *FEBS Letters*, 154, 362–368, (Apr. 1983).

Tojo, A., et al., "Dissolution and Degradation of *Bacillus thuringiensis* δ–Endotoxin by Gut Juice Protease of the Silkworm *Bombyx mori*", *Applied and Environmental Microbiology*, 45, 576–580, (Feb. 1983).

Tomes, D.T., "Cell Culture, Somatic Embryogenesis and Plant Regeneration in Maize, Rice, Sorghum and Millets", In: *Cereal Tissue and Cell Culture*, Bright, S.W.J., et al., (eds.), Martinus Nijnoff/Dr. W. Junk, Amsterdam, The Netherlands, 175–203, (1985).

Tomes, D.T., "Initiation of Embryogenic Callus Cultures from Immature Embryos of Elite Corn (*Zea mays* L.) Germplasm", *In Vitro*, 20, Abstract No. 146, P. 276, (Mar. 1984).

Tomes, D.T., et al., "The Effect of Parental Genotype on Initiation of Embryogenic Callus from Elite Maize (*Zea mays* L.) Germplasm", *Theor. Appl. Genet.*, 70, 505–509, (1985).

Torne, J.M., et al., "Regeneration of Plants from Mesocotyl Tissue Cultures of Immature Embryos of *Zea mays* L.", *Plant Science Letters*, 17, 339–344, (1980).

Townsend, J.A., et al., "Factors Which Influence the Agrobacterium–Mediated Transformation of Soybean", *Journal of Cellular Biochemistry*, Supplement 18A, Abstract No. X1–104, 78, (Jan. 4–23, 1994).

Vaeck, M., et al., "*Bacillus thuringiensis* Endotoxin Gene Expression and Insect Resistance in Higher Plants", *Pesticide Science*, 20, 319–320, (1987).

Vaeck, M., et al., "Engineering Improved Crops for Agriculture: Protection from Insects and Resistance to Herbicides", In: *Plant Gene Systems and Their Biology*, Key, J.L., et al., (eds.), Alan R. Liss, Inc., New York, 171–181, (1987).

Vaeck, M., et al., "Engineering of Insect Resistant Plants Using a *B. thuringiensis* Gene", *In: Molecular Strategies for Crop Protection*, New York, Alan R. Liss, Inc., 355–366, (1987).

Vaeck, M., et al., "Insect Resistance in Transgenic Plants Expressing *Bacillus thuringiensis* Toxin Gens", *An. Soc. Entomol. Brasil*, 16, 427–435, (1987).

Vaeck, M., et al., "Protein Engineering in Plants: Expression of *Bacillus thuringiensis* Insecticidal Protein Genes", *Cell Culture and Somatic Cell Genetics of Plants*, 6, 425–439, (1989).

Vaeck, M., et al., "Transgenic Plants Protected from Insect Attack", *Nature*, 328, 33–37, (Jul. 2, 1987).

van den Elzen, P.J., et al., "A Chimaeric Hygromycin Resistance Gene as a Selectable Marker in Plant Cells", *Plant Molecular Biology*, 5, 299–302.

van den Elzen, P.J., et al., "Simple Binary Vectors for DNA Transfer to Plant Cells", *Plant Molecular Biology*, 5, 149–154, (1985).

Van Lammeren, A.A., "Developmental Morphology and Cytology of the Young Maize Embryo (*Zea mays* L.)", *Acta Bot. Neerl.*, 35, 169–188, (Aug. 1986).

Vasil, I.K., "Isolation and Culture of Protoplasts of Grasses", *International Review of Cytology*, Supplement 16, Bourne, G.H., et al., (eds.), Academic Press, New York, 79–88, (1983).

Vasil, I.K., "Molecular Improvement of Cereals", *Plant Molecular Biology*, 25, 925–937 (1994).

Vasil, I.K., et al., "Molecular Genetic Improvement of Wheat", *Journal of Cellular Biochemistry*, Supplement 18A, Abstract No. X1–015, p. 78, (Jan. 4–23, 1994).

Vasil, V., et al., "Histology of Somatic Embryogenesis in Cultured Immature Embryos of Maize (*Zea mays* L.)", *Protoplasma*, 127, 1–8, (1985).

Visser, B., et al., "Transgenic Tobacco Plants Expressing a Modified *Bacillus thuringiensis* cryIC Gene", *Journal of Cellular Biochemistry*, Supplement 16F, Abstract No. Y–136, p. 213, (Apr. 3–16, 1992).

Wan, Y., et al., "Development and Use of an Efficient Transformation System for Barley", *Journal of Cellular Biochemistry*, Supplement 18A, Abstract No. X1–013, 78, (Jan. 4–23, 1994).

Wan, Y., et al., "Efficient Production of Transgenic Barley Plants and Analysis of Transgene Expression in Progeny", *In Vitro Cellular and Developmental Biology*, 30A, Program Issue Congress on Cell and Tissue Culture, Abstract P–10, 34, (Jun. 4–7, 1994).

Warren, G.W., et al., "Field Evaluation of Transgenic Tobacco Containing a *Bacillus thuringiensis* Insecticidal Protein Gene", *Journal of Economic Entomology*, 85, 1651–1659, (1992).

Watson, S.A., "Corn Marketing, Processing and Utilization", *In: Corn and Corn Improvement*, 3rd Edition, Sprague, G.F., et al., (eds.), American Society of Agronomy, Inc., et al., Madison, WI, 881–939, (1988).

Webb, R.P., et al., "Superoxide Dismutase Gene Expression in Transgenic Plants", *Journal of Cellular Biochemistry*, Supplement 16F, Abstract No. Y 137, 213, (Apr. 3–16, 1992).

Weck, E., "Are Colorized DNA Sequences an Application of Fuzzy Logic?", *Abstracts, 35th Annual Maize Genetics Conference*, St. Charles, IL, Poster No. 45, p. 45 (Mar. 18–21, 1993).

Weigel, Jr., R.C., et al., "Somatic Embryogenesis in Barley", *In Vitro*, 20, Abstract No. 147, p. 277, (Mar. 1984).

Weissinger, A., et al., "Maize Transformation via Microprojectile Bombardment", *In: Genetic Improvements of Agriculturally Important Crops*, Fraley, R.T., et al., (eds.), Cold Spring Harbor Laboratory, Cold Spring Harbor, NY, 21–25, (1988).

Weissinger, A., et al., "Microprojectile Bombardment for Maize Transformation", *In Vitro Cellular And Developmental Biology*, 23, Program Issue, 38th Annual Meeting of the Tissue Culture Association, Washington, D.C., Abstract No. 254, (Mar. 1987).

Wernicke, W., et al., "Adventitious Embryoid and Root Formation from Rice Leaves", *Z. Pflanzenphysiol. Bd.*, 103, 361–365, (1981).

White, D.W., et al., "Auxin–Inducible Response Promoter Elements", *Journal of Cellular Biochemistry*, Supplement 16F, Abstract No. Y 138, p. 213, (Apr. 3–16, 1992).

Williams, R., et al., "Expression of the Maize Homeobox Gene Knotted–1 in Transgenic Maize", *Abstracts, 35th Annual Maize Genetics Conference*, St. Charles, IL, Poster No. 47, p. 46 (Mar. 18–21, 1993).

Williams, S., et al., "Chemical Regulation of *Bacillus thuringiensis* δ–Endotoxin Expression in Transgenic Plants", *Bio/technology*, 10, 540–543, (May 1992).

Wilson, F.D., et al., "Resistance of Cotton Lines Containing a *Bacillus thuringiensis* Toxin to Pink Bollworm (Lepidoptera: Gelechiidae) and Other Insects", *J. Econ. Entomol.*, 85, 1516–1521, (1992).

Withers, L., et al., "Proline: A Novel Cryoprotectant for the Freeze Preservation of Cultured Cells of *Zea mays* L.", *Plant Physiology*, 64, 675–678, (1979).

Witt, D.P., et al., "Crytotoxicity of *Bacillus thuringiensis* δ–Endotoxins to Cultured Cf–1 Cells Does Not Correlate with In Vivo Activity Toward Spruce Budworm Lavae", *In: Fundamental and Applied Aspects of Invertebrate Pathology*, Samson, R.A., et al., (eds.), Fourth International Colloquium of Invertebrate Pathology, Wangingen, The Netherlands, 3–6, (Aug. 18–22, 1986).

Wohllenben, W., et al., "Nucleotide Sequence of the Phosphinothricin N–Acetyltransferase Gene from *Streptomyces viridochromogenes* Tü494 and Its Expression in *Nicotania tabacum*", *Gene*, 70, 25–37, (1988).

Wong, J.R., et al., "Anthocyanin Regulatory Genes from Maize (B–Peru and C1) Activate the Anthocyanin Pathway in Wheat, Barley and Oat Cells", *Journal of Cellular Biochemistry*, Supplement 15A, p. 159, (1991).

Wood, M., "Blast Those Genes!", *Agricultural Research*, 2 p., (Jun. 1989).

Wu, S., et al., "Characterization of Chitinase cDNA Clones for Acidic and Basic Isoforms of Maize", *Abstracts, 35th Annual Maize Genetics Conference*, St. Charles, IL, Poster No. 48, p. 46 (Mar. 18–21, 1993).

Wuatt, S.D., et al., "Coat Protein Gene–Mediated Resistance to Barley Yellow Dwarf Virus in Maize and Barley", *Phytopathology*, 83, Abstract No. A392, 1374, (Dec. 1993).

Zhang, W., et al., "Analysis of rice Act1 5' Region Activity in Transgenic Rice Plants and the Study of Regulatory Elements in This Region", *Journal of Cellular Biochemistry*, Supplement 16F, Abstract No. Y 139, p. 213, (Apr. 3–16, 1992).

Handbook of Fine Chemicals, Aldrich Chemical Co., p. 508 (1988).

*International Society for Plant Molecular Biology, Third International Congress*, Tucson, AZ, 5 p. (Oct. 6–11, 1991).

*In Vitro Cell. and Devel. Biol.*, 28, Program Issue, 1992 World Congress on Cell and Tissue Culture, Washington, D.C., p. 30, 45–46 (Mar. 1993).

"Keystone Crops", *Agricultural Genetics Report*, p. 2 (Mar.–Apr. 1990).

"Plant Science Research, Inc., Achieves Successful Transformation of Corn", *Genetic Engineering News*, 10, 3 (Mar. 1990).

Abe, K., et al., "Molecular Cloning of a Cysteine Proteinase Inhibitor of Rice (Oryzacystatin)", *The Journal of Biological Chemistry*, 262, 16793–16797 (Dec. 15, 1987).

Adang, M.J., et al., "Characterized Full–Length and Truncated Plasmic Clones of the Crystal Protein of *Bacillus thuringiensis* subsp. *kurstaki* HD–73 and Their Toxicity to *Manduca sexta*", *Gene*, 36, 289–300 (1985).

Akella, V., et al., "Expression in Cowpea Seedings of Chimeric Transgenes after Electroporation into Seed Derived Embryos", *Plant Cell Rep.*, 12, 110–117 (1993).

Al–Feel, W., et al., "Cloning of the Yeast FAS3 Gene and Primary Structure of Yeast Acetyl–CoA Carboxylase", *Proc. Natl. Acad. Sci. USA*, 89, 4534–4538 (May 1992).

Anderson, J.M., et al., "The Encoded Primary Sequence of a Rice Seed ADP–glucose Pyrophosphorylase Subunit and Its Homology to the Bacterial Enzyme", *The Journal of Biological Chemistry*, 264, 12238–12242 (Jul. 25, 1989).

Andrews, D.L., et al., "Characterization of the Lipid Acyl Hydrolase Activity of the Major Potato (*Solanum tuberosum*) Tuber Protein, Patatin, by Cloning and Abundant Expression in a Baculovirus Vector", *Biochem. J.*, 252, 199–206 (1988).

Armstrong, C.L., et al., "Establishment and Maintenance of Friable, Embryoginic Maize Callus and the Involvement of L–Proline", *Planta*, 164, 207–214 (1985).

Armstrong, C.L., et al., "Genetic and Cytogenetic Variation in Plants Regenerated from Organogenic and Friable, Embryogenic Tissue Cultures in Maize", *Crop Science*, 28, 363–369 (1988).

Arondel, V., et al., "Map–Based Cloning of a Gene Controlling Omega–3 Fatty Acid Desaturation in Arabidopsis", *Science*, 258, 1353–1355 (Nov. 20, 1992).

Atanassova, R., et al., "A 126 bp Fragment of a Plant Histone Gene Promoter Confers Preferential Expression in Meristems of Transgenic Arabidopsis", *The Plant Journal*, 2, 291–300 (1992).

Aves, K., et al., "Transformation of an Elite Maize Inbred Through Microprojectile Bombardment of Regenerable Embryonic Callus", *In Vitro Cell. Develop. Biol.*, 28A, Abstract No. P–1134, p. 124A (1992).

Bartley, G.E., et al., "Molecular Cloning and Expression in Photosynthetic Bacteria of a Soybean cDNA coding for Phytoene Desaturase, an Enzyme of the Carotenoid Biosynthesis Pathway", *Proc. Natl. Acad. Sci. USA*, 88, 6532–6536 (Aug. 1991).

Belanger, F.C., et al., "Molecular Basis for Allelic Polymorphism of the Maize Globulin–1 Gene", *Genetics*, 129, 863–872 (Nov. 1991).

Bernasconi, P., et al., "Functional Expression of *Arabidopsis thaliana* Anthranilate Synthase Subunit I in *Escherichia coli*", *Plant Physiol.*, 106, 353–358 (1994).

Binns, A.N., "Agrobacterium–Mediated Gene Delivery and the Biology of Host Range Limitations", *Physiologia Plantarum*, 79, 135–139, (1990).

Bol, J.F., et al., "Plant Pathogenesis–Related Proteins Induced by Virus Infection", *Annu. Rev. Phytopathol.*, 28, 113–138, (1990).

Botterman, J., et al., "Engineering Herbicide Resistance in Plants", *Trends in Genetics*, 4, 219–222, (Aug. 1988).

Boulton, M.I., et al., "Specificity of Agrobacterium–Mediated Delivery of Maize Streak Virus DNA to Members of the Gramineae", *Plant Mol. Biol.*, 12, 31–40, (1989).

Bowler, C., et al., "Superoxide Dismutase and Stress Tolerance", *Annu. Rev. Plant Physiol. Plant Mol. Biol.*, 43, 83–116, (1992).

Boyer, J.S., "Water Deficits and Photosynthesis", *In: Water Deficits and Plant Growth*, vol. IV, Kozlowski, T.T., (ed.), Academic Press, New York, pp. 153–190, (1976).

Brignon, P., et al., "Nuclease Sensitivity and Functional Analysis of a Maize Histone H3 Gene Promoter", *Plant Molecular Biology*, 22, 1007–1015, (1993).

Buchanan–Wollaston, V., et al., "Detoxification of the Herbicide Dalapon by Transformed Plants", *J. Cell. Biochem.*, 13D, Abstract No. M503, p. 330, (1989).

Caligiuri, M.G., et al., "Identification of Amino Acid Residues Involved in Feedback Regulation of the Anthranilate Synthase Complex from *Salmonella typhimurium*", *J. Biol. Chem.*, 266, 8328–8335 (May 5, 1991).

Carpita, N.C., "The Biochemistry of "Growing" Cell Walls", In: *Physiology of Cell Expansion During Plant Growth*, Cosgrove, D.J. et al, (eds.), Am. Soc. Plant Physiol., pp. 28–100 (1987).

Charest, P.J., et al., "Factors Affecting the Use of Chloramphenicol Acetyltransferase as a Marker for Brassica Genetic Transformation", *Plant Cell Reports*, 7, 628–631 (1989).

Christou, P., et al., "Cotransformation Frequencies of Foreign Genes in Soybean Cell Cultures", *Theor. Appl. Genet.*, 79, 337–341 (1990).

Christou, P., et al., "Opine Synthesis in Wild–Type Plant Tissue", *Plant Physiol.*, 82, 218–221 (1986).

Chu, C.–C., et al., "Establishment of an Efficient Medium for Anther Culture of Rice Through Comparative Experiments on the Nitrogen Sources", *Scientia Sinica*, 18, 659–668 (Sep.–Oct. 1975).

Comai, L., et al., "Expression in Plants of a Mutant aroA Gene from *Salmonella typhimurium* Confers Tolerance to Glyphosate", *Nature*, 317, 741–744 (Oct. 24, 1985).

Darvill, A., et al., "The Primary Cell Walls of Flowering Plants", In: *The Biochemistry of Plants*, vol. 1, Tolbert, N.E., (ed.), Academic Press, New York, p. 91–162 (1980).

Datta, S.K., et al., "Genetically Engineered Fertile Indica–Rice Recovered from Protoplasts", *Bio/Technology*, 8, 736–740 (Aug. 1990).

Dauce–Le Reverend, B., et al., "Improvement of *Escherichia coli* Strains Overproducing Lysine Using Recombinant DNA Techniques", *European J. Appl. Microbiol. Biotechnol.*, 15, 227–231 (1982).

Dekeyser, R.A., et al., "Evaluation of Selectable Markers for Rice Transformation", *Plant Physiol.*, 90, 217–223 (1989).

Dekeyser, R.A., et al., "Transient Gene Expression in Intact and Organized Rice Tissues", *The Plant Cell*, 2, 591–602 (Jul. 1990).

Depicker, A.G., et al., "A Negative Selection Scheme for Tobacco Protoplast–Derived Cells Expressing the T–DNA Gene 2", *Plant Cell Reports*, 7, 63–66 (1988).

DeWet, J.M.J., et al., "Exogenous Gene Transfer in Maize (*Zea mays*) using DNA–treated Pollen", In: *The Experimental Manipulation of Ovule Tissues*, Chapman, G.P., et al., (eds.), Longman, New York, p. 197–209 (1985).

Domoney, C., et al., "Cloning and Characterization of Complementary DNA for Convicilin, a Major Seed Storage Protein in *Pisum sativum* L.", *Planta*, 159, 446–453 (1983).

Donn, G., et al., "Stable Transformation of Maize with a Chimaeric, Modified Phosphinothricin–Acetyltransferase Gene from *Streptomyces viridochromogenes*", Abstracts, *VIIth International Congress on Plant Tissue Cell Culture*, Amsterdam, The Netherlands, Abstract No. A2–38, p. 53 (Jun. 24–29, 1990).

Dunn, G.M., et al., "Inheritance of Cyclic Hydroxamates in *Zea mays* L.", *Can. J. Plant Sci.*, 61, 583–593 (Jul. 1981).

Dure III, L., et al., "Common Amino Acid Sequence Domains Among the LEA Proteins of Higher Plants", *Plant Molecular Biology*, 12, 475–486 (1989).

Fennel, A., et al., "Electroporation and PEG Delivery of DNA into Maize microspores", *Plant Cell Reports*, 11, 567–570 (1992).

Finnegan, J., et al., "Transgene Inactivation: Plants Fight Back!", *Bio/Technology*, 12, 883–888 (Sep. 1994).

Fisher, D.K., et al., "Starch Branching Enzyme II from Maize Endosperm", *Plant Physiol.*, 102, 1045–1046 (1993).

Flavell, R., et al., "Prospects for Transforming Monocot Crop Plants", *Nature*, 307, 108–109 (Jan. 12, 1984).

Fry, S.C., "Introduction to the Growing Cell Wall", In: *The Growing Plant Cell Wall: Chemical and Metabolic Analysis*, Longman Scientific and Technical, New York, pp. 1–5, 102–109 (1988).

Geiser, M., et al., "The Hypervariable Region in the Genes Coding for Entomopathogenic Crystal Proteins of *Bacillus thuringiensis*: Nucleotide Sequence of the kurhd1 gene of subsp. *kurstaki* HD1", *Gene*, 48, 109–118 (1986).

Gepts, P., et al., "Enhanced Available Methionine Concentration Associated with Higher Phaseolin Levels in Common Bean Seeds", *Theor. Appl. Genet.*, 69, 47–53 (1984).

Goodman, R.M., et al., "Gene Transfer in Crop Improvement", *Science*, 236, 48–54 (Apr. 3, 1987).

Guerineau, F., et al., "Sulfonamide Resistance Gene for Plant Transformation", *Plant Molecular Biology*, 15, 127–136 (1990).

Guerrero, F.D., et al., "Turgor–Responsive Gene Transcription and RNA Levels Increase Rapidly When Pea Shoots are Wilted. Sequence and Expression of Three Inducible Genes", *Plant Mol. Biol.*, 15, 11–26 (1990).

Gupta, A.S., et al., "Increased Resistance to Oxidative Stress in Transgenic Plants that Overexpress Chloroplastic Cu/Zn Superoxide Dismutase", *Proc. Natl. Acad. Sci. USA*, 90, 1629–1633 (Feb. 1993).

Hallauer, A.R., et al., "Corn Breeding", In: *Corn and Corn Improvement*, 3rd Edition, Sprague, G.F., et al., (eds.), Agronomy Soc. Amer., Madison, WI, pp. 463–564 (1988).

Haughn, G.W., "Transformation with a Mutant Arabidopsis Acetolactate Synthase Gene Renders Tobacco Resistant to Sulfonylurea Herbicides", *Mol. Gen. Genet.*, 211, 266–271 (1988).

Herrera–Estrella, L., et al., "Use of Reporter Genes to Study Gene Expression in Plant Cells", In: *Plant Molecular Biology Manual B1*, Gelvin, S.B., (eds.), Kluwer Academic Publishers, Dordrecht, Belgium, p. 1–22 (1988).

Hiei, Y., et al., "Efficient Transformation of Rice (*Oryza sativa* L.) Mediated by Agrobacterium and Sequence Analysis of the Boundaries of the T–DNA", *The Plant Journal*, 6, 271–282 (1994).

Höfte, H., et al., "Insecticidal Crystal Proteins of *Bacillus thuringiensis*", *Microbiol. Rev.*, 53, 242–255 (Jun. 1989).

Holmstroöm, K.–O., et al., "Production of the *Escherichia coli* Betain–aldehyde Dehydrogenase, an Enzyme Required for the Synthesis of the Osmoprotectant Glycine Betaine, in Transgenic Plants", *The Plant Journal*, 6, 749–758 (1994).

Hong, B., et al., "Cloning and Characterization of cDNA Encoding a mRNA Rapidly–Induced by ABA in Barley Aleurone Layers", *Plant Molecular Biology*, 11, 495–506 (1988).

Hookyaas–Van Slogteren, G.M.S., et al., "Expression of Ti Plasmid Genes in Monocotyledonous Plants Infected with *Agrobacterium tumefaciens*", *Nature*, 311, 763–764 (Oct. 25, 1984).

Hu, N.–T., et al., "Primary Structure of a Genomic Zein Sequence of Maize", *The EMBO Journal*, 1, 1337–1342 (1982).

Huang, Y.–W., et al., "Factors Influencing Stable Transformation of Maize Protoplasts by Electroporation", *Plant Cell, Tissue and Organ Culture*, 18, 281–296 (1989).

Jähne, A., et al., "Genetic Engineering of Cereal Crop Plants: A Review", *Euphytica*, 85, 35–44, (1995).

Jähne, A., et al., "Regeneration of Fertile Plants from Protoplats Derived from Embryogenic Cell Suspensions of Barley (*Hordeum vulgare* L.)", *Plant Cell Rep.*, 10, 1–6, (1991).

Jaworski, J.G., et al., "A Cerulenin Insensitive Short Chain 3–Ketoacyl–Acyl Carrier Protein Synthase in *Spinacia oleracea* Leaves", *Plant Physiol.*, 90, 41–44, (1989).

Jayne, S., et al., "Analysis of Elite Transgenic Maize Plants Produced by Microprojectile Bombardment", *Program and Abstracts, International Society for Plant Molecular Biology, Third International Congress*, Tucson, AZ, Abstract No. 338 (Oct. 6–11, 1991).

Jaynes, J.M., et al., "Plant Protein Improvement by Genetic Engineering: Use of Synthetic Genes", *Trends in Biotechnology*, 4, 314–320 (Dec. 1986).

Johri, M.M., et al., "Genetic Approaches to Meristem Organization", In: *Maize for Biological Research*, Sheridan, W.F., (ed.), Plant Molecular Biology Association, Charlottesville, VA, pp. 301–310 (1982).

Jones, H., et al., "Recent Advances in Plant Electroporation", *Oxford Surveys of Plant Molecular and Cell Biology*, 4, 347–357 (1987).

Jones, H., et al., "Transient Gene Expression in Electroporated Solanum Protoplasts", *Plant Mol. Biol.*, 13, 503–511 (1989).

Josefsson, L.G., et al., "Structure of a Gene Encoding the 1.7 S Storage Protein, Napin, from *Brassica napus*", *The Journal of Biological Chemistry*, 262, 12196–12201 (Sep. 5, 1987).

Kaasen, I., et al., "Molecular Cloning and Physical Mapping of the otsBA Genes, Which Encode the Osmoregulatory Trehalose Pathway of *Escherichia coli*: Evidence that Transcription is Activated by KatF (AppR)", *Journal of Bacteriology*, 174, 889–898 (Feb. 1992).

Kao, K.N., et al., "Nutritional Requirements for Growth of *Vicia hajastana* Cells and Protoplasts at a Very Low Population Density in Liquid Media", *Planta*, 126, 105–110 (1975).

Kay, R., et al., "Duplication of CaMV 35S Promoter Sequences Creates a Strong Enhancer for Plant Genes", *Science*, 236, 1299–1302 (Jun. 5, 1987).

Kim, C.-S., et al., "Improvement of Nutritional Value and Functional Properties of Soybean Glycinin by Protein Engineering", *Protein Engineering*, 3, 725–731 (1990).

Klein, T.M., et al., "Regulation of Anthocyanin Biosynthetic Genes Introduced into Intact Maize Tissues by Microprojectiles", *Proc. Natl. Acad. Sci. USA*, 86, 6681–6685 (Sep. 1989).

Knight, M.R., et al., "Transgenic Plant Aequorin Reports the Effects of Touch and Cold–Shock and Elicitors on Cytoplasmic Calcium", *Nature*, 352, 524–526 (Aug. 8, 1991).

Kogami, H., et al., "Molecular and Physiological Evaluation of Transgenic Tobacco Plants Expressing a Maize Phosphoenolpyruvate Carboxylase Gene Under the Control of the Cauliflower Mosaic Virus 35S Promoter", *Biol. Abstr.*, 98, Abstract. No. 147991, p. AB–596 (1994).

Kononowicz, H., et al., "Subdomains of the Octopine Sythase Upstream Activating Element Direct Cell–Specific Expression in Transgenic Tobacco Plants", *The Plant Cell*, 4, 17–27 (Jan. 1992).

Kozak, M., "Compilation and Analysis of Sequences Upstream from the Translational Start Site in Eukaryotic mRNAs", *Nuc. Acids Res.*, 12, 857–872 (1984).

Kriz, A.L., et al., "Characterization of the Maize Globulin–2 Gene and Analysis of Two Null Alleles", *Biochemical Genetics*, 29, 241–254 (1991).

Kuhlemeier, C., et al., "Regulation of Gene Expression in Higher Plants", *Ann. Rev. Plant Physiol.*, 38, 234–239 (1987).

Lamppa, G., et al., "Analysis of Two Linked Genes Coding for the Acyl Carrier Protein (ACP) from *Arabidopsis thaliana* (Columbia)", *Plant Molecular Biology*, 16, 469–474 (1991).

Larkins, B.A., et al., "Modification of Maize–Seed Protein Quality", *Am. J. Clin. Nutr.*, 58, 264S–269S (1993).

Lee, J.S., et al., "Gene Transfer into Intact Cells of Tobacco by Electroporation", *Korean J. Genetics*, 11, 65–72 (1989).

Lemaux, P.G., et al., "Selection of Stable Transformants from Maize Suspension Cultures Using the Herbicide Bialaphos", *J. Cell. Biochem.*, 14e, Abstract R230, p. 304 (Mar. 31, 1990).

Li, B.–J., et al., "Introduction of Foreign Genes into the Seed Embryo Cells of Rice by Electroinjection and the Regeneration of Transgenic Rice Plants", *Science in China*, 34, 923–931 (Aug. 1991).

Li, X.–Q., et al., "GUS Expression in Rice Tissues Using Agrobacterium–Mediated Transformation", *Program and Abstracts, International Society for Plant Molecular Biology, Third International Congress*, Tucson, AZ, Abstract No. 385 (Oct. 6–11, 1991).

Lindsey, K., et al., "Stable Transformation of Sugarbeet Protoplasts by Electroporation", *Plant Cell Rep.*, 8, 71–74 (1989).

Lindsey, K., et al., "The Permeability of Electroporated Cells and Protoplasts of Sugar Beet", *Planta*, 172, 346–355 (1987).

Lindsey, K., et al., "Transient Gene Expression in Electroporated Protoplasts and Intact Cells of Sugar Beet", *Plant Mol. Biol.*, 10, 43–52 (1987).

Lopes, M.A., et al., "Endosperm Origin, Development and Function", *The Plant Cell*, 5, 1383–1399 (Oct. 1993).

Lu, C., et al., "Improved Efficiency of Somatic Embryogenesis and Plant Regeneration on Tissue Cultures of Maize (*Zea mays* L.)", *Theor. Appl. Genet.*, 66, 285–289 (1983).

Lu, C., et al., "Somatic Embryogenesis in *Zea mays* L.", *Theor. Appl. Genet*, 62, 109–112 (1982).

Maas, C., et al., "A Highly Optimized Monocot Expression Cassette: Applications for Barley Transformation and Barley Virus Research", *Program and Abstracts, International Society for Plant Molecular Biology, Third International Congress*, Tucson, AZ, Abstgract No. 386 (Oct. 6–11, 1991).

Maddock, S.E., et al., "Expression in Maize Plants of Wheat Germ Agglutinin, a Novel Source of Insect Resistance", *Program and Abstracts, International Society for Plant Molecular Biology, Third International Congress*, Tucson, AZ, Abstract No. 372 (Oct. 6–11, 1991).

Malan, C., et al., "Correlation Between CuZn Superoxide Dismutase and Glutathione Reductase, and Environmental and Xenobiotic Stress Tolerance in Maize Inbreds", *Plant Science*, 69, 157–166 (1990).

Mariani, C., et al., "Engineered Male Sterility in Plants", *Symposia of the Society for Experimental Biology*, No. XLV, Proceedings of a Meeting Held at the University of Glasgow, Scotland, 271–279 (1991).

Marks, M.D., et al., "Nucleotide Sequence Analysis of Zein mRNAs from Maize Endosperm", *The Journal of Biological Chemistry*, 260, 16451–16459 (Dec. 25, 1985).

Matthews, B.F., et al., "Nutritional Improvement of the Aspartate Family of Amino Acids in Edible Crop Plants", *Amino Acids*, 4, 21–34 (1993).

McCue, K.F., et al., "Drought and Salt Tolerance: Towards Understanding and Application", *TIBTECH*, 8, 358–362 (Dec. 1990).

McElroy, D., et al., "Isolation of an Efficient Actin Promoter for Use in Rice Transformation", *The Plant Cell*, 2, 163–171 (Feb. 1990).

Mehta, T., et al., "A Step Towards Developing Transgenic Plants With High Nutritional Quality", *Proc. Indian Natl. Sci. Acad.*, B60, 375–380 (1994).

Milborrow, B.V., "Abscisic Acid and Other Hormones", In: *The Physiology and Biochemistry of Drought Resistance in Plants*, Paleg, L.G., et al., (eds.), Academic Press, New York, p. 347–388 (1981).

Montoliu, L., et al., "A Tandem of α–Tubulin Genes Preferentially Expressed in Radicular Tissues from *Zea mays*", *Plant Molecular Biology*, 14, 1–15 (1989).

Morikawa, H., et al., "Gene Transfer into Intact Plant Cells by Electroinjection Through Cell Walls and Membranes", *Gene*, 41, 121–124 (1986).

Mórocz, S., et al., "An Improved System to Obtain Fertile Regenerants via Maize Protoplasts Isolated From a Highly Embryogenic Suspension Culture", *Theor. Appl. Genet.*, 80, 721–726 (1990).

Mundy, J., et al., "Abscisic Acid and Water–Stress Induce the Expression of a Novel Rice Gene", *The EMBO Journal*, 7, 2279–2286 (1988).

Mundy, J., et al., "Selective Expression of a Probable Amylase/Protease Inhibitor in Barley Aleurone Cells: Comparison to the Barely Amylase/Subtilisin Inhibitor", *Planta*, 169, 51–63 (1986).

Murashige, T., et al., "A Revised Medium for Rapid Growth and Bio Assays with Tobacco Tissue Cultures", *Physiol. Plant.*, 15, 473–497 (1962).

Murray, E.E., et al., "Codon Usage in Plant Genes", *Nuc. Acids Res.*, 17, 477–498 (1989).

Nelson, R.S., "Virus Tolerance, Plant Growth and Field Performance of Transgenic Tomato Plants Expressing Coat Protein from Tobacco Mosaic Virus", *Bio/Technology*, 6, 403–409 (Apr. 1988).

Nishida, I., et al., "The Gene and the RNA for the Precursor to the Plastid–Located Glycerol–3–phosphate Acyltransferase of *Arabidopsis thaliana*", *Plant Molecular Biology*, 21, 267–277 (1993).

Niyogi, K.K., et al., "Suppressors of trp 1 Fluorescence Identify a New Arabidopsis Gene, TRP4, Encoding the Anthranilate Synthase β Gene", *The Plant Cell*, 5, 1011–1027 (Sep. 1993).

Niyogi, K.K., et al., "Two Anthranilate Synthase Genes in Arabidopsis: Defense–Related Regulation of the Tryptophan Pathway", *The Plant Cell*, 4, 721–733 (Jun. 1992).

O'Reilly, D.R., et al., "A Baculovirus Blocks Insect Molting by Producing Ecdysteroid UDP–Glucosyl Transferase", *Science*, 245, 1110–1112 (Sep. 8, 1989).

Parker, W.B., et al., "Selection and Characterization of Sethoxydim–Tolerant Maize Tissue Cultures", *Plant Physiol.*, 92, 1220–1225 (1990).

Paszkowski, J., et al., "Direct Gene Transfer to Plants", *The EMBO Journal*, 3, 2717–2722 (1984).

Piatkowski, D., et al., "Characterization of Five Abscisic Acid–Responsive cDNA Clones Isolated from the Desiccation–Tolerant Plant *Craterostigma plantagineum* and Their Relationship to Other Water–Stress Genes", *Plant Physiology*, 94, 1682–1688 (Jun. 1990).

Pioneer Hi–Bred International, Inc., Application for Release in the Environment Under 7 CFR 340, Corn Plants Genetically Engineered to Express Wheat Germ Agglutinin (WGA) Genes, in Order to Confer Resistance to the European Corn Borer (*Ostrinia nubilalis*) and Tolerance to Glufosinate Herbicides, 92–022–03, NO CIB COPY, p. 11 (May 4, 1992).

Pioneer Hi–Bred International, Inc., Release of Genetically Engineered Corn Plants, Application Under 7 CFR 340, Permit No. 92–174–02, NO CBI, p. 8 (Nov. 3, 1992).

Pioneer Hi–Bred International, Inc., Release of Genetically Engineered Corn Plants, Application Under 7 CFR 340, Permit No. 92–212–01, CBI DELETED, p. 11 (Nov. 16, 1992).

Pioneer Hi–Bred International, Inc., Release of Genetically Engineered Corn Plants, Application Under 7 CFR 340, Permit No. 92–330–01, CBI–DELETED, p. 13 (Apr. 13, 1993).

Poehlman, J.M., "Backcross Breeding", In: *Breeding Field Crops*, 3rd Edition, AVI Publishing Company, Inc., Westport, CT, 203–206 (1988).

Poehlman, J.M., "Breeding Corn (Maize)", In: *Breeding Field Crops*, 3rd Edition, AVI Publishing Co., Westport, CT, p. 452 (1988).

Potrykus, I., et al., "Direct Gene Transfer to Cells of a Graminaceous Monocot", *Mol. Gen. Genet.*, 199, 183–188 (1985).

Potter, H., et al., "Enhancer–Dependent Expression of Human κ Immunoglobulin Genes Introduced into Mouse Pre–B Lymphocytes by Electroporation", *Proc. Natl. Acad. Sci. USA*, 81, 7161–7165 (Nov. 1984).

Puite, K.J., et al., "Electrofusion a Simple and Reproducible Technique in Somatic Hybridization of *Nicotiana plumbaginifolia* mutants", *Plant Cell Rep.*, 4, 274–276 (1985).

Ranch, J.P., et al., "Expression of 5–Methyltyrptophan Resistance in Plants Regenerated from Resistant Cell Lines of *Datura innoxia*", *Plant Physiol.*, 71, 136–140 (1983).

Rathinasabapathi, B., et al., "Metabolic Engineering of Glycine Betaine Synthesis: Plant Betaine Aldehyde Dehydrogenases Lacking Typical Transit Peptides Are Targeted to Tobacco Chloroplasts Where They Confer Betaine Aldehyde Resistance", *Planta*, 193, 155–162 (1994).

Rice, J.A., et al., "Expression of Synthetic High Lysine Seed Storage Proteins can Significantly Increase the Accumulated Levels of Lysine in Mature Seeds of Transgenic Crop Plants", *Journal of Cellular Biochemistry*, Suppl., 18 part A, p. 107 (1994).

Richaud, F., et al., "Chromosomal Location and Nucleotide Sequence of the *Escherichia coli* dapA Gene", *Biol. Abstracts*, 82, Abstract No. 3396, p. AB–391 (1986).

Shen, B., et al., "Partial Sequencing and Mapping of Clones from Two Maize cDNA Libraries", *Plant Molecular Biology*, 26, 1085–1101 (1994).

Shen, B., et al., "Partial Sequencing and Mapping of Clones from Two Maize cDNA Libraries", *EMBL Sequence Data Library*, Heidelberg, Germany (Oct. 1, 1994).

Shigekawa, K., et al., "Electroporation of Eukaryotes and Prokaryotes: A General Approach to the Introduction or Macromolecules into Cells", *BioTechniques*, 6, 742–751 (1988).

Shillito, R.D., et al., "High Efficiency Direct Gene Transfer to Plants", *Bio/Technology*, 3, 1099–1103 (Dec. 1985).

Shorrosh, B.S., et al., "Molecular Cloning, Characterization, and Elicitation of Acetyl–CoA Carboxylase from Alfalfa", *Proc. Natl. Acad. Sci. USA*, 91, 4323–4327, (May 1994).

Shotwell, M.A., et al., "Analysis of Seed Storage Protein Genes of Oats", *The Journal of Biological Chemistry*, 265, 9652–9658, (Jun. 15, 1990).

Shotwell, M.A., et al., "The Biochemistry and Molecular Biology of Seed Storage Proteins", In: *The Biochemistry of Plants*, vol. 15, Marcus, A., (ed.), Academic Press, Inc., San Diego, CA, pp. 297–345 (1989).

Smith, I.K., et al., "Properties and Functions of Glutathione Reductase in Plants", *Physiol. Plant.*, 77, 449–456 (1989).

Soberon, X., et al., "Construction and Characterization of New Cloning Vehicles. IV. Deletion Derivatives of pBR322 and pBR325", *Gene*, 9, 287–305 (1980).

Songstad, D.D., et al., "Transient Expression of GUS and Anthocyanin Constructs in Intact Maize Immature Embryos Following Electroporation", *Plant Cell, Tissue and Organ Culture*, 33, 195–201 (1993).

Stalker, D.M., et al., "Herbicide Resistance in Transgenic Plants Expressing a Bacterial Detoxification Gene", *Science*, 242, 419–422 (Oct. 21, 1988).

Stark, D.M., et al., "Regulation of the Amount of Starch in Plant Tissues by ADP Glucose Pyrophosphorylase", *Science*, 258, 287–291 (Oct. 9, 1992).

Stiefel, V., et al., "Expression of a Maize Cell Wall Hydroxyproline–Rich Glycoprotein Gene in Early Leaf and Root Vascular Differentiation", *The Plant Cell*, 2, 785–793 (Aug. 1990).

Stougaard, J., "Substrate–Dependent Negative Selection in Plants Using a Bacterial Cytosine Deaminase Gene", *The Plant Journal*, 3, 755–761 (1993).

Suttie, J., et al., "Use of Different Selection Agents to Produce Maize Transformants of an Elite Geneotype Using Microprojectile Bombardment", *Program and Abstracts, International Society for Plant Molecular Biology, Third International Congress*, Tucson, AZ, Abstract No. 426 (Oct. 6–11, 1991).

Usami, S., et al., "Absence in Monocotyledonous Plants of the Diffusible Plant Factors inducing T–DNA Circularization and vir Gene Expression in Agrobacterium", *Mol. Gen. Genet.*, 209, 221–226 (1987).

Vasil, V., et al., "Isolation and Maintenance of Embryogenic Cell Suspension Cultures of Gramineae", In: *Cell Culture and Somatic Cell Genetics of Plants*, vol. I, Academic Press, pp. 152–158 (1984).

Vasil, V., et al., "Regeneration of Plants from Embryogenic Suspension Culture Protoplasts of Wheat (*Triticum aestivum* L.)", *Bio/Technology*, 8, 429–434 (May 1990).

Vernon, D.M., et al., "A Novel Methyl Transferase Induced by Osmotic Stress in the Facultative Halophyte *Mesembryanthemum crystallinum*", *The EMBO Journal*, 11, 2077–2085 (1992).

Viotti, A., et al., "Each Zein Gene Class Can Produce Polypeptides of Different Sizes", *The EMBO J.*, 4, 1103–1110 (1985).

Wan, Y., et al., "Maize Transformation and Regeneration of Transgenic Plants by Microprojectile Bombardment of Type I Callus", *Abstracts, 35th Annual Maize Genetics Conference*, St. Charles, IL, p. 5 (Mar. 18–21, 1993).

Werr, W., et al., "Structure of the Sucrose Synthase Gene on Chromosome 9 of *Zea mays* L", *The EMBO Journal*, 4, 1373–1380 (1985).

Whitely, H.R., et al., "The Molecular Biology of Parasporal Crystal Body Formation in *Bacillus thuringiensis*", *Ann. Rev. Microbiol.*, 40, 549–576 (1986).

Wolter, F.P., et al., "Chilling Sensitivity of *Arabidopsis thaliana* with Genetically Engineered Membrane Lipids", *Thge EMBO Journal*, 11, 4685–4692 (1992).

Xiang, C., et al., "The Anti–nptII Gene—A Potential Negative Selectable Marker for Plants", *Plant Physiol.*, 102, 287–293 (1993).

Yamaguchi–Shinozaki, K., et al., "Molecular Cloning and Characterization of 9 cDNAs for Genes that are Responsive To Desiccation in *Arabidopsis thaliana*: Sequence Analysis of One cDNA Clone that Encodes a Putative Transmembrane Channel Protein", *Plant Cell Physiol.*, 33, 217–224 (1992).

Yang, H., et al., "Production of Kanamycin Resistant Rice Tissues Following DNA Uptake into Protoplasts", *Plant Cell Rep.*, 7, 421–425 (1988).

Yang, N.–S., et al., "Maize Sucrose Synthase–1 Promoter Directs Phloem Cell–Specific Expression Gus Gene in Transgenic Tobacco Plants", *Proc. Natl. Acad. Sci. USA*, 87, 4144–4148 (Jun. 1990).

Yanisch–Perron, C., et al., "Improved M13 Phage Cloning Vectors and Host Strains: Nucleotide Sequences of the M13mp18 and pUC19 Vectors", *Gene*, 33, 103–119 (1985).

Yenofsky, R.L., et al., "Isolation and Characterization of a Soybean (*Glycine max*) Lipoxygenase–3 Gene", *Mol. Gen. Genet.*, 211, 215–222 (1988).

Yugari, Y., et al., "Coordinated End–Product Inhibition in Lysine Synthesis in *Escherichia coli*", *Biochem. Biophys. Acta*, 62, 612–614 (1962).

\* cited by examiner

Fig. 4

|  | EXP A | | | | EXP B | | | | | | | | | | | |
|---|---|---|---|---|---|---|---|---|---|---|---|---|---|---|---|---|
| Rep | Row | | | | | | | | | | | | | | | |
| | | B | B | B | B | B | B | B | B | B | B | B | B | B | B | B |
| | | B | B | B | B | B | B | B | B | B | B | B | B | B | B | B |
| Rep 1 | 4 | B | O | X | O | B | O | X | O | X | O | X | O | X | O | B |
| | 3 | B | O | X | O | B | O | X | O | X | O | X | O | X | O | B |
| | 2 | B | O | X | O | B | O | X | O | X | O | X | O | X | O | B |
| | 1 | B | O | X | O | B | O | X | O | X | O | X | O | X | O | B |
| Rep 2 | 4 | B | O | X | O | B | O | X | O | X | O | X | O | X | O | B |
| | 3 | B | O | X | O | B | O | X | O | X | O | X | O | X | O | B |
| | 2 | B | O | X | O | B | O | X | O | X | O | X | O | X | O | B |
| | 1 | B | O | X | O | B | O | X | O | X | O | X | O | X | O | B |
| Rep 1 | 4 | B | O | X | O | B | O | X | O | X | O | X | O | X | O | B |
| | 3 | B | O | X | O | B | O | X | O | X | O | X | O | X | O | B |
| | 2 | B | O | X | O | B | O | X | O | X | O | X | O | X | O | B |
| | 1 | B | O | X | O | B | O | X | O | X | O | X | O | X | O | B |
| | | B | B | B | B | B | B | B | B | B | B | B | B | B | B | B |
| Column | | B | 1 | 2 | 3 | B | 1 | 2 | 3 | 4 | 5 | 6 | 7 | 8 | 9 | 10 | 11 | B | B |

X=Buffer
O=Experimental Material
B=Border

FERTILE TRANSGENIC MAIZE PLANTS CONTAINING A GENE ENCODING THE PAT PROTEIN

BACKGROUND OF THE INVENTION

The present application is a continuation-in-part of U.S. patent application Ser. No. 08/113,561, filed Aug. 25, 1993, pending, and of U.S. patent application Ser. No. 08/233,067, filed Apr. 26, 1994, now U.S. Pat. No. 5,489,520, issue Feb. 6, 1996. The 08/113,561 application was filed as a continuation-in-part of U.S. patent application Ser. No. 07/565,844, filed Aug. 9, 1990, now U.S. Pat. No. 5,550,318 issued Aug. 27, 1996, and the 08/233,067 application is a divisional application of Ser. No. 07/565,844. The entire text and figures of each of the above-referenced disclosures are specifically incorporated herein by reference without disclaimer.

FIELD OF THE INVENTION

The present invention relates generally to the fields of plants, such as maize, and to improved methods of plant breeding. More particularly, it provides methods of increasing yield in plants by introducing a gene encoding phosphinothricin acetyltransferase. The increased yield phenotype may be transferred to other lines of plants by crossing.

DESCRIPTION OF THE RELATED ART

Ever since the human species emerged from the hunting-gathering phase of its existence, and entered an agricultural phase, a major goal of human ingenuity and invention has been to improve crop yield and to alter and improve the characteristics of plants. In particular, man has sought to alter the characteristics of plants to make them more tasty and/or nutritious, to produce increased crop yield or render plants more adaptable to specific environments.

Up until recent times, crop arid plant improvements depended on selective breeding of plants with desirable characteristics. Initial breeding success was probably accidental, resulting from observation of a plant with desirable characteristics, and use of that plant to propagate the next generation. However, because such plants had within them heterogenous genetic complements, it was unlikely that progeny identical to the parent(s) with the desirable traits would emerge. Nonetheless, advances in controlled breeding have resulted from both increasing knowledge of the mechanisms operative in hereditary transmission, and by empirical observations of results of making various parental plant crosses.

Attempts to improve commercially important traits in plants, for example, grain yield in corn and wheat, have consumed the energies of commercial plant breeders in the twentieth century. Clever and sophisticated breeding schemes have been devised, yet the rate of improvement of economically important characters has been only a few to several percent of the mean per year for the past several decades. For various crop plants, it has been established that roughly half of this improvement is due to improved husbandry practices, i.e., environmental effects rather than genetic changes effected by selection. (Lande & Thompson, 1990).

The record available from the crude crop breeding programs of the late nineteenth century through the present is littered with dead ends—failures, for one reason or another. For example, data on the ineffectiveness of mass selection for several corn ear characters as presented by Williams and Welton in 1915 are reproduced and discussed by Sprague & Eberhart (1977). Selection for long and short ears was not effective in separating the population into two distinct subpopulations defined by ear length. Yield, one of the most commercially valuable traits, has been the least responsive to selective breeding programs. Selection from 1907–1914 had no overall effect on yield. An examination of data on corn yield trials published by study stations in Illinois from 1860 to 1900 shows that many corn varieties were included for short test periods, then discarded because of poor yielding ability. (Sprague & Eberhart, 1977). This article refers to a report that visual selection practiced during inbreeding had little, if any, direct influence on yield in hybrid combinations. However, selection was effective for some other traits, e.g., maturity. Recurrent selection was somewhat more effective in improving breeding populations.

These failures to substantially alter plant characteristics are costly. Even the successes with recurrent selection may generally be described as incremental and long range improvements rather than mercurial saltatory jumps. Divergence of corn varieties for oil and protein content of grain was achieved if results over the 70 year history of a long-term study in Illinois are considered. However, improvement in yield has been less dramatic. Over the past 60 years, increases in yield due to genetic improvement have averaged only about one bushel/acre/year (Hallauer et al., 1988). Only a small population of hybrid plants produced commercially ever show enough improvement to be worth marketing. World-wide needs for plant derived food, both for animals and humans, warrant improved strategies. Plants are also finding uses in non-food products necessitating increased production. New methods are necessary for more efficient and successful plant breeding programs than are currently available.

Recent advances in molecular biology have expanded man's ability to manipulate the germplasm of animals and plants. Genes controlling specific phenotypes, for example specific polypeptides that lend antibiotic or herbicide resistance, have been located within certain germplasm and isolated from it. Even more important has been the ability to take the genes which have been isolated from one organism and to introduce them into another organism. This transformation may be accomplished even where the recipient organism is from a different phylum, genus or species from that which donated the gene (heterologous transformation).

Attempts have been made to genetically engineer desired traits into plant genomes by introduction of exogenous genes. These techniques have been successfully applied in some plant systems, principally in dicotyledonous species. The uptake of new DNA by recipient plant cells has been accomplished by various means, including Agrobacterium infection (Nester et al., 1984), polyethylene glycol (PEG)-mediated DNA uptake (Lorz et al., 1985), electroporation of protoplasts (Fromm et al., 1986) and microprojectile bombardment (Klein et al., 1987). Unfortunately, the introduction of exogenous DNA into monocotyledonous species and subsequent regeneration of transformed plants has proven much more difficult than transformation and regeneration in dicotyledonous plants. However, techniques are now available for transformation of barley (Wan & Lemaux, 1994), wheat (Weeks et al., 1993), corn (Gordon-Kamm et al., 1990), and sorghum (Casas et al., 1993). The availability of these transformation techniques suggests that it may now be possible to address improvement of agronomic performance of a crop plant through the techniques of genetic engineering.

With the advent of genetic engineering techniques that are new opportunities for increasing yield in crops. One of the goals of this technology is to introduce genes into a crop that will increase yield and/or stabilize yield across multiple environments. However, no genetic elements that contribute to important agronomic characteristics, such as yield, have been identified and introduced into crops using the techniques of genetic engineering.

The enzyme phosphinothricin acetyl transferase (PAT) inactivates the active ingredient in the herbicides bialaphos or phosphinothricin (PPT). PPT inhibits glutamine synthetase, (Murakami et al., 1986; Twell et al., 1989) causing rapid accumulation of ammonia and cell death. Genes that encode the enzyme phosphinothricin acetyltransferase are obtainable from species of Streptomyces (e.g., ATCC No. 21,705) and include the bar gene from *Streptomyces hygroscopicus* or the pat gene from *Streptomyces viridochromogenes*. These organisms synthesize numerous unique compounds, secondary metabolites, that often possess antibacterial, antitumor, or antiparasitic activity (Demain et al., 1983). *Streptomyces viridochromogenes* produces a broad spectrum tripeptide antibiotic phosphinothricyl-alanyl-alanine (phosphinothricin) [2-amino-4-(methylphosphinyl)-butanoic acid] (Bayer et al., 1972). The gene that encodes for phosphinothricin resistance has been designated pat and was first isolated from *S. Viridochromogenes* and shares extensive nucleotide sequence homology with the bar gene of *S. hygroscopicus* (Murakami et al., 1986; Thompson et al., 1987). The bar gene has been well studied and serves as a model to explain the mode of action of the pat gene. The bar gene encodes a phosphinothricin acetyltransferase, which acetylates the free $NH_2$ group of phosphinothricin and thereby prevents autotoxicity in the producing organism (Murakami et al., 1986). Hence, the bar gene can be cloned to obtain resistance to the antibiotic bialaphos and can be used as a dominant selectable marker.

The bar gene has been cloned and used as a selectable marker in *E. coli* (Thompson et al., 1987) which is bialaphos sensitive (Murakami et al., 1986). The bar gene has also been expressed in tobacco, tomato, and potato plants (de Block et al., 1987; Leemans et al., 1987). The transgenic tobacco, tomato, and potato plants were completely resistant to high doses of the commercial formulations of both phosphinothricin and bialaphos (de Block et al., 1987). *S. hygroscopicus* is used for the commercial production of bialaphos (Herbiace$^R$, Meiji Seika Kaisha, Ltd., Yokohama, Japan) and is being used in agriculture as a nonselective herbicide (Thompson et al., 1987). Phosphinothricin is chemically synthesized and sold under the tradename of BastaR, Hoechst AG, Germany). Selection for bialaphos resistance can be made in the field by spraying seedlings with a 1% solution of Basta containing 200 g/L glufosinate (the ammonium salt of phosphinothricin).

The enzyme encoded by the bar gene is also involved in the bialaphos biosynthetic pathway in *S. hygroscopicus*. In addition to acetylation of phosphinothricin, the enzyme catalyzes acetylation of demethyl-phosphinothricin which is an intermediate in the biosynthetic pathway (Thompson et al., 1987). PAT, however, has no activity on any substrates other than phosphinothricin and demethyl-phosphinothricin, including no activity on the amino acid glutamate of which phosphinothricine is an analog (Thompson et al., 1987). Introduction of a gene encoding PAT into a plant would, therefore, be expected to confer resistance to the herbicide phosphinothricin on the plant, but not effect the phenotype of the plant in any other way.

SUMMARY OF THE INVENTION

The present invention relates to the surprising discovery that the introduction of a PAT gene into plants, such as corn, correlates with increased yield in the resultant plants. The invention therefore provides new methods and compositions for use in plant breeding and genetic engineering to specifically alter yield.

A transformed plant or transformed plant line is defined herein as a plant or plant line into which a DNA sequence, preferably from a source with which the recipient plant is not sexually compatible, has been introduced through the use of genetic engineering techniques.

A DNA sequence that encodes the enzyme phosphinothricin acetyl transferase (PAT) is herein defined as a "PAT gene", regardless of the source of the gene. Genes encoding PAT include the bar gene isolated from *Streptomyces hygroscopicus* and the pat gene isolated from *Streptomyces viridochromogenes*.

pat gene compositions are described in U.S. Pat. No. 5,273,894, incorporated herein by reference, which patent also describes the use of the pat gene as a resistance marker. The pat gene is further exemplified by DNA segments that include a DNA sequence as set forth herein by SEQ ID NO:1 and that encode a polypeptide that includes an amino acid sequence as set forth in SEQ ID NO:2. A pat gene sequence with modified codon usage for advantageous expression in plants is described in U.S. Pat. No. 5,276,268, incorporated herein by reference. In U.S. Pat. No. 5,276,268, the DNA sequence termed sequence III, as shown in Table III, is the sequence adapted for expression in plants. This sequence is contemplated for use in the present invention.

The bar gene is currently the preferred gene for use with the present invention. The bar gene is described in issued European Patents EP 0,242,236 and EP 0,242,246, and shown in FIG. 2 thereof. EP 0,242,246 also discloses the pat gene in FIG. 9. The bar gene is further exemplified by DNA segments that include a DNA sequence as set forth herein by SEQ ID NO:3 and that encode a polypeptide that includes an amino acid sequence as set forth in SEQ ID NO:4.

Irrespective of the source of the gene, it is preferred that the PAT gene be operatively linked to a constitutive promoter so that the promoter functions to express the gene. In a currently preferred embodiment, the gene encoding PAT is constitutively expressed by functionally linking the gene downstream of a Cauliflower Mosaic Virus (CMV) 35S promoter. A variety of other promoters and plasmid constructs could be employed, as described, for example, in U.S. Pat. Nos. 5,276,268 and 5,273,894; in European Patents EP 0,242,236 and EP 0,242,246; and in U.S. patent application Ser. No. 08/113,561.

A "PAT gene integration event DNA segment" is the result of an integration event of a gene encoding a PAT enzyme. This is more particularly defined herein as a DNA sequence encoding PAT as well as adjacent plant DNA sequences, preferably, maize DNA sequences, the function of which flanking sequences are affected by the integration of the gene encoding PAT.

Plants, plant lines or hybrids that contain a PAT gene integration event DNA segment are referred to as GR plants, GR lines, GR inbreds or GR hybrids. In particular, an integration event referred to as the B16 integration event is defined as the DNA sequence derived from pDPG165, including the bar gene, that was introduced into maize through genetic engineering techniques as well as maize DNA sequences, the function of which are affected by the integration of the bar gene in the transformant designated B16.

"Crossing" a plant to provide a plant line having an increased yield relative to a starting plant line, as disclosed herein, is defined as the techniques that result in a PAT gene being introduced into a plant line by crossing a starting line with a donor plant line that comprises a PAT gene. To achieve this one would, generally, perform the following steps:

(a) plant seeds of the first (starting line) and second (donor plant line that comprises a PAT gene) parent plants;

(b) grow the seeds of the first and second parent plants into plants that bear flowers;

(c) pollinate the female flower of the first parent plant with the pollen of the second parent plant; and (d) harvest seeds produced on the parent plant bearing the female flower.

Backcross conversion is herein defined as the process including the steps of:

(a) crossing a plant of a first genotype containing a desired gene, DNA sequence or element to a plant of a second genotype lacking said desired gene, DNA sequence or element;

(b) selecting one or more progeny plant containing the desired gene, DNA sequence or element;

(c) crossing the progeny plant to a plant of the second genotype; and (d) repeating steps (b) and (c) for the purpose of transferring said desired gene, DNA sequence or element from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking said desired DNA sequence may be referred to as an unconverted genotype, line, inbred, or hybrid.

It is contemplated that an increase in yield in PAT gene transformants may be a result of an effect of PAT gene activity on plant cell metabolism. It is know that phosphinothricin is an analog of the amino acid glutamate. Furthermore, it is known in plants that inorganic nitrogen is first assimilated into the amino acids glutamate and glutamine and subsequently into aspartate and asparagine and that these amino acids served as a nitrogen reservoir for the plant. It is proposed that the activity of the PAT gene may effect nitrogen metabolism in the plant through acetylation of one or more of these amino acids, or perhaps other compounds, and, therefore, PAT gene activity may effect nitrogen metabolism in the plant cell through the assimilation of inorganic nitrogen into organic compounds. It is contemplated that this alteration in nitrogen assimilation may contribute to increased plant vigor and be further manifested in increased yield.

However, irrespective of the underlying mechanism, the present invention provides methods for increasing the yield of a crop plant that are clearly useful. The invention in one embodiment provides a method for increasing yield of a crop plant that comprises stable transformation of a plant with a DNA sequence that encodes the enzyme phosphinothricin acetyltransferase (PAT). In a preferred embodiment the plant is *Zea mays*.

In a further embodiment of the present invention, the DNA sequence comprising a PAT gene and adjacent plant genomic DNA sequences is transferred from a PAT gene transformed donor plant to a recipient plant whereby the yield of the recipient plant is increased following introduction of the PAT gene-flanking sequence DNA segment. The DNA sequence is further transferred to other genotypes through the process of backcross conversion and the yield of said backcross converted plants, or hybrids derived therefrom, is increased relative to the unconverted plant.

It is contemplated that increased yield in lines derived by the B16 transformant may be due to the B16 integration event itself. It is proposed that integration of pDP165 DNA sequences in the B16 transformant inactivated a maize genomic DNA sequence that in the untransformed maize plant contributes to a decrease in yield. For example, plasmid DNA sequences may have integrated into and disrupted a gene that encodes a protein that limits yield and in the absence of the expression of said disrupted gene there is an observed increase in yield. Alternatively, the DNA integration event in B16 may have effected the maize genome in such a manner that the activity of a yield enhancing element is increased with a resultant increase in yield. Defining the precise mechanism(s) that operate, although of scientific interest, is not necessary to the practice of the invention.

In another embodiment of the present invention, an integration event of the bar gene in maize, designated B-3-14-7, or alternatively designated B-3-14-4 or E2 or E5 or E2/E5 or B01C16 or B16, increases grain yield when said integration event is introgressed into lines of maize by backcross conversion, including, but not limited to hybrids.

In another embodiment of the present invention, the flanking maize genomic DNA sequences that are situated adjacent to pDPG165 derived DNA sequences in a PAT gene integration event are isolated. Said flanking DNA sequences are employed to identify and clone the maize genomic DNA sequence into which pDPG165 sequences were integrated in the integration event.

In a further embodiment of the present invention, the pDPG165 derived sequences and maize DNA sequences into which pDPG165 was inserted in the integration event are used as a genetic marker in marker assisted breeding for purposes of selecting maize plants with increased yield based on the presence of said pDPG165 or maize DNA sequences into which pDPG165 integrated without having to grow said plants and assay directly for yield. In a preferred embodiment, said integration event is a PAT gene integration event in *Zea mays* and more particularly is the bar gene integration event in transformant B16.

BRIEF DESCRIPTION OF THE DRAWINGS

FIG. 4. Field design for analysis of eight hybrids into which a PAT encoding integration event has been introgressed.

DESCRIPTION OF THE PREFERRED EMBODIMENTS

Figure 1A:
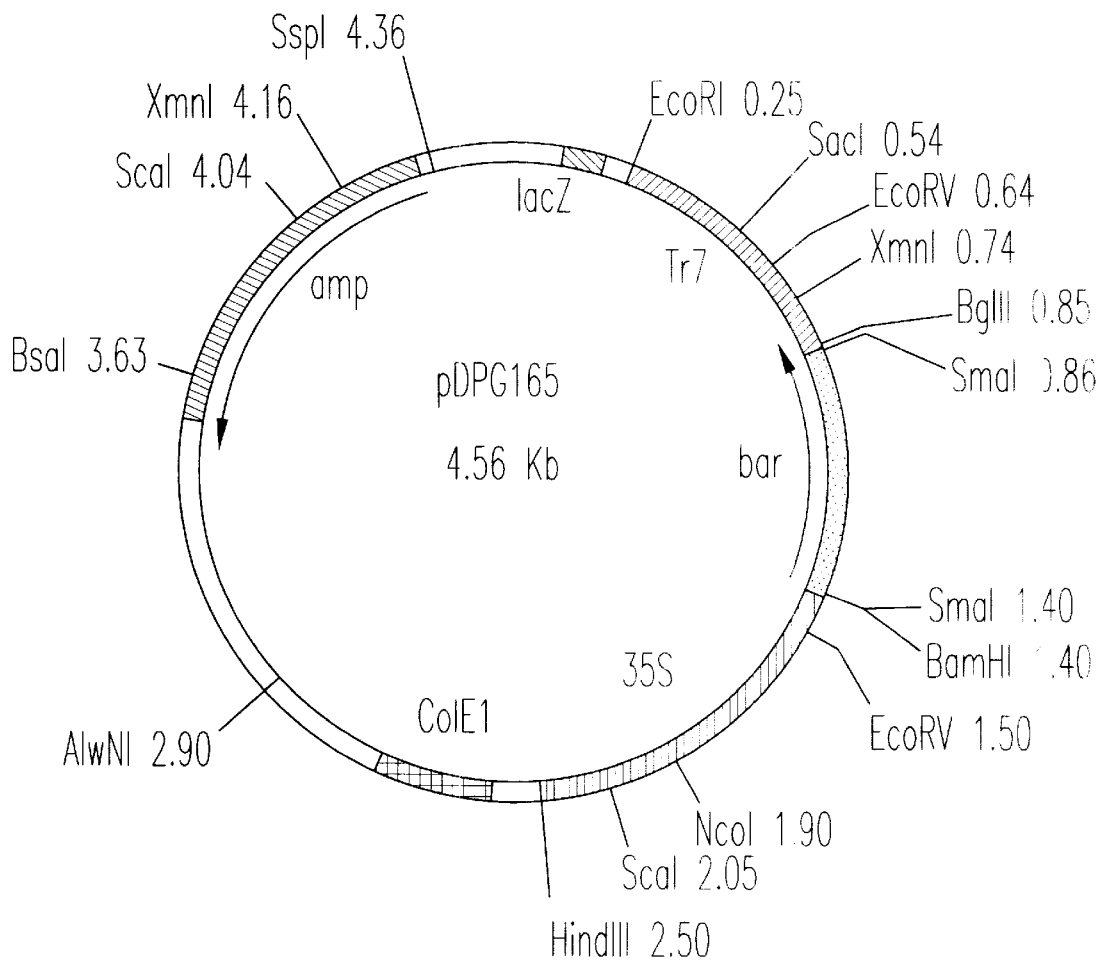
FIG. 1A. Map of plasmid pDPG165 containing the bar gene.

It is contemplated that in order to practice the present invention it is necessary to introduce a gene encoding phosphinothricin acetyltransferase into a plant species and regenerate transgenic plants. Furthermore, in those species which are reproduced by sexual methods, it is contemplated that fertile transgenic plants will be regenerated. However, as some crop species are commonly propagated by asexual means, e.g., potatoes and sugarcane, it is contemplated that the practice of the present invention will not require regeneration of fertile plants. Practice of the invention only requires that a transgenic plant containing the PAT gene be produced and that at be possible to multiply said plant either by sexual or asexual means.

It is believed that introduction of the PAT gene into any plant will lead to an increase in yield of the desired agricultural product. It is well known that a large number of dicotyledonous species may be transformed via *Agrobacterium tumefaciens* and that in recent years the applicability of particle bombardment to transformation of monocotyledonous species has been demonstrated. The examples that follow exemplify methods that may be used to produce stable transformants of maize containing the PAT gene. It is understood, however, that this invention is not limited to transformants generated by the methods disclosed herein, but may be practiced following introduction of a PAT gene into plants using any method of transformation.

EXAMPLE I

Transformation of Cultured Embryogenic Maize Cells

It is contemplated that cultured embryogenic maize cells are one of many possible targets for introduction of a gene encoding PAT. Methods for introducing DNA elements into cultured maize cells via particle bombardment are described in U.S. patent application Ser. No. 07/974,379 (incorporated herein by reference) and Gordon-Kamm et al. (1990), and further described as follows.

A. Recipient Cells

Tissue culture requires media and controlled environments. "Media" refers to the numerous nutrient mixtures that are used to grow cells in vitro, that is, outside of the intact living organism. The medium is usually a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. Rate of cell growth will also vary among cultures initiated with the array of media that permit growth of that cell type.

Nutrient media is prepared as a liquid, but this may be solidified by adding the liquid to materials capable of providing a solid support. Agar is most commonly used for this purpose. Bactoagar®, Hazelton agar, Gelrite®, and Gelgro® are specific types of solid support that are suitable for growth of plant cells in tissue culture.

Some cell types will grow and divide either in liquid suspension or on solid media. As disclosed herein, maize cells will grow in suspension or on solid medium, but regeneration of plants from suspension cultures requires transfer from liquid to solid media at some point in development. The type and extent of differentiation of cells in culture will be affected not only by the type of media used and by the environment, for example pH, but also by whether media is solid or liquid. Table 1 illustrates the composition of various media useful for creation of recipient cells and for plant regeneration.

B. Culturing Cells to be Recipients for Transformation

The studies described below set forth techniques which have been successfully applied by the inventors to generate transformable and regenerable cultures of maize cells. A variety of different types of media have been developed by the inventors and employed in carrying out various aspects of the invention. The following table, Table 1, sets forth the composition of the media preferred by the inventors for carrying out these aspects of the invention.

TABLE 1

Illustrative Embodiments of Tissue Culture Media Which are Used for Type II Callus Development, Development of Suspension Cultures and Regeneration of Plant Cells (Specifically Maize Cells)

| MEDIA NO. | BASAL MEDIUM | SUCROSE | pH | OTHER COMPONENTS** (Amount/L) |
|---|---|---|---|---|
| 52 | MS | 2% | 6.0 | .25 mg thiamine<br>1 mg 2,4-D<br>$10^{-7}$M ABA<br>Bactoagar ® |
| 101 | MS | 3% | 6.0 | MS vitatnins<br>100 mg myo-inositol<br>Bactoagar ® |
| 142 | MS | 6% | 6.0 | MS vitamins<br>5 mg BAP<br>0.186 mg NAA<br>0.175 mg IAA<br>0.403 mg 2IP<br>Bactoagar ® |
| 171 | MS | 3% | 6.0 | MS vitamins<br>.25 mg 2,4-D<br>10 mg BAP<br>100 mg myo-inositol<br>Bactoagar ® |
| 173 | MS | 6% | 6.0 | MS vitamins<br>5 mg BAP<br>.186 mg NAA<br>.175 mg IAA<br>.403 mg 2IP<br>$10^{-7}$M ABA<br>200 mg myo-inositol<br>Bactoagar ® |
| 177 | MS | 3% | 6.0 | MS vitamins<br>.25 mg 2,4-D<br>10 mg BAP<br>$10^{-7}$M ABA<br>100 mg myo-inositol<br>Bactoagar ® |
| 178 | MS | 5.8 | — | MS vitamins<br>1 mg BAP<br>1 mg NAA<br>$10^{-7}$M ABA<br>Bactoagar ® |

TABLE 1-continued

Illustrative Embodiments of Tissue Culture Media Which are Used for Type II Callus Development, Development of Suspension Cultures and Regeneration of Plant Cells (Specifically Maize Cells)

| MEDIA NO. | BASAL MEDIUM | SUCROSE | pH | OTHER COMPONENTS** (Amount/L) |
|---|---|---|---|---|
| 189 | MS | — | 5.8 | 3 mg BAP<br>0.04 mg NAA<br>0.5 mg niacin<br>800 mg L-asparagine<br>100 mg casamino acids<br>20 g sorbitol<br>1.4 g L-proline<br>100 mg myo-inositol<br>Gelgro ® |
| 201 | N6 | 2% | 5.8 | N6 vitamins<br>2 mg L-glycine<br>1 mg 2,4-D<br>100 mg casein hydrolysate<br>2.9 g L-proline<br>Gelgro ® |
| 205 | N6 | 2% | 5.8 | N6 vitamins<br>2 mg L-glycine<br>.5 mg 2,4-D<br>100 mg casein hydrolysate<br>2.9 g L-proline<br>Gelgro ® |
| 209 | N6 | 6% | 5.8 | N6 vitamins<br>2 mg L-glycine<br>100 mg casein hydrolysate<br>0.69 g L-proline<br>Bactoagar ® |
| 223 | N6 | 2% | 5.8 | 3.3 mg dicamba<br>1 mg thiamine<br>.5 mg niacin<br>800 mg L-asparagine<br>100 mg casein hydrolysate<br>100 mg myoinositol<br>1.4 g L-proline<br>3 mg bialaphos<br>Gelgro ®**** |
| 227 | N6 | 2% | 5.8 | N6 vitamins<br>2 mg L-glycine<br>13.2 mg dicamba<br>100 mg casein hydrolysate<br>2.9 g L-proline<br>Gelgro ® |
| 279 | N6 | 2% | 5.8 | 3.3 mg dicamba<br>1 mg thiamine<br>.5 mg niacin<br>800 mg L-asparagine<br>100 mg casein hydrolysate<br>100 mg myoinositol<br>1.4 g L-proline<br>Gelgro ®**** |
| 401 | MS | 3% | 6.0 | 3.73 mg $Na_2EDTA$<br>.25 mg thiamine<br>1 mg 2,4-D<br>2 mg NAA<br>200 mg casein hydrolysate<br>500 mg $K_2SO_4$<br>400 mg $KH_2PO_4$<br>100 mg myo-inositol |
| 402 | MS | 3% | 6.0 | 3.73 mg $Na_2EDTA$<br>.25 mg thiamine<br>1 mg 2,4-D<br>200 mg casein hydrolysate<br>2.9 g L-proline<br>500 mg $K_2SO_4$<br>400 mg $KH_2PO_4$<br>100 mg myo-inositol |
| 409 | MS | 3% | 6.0 | 3.73 mg $Na_2EDTA$<br>.25 mg thiamine<br>9.9 mg dicamba<br>200 mg casein hydrolysate<br>2.9 g L-praline<br>500 mg $K_2SO_4$<br>400 mg $KH_2PO_4$<br>100 mg myo-inositol |
| 425 | MS | 3% | 6.0 | 3.73 mg $Na_2EDTA$<br>.25 mg thiamine<br>9.9 mg dicamba<br>200 mg casein hydrolysate<br>2.9 g L-proline<br>500 mg $K_2SO_4$<br>400 mg $KH_2PO_4$<br>100 mg myo-inositol<br>3 mg bialaphos |
| 431 | MS | 3% | 6.0 | 3.73 mg $Na_2EDTA$<br>.25 mg thiamine<br>9.9 mg dicamba<br>200 mg casein hydrolysate<br>2.9 g L-proline<br>500 mg $K_2SO_4$<br>400 mg $KH_2PO_4$<br>100 mg myo-inositol<br>200 mOsm sorbitol |
| 501 | Clark's Medium*** | 2% | 5.7 | |
| 607 | 1/2 × MS | 3% | 5.8 | 1 mg thiamine<br>1 mg niacin<br>Gelrite ® |
| 734 | N6 | 2% | 5.8 | N6 vitamins<br>2 mg L-giycine<br>1.5 mg 2,4-D<br>0.7 g Fe sequestrene<br>200 mg casein hydrolysate<br>0.69 g L-proline<br>Gelrite ® |
| 735 | N6 | 2% | 5.8 | 1 mg 2,4-D<br>.5 mg niacin<br>.91 g L-asparagine<br>100 mg myo-inositol<br>1 mg thiamine<br>.5 g MES<br>.75 g $MgCl_2$<br>100 mg casein hydrolysate<br>0.69 g L-proline<br>Gelgro ® |

TABLE 1-continued

Illustrative Embodiments of Tissue Culture Media Which are Used for Type II Callus Development, Development of Suspension Cultures and Regeneration of Plant Cells (Specifically Maize Cells)

| MEDIA NO. | BASAL MEDIUM | SUCROSE | pH | OTHER COMPONENTS** (Amount/L) |
|---|---|---|---|---|
| 739 | N6 | 2% | 5.8 | 1 mg 2,4-D<br>.5 mg niacin<br>.91 g L-asparagine<br>100 mg myo-inositol<br>1 mg thiamine<br>.5 g MES<br>.75 g MgCl$_2$<br>100 mg casein hydrolysate<br>0.69 g L-proline<br>1 mg bialaphos<br>Gelgro ® |
| 750 | N6 | 2% | 5.8 | 1 mg 2,4-D<br>.5 mg niacin<br>.91 g L-asparagine<br>100 mg myo-inositol<br>1 mg thiamine<br>.5 g MES<br>.75 g MgCl$_2$<br>100 mg casein hydrolysate<br>0.69 g L-proline<br>0.2 M mannitol<br>1 mg bialaphos<br>Gelgro ® |
| 758 | N6 | 2% | 5.8 | 1 mg 2,4-D<br>.5 mg niacin<br>.91 g L-asparagine<br>100 mg myo-inositol<br>1 mg thiamine<br>.5 g MES<br>.75 g MgCl$_2$<br>100 mg casein hydrolysate<br>0.69 g L-proline<br>3 mg bialaphos<br>Gelgro ® |
| 2004 | N6 | 3% | 5.8 | 1 mg thiamine<br>0.5 mg niacin<br>3.3 mg dicamba<br>17 mg AgNO$_3$<br>1.4 g L-proline<br>0.8 g L-asparagine<br>100 mg casein hydrolysate<br>100 mg myo-inositol<br>Gelrite ® |
| 2008 | N6 | 3% | 5.8 | 1 mg thiamine<br>0.5 mg niacin<br>3.3 mg dicamba<br>1.4 g L-proline<br>0.8 g L-asparagine<br>Geirite ® |

*Basic MS medium described in Murashige & Skoog (1962). This medium is typically modified by decreasing the NH$_4$NO$_3$ from 1.64 g/l to 1.55 g/l, and omitting the pyridoxine HCl, nicotinic acid, myo-inositol and glycine.
**NAA = Napthol Acetic Acid
IAA = Indole Acetic Acid
2-IP = 2, isopentyl adenine
2,4-D = 2,4-Dichlorophenoxyacetic Acid
BAP = 6-benzyl aminopurine
ABA = abscisic acid
***Basic medium described in Clark (1982)
****These media may be made with or without solidifying agent.

Initiation of the Suspension Culture (A188×B73) 82 (designated SC82) for Use in Transformation c This Example describes the development of a cell line employed in various of the transformation studies set forth below, termed SC82. In the development of SC82, inoculum for suspension culture initiation was visually selected from a Type II callus that was initiated from A188 x B73 immature embryos plated on a N6-based medium containing 13.2 mg/l dicamba (227, Table 1). The suspension culture was initiated within three months of initiation of the Type II callus. Small amounts (50 to 100 mg) of callus, distinguishable by visual inspection because of its highly proembryonic morphology, were isolated from more mature or organized structures and inoculated into a 50 ml flask containing 5 mls of filter-sterilized conditioned medium from the various G(A188 x B73) 716 suspension cultures (402 medium with four types of capsule treatments and 409 medium).

After one week, this 5 ml culture was sieved through a 710 micron mesh and used to inoculate 20 mls of corresponding fresh and filter-sterilized conditioned medium from the established G(A188 x B73) 716 cultures in 150 ml flasks. After one week or more of growth, two mls of packed cells were subcultured to fresh media by the method described above. The suspension culture maintained on 409 by this method was then cryopreserved within three months. The original cell line, which was maintained on 409 (not a reinoculated cryopreserved culture), was used in Studies 1 and 2 months later which resulted in stable transformation and selection.

D. Initiation and Maintenance of Cell Line AT824

This example describes the initiation and maintenance of cell line AT824 which has been used routinely for transformation studies. Immature embryos (0.5 to 1.0 mm) were excised from the B73-derived inbred line AT and cultured on N6 medium with 100 $\mu$M silver nitrate, 3.3 mg/L dicamba, 3% sucrose and 12 mM praline (2004). Six months after initiation Type I callus was transferred to medium 2008. Two months later Type I callus was transferred to a medium with a lower concentration of sucrose (279). A sector of Type II callus was identified 17 months later and was transferred to 279 medium. This cell line was uniform in nature, unorganized, rapid growing, and embryogenic. This culture was desirable in the context of this invention as it was easily adaptable to culture in liquid or on solid medium.

The first suspension cultures of AT824 were initiated 31 months after culture initiation. Suspension cultures may be initiated in a variety of culture media including media containing 2,4-D as well as dicamba as the auxin source, e.g., media designated 210, 401, 409, 279. Cultures are maintained by transfer of approximately 2 ml packed cell volume to 20 ml fresh culture medium at 3½ day intervals. AT824 can be routinely transferred between liquid and solid culture media with no effect on growth or morphology.

Suspension cultures of AT824 were initially cryopreserved 33 to 37 months after culture initiation. The survival rate of this culture was improved when it was cryopreserved following three months in suspension culture. AT824 suspension cultures have been cryopreserved and reinitiated from cryopreservation at regular intervals since the initial date of freezing. Repeated cycles of freezing have not affected the growth or transformability of this culture.

E. Preferred Methods of Delivering DNA to Cells

There are several potential cellular targets for DNA delivery to produce fertile transgenic plants: pollen, microspores, meristems, immature embryos and cultured embryogenic cells are but a few examples.

Microprojectile bombardment is now recognized as a routine technique for introduction of exogenous DNA into plant cells. The details of this technique and its use to introduce exogerous DNA into various plant cells are discussed in Wang et al. (1988); Wan & Lemaux (1994); Weeks et al. (1993); Casas et al. (1993); Gordon-Kamm et al. (1990); Christou et al. (1991) and Christou et al. (1988). One method of determining the efficiency of DNA delivery into the cells via microprojectile bombardment employs detection of transient expression of the enzyme β-glucuronidase (GUS) in bombarded cells. For this method, plant cells are bombarded with a DNA construct which directs the synthesis of the GUS enzyme.

Apparati are available which perform microprojectile bombardment. A commercially available source is an apparatus made by Biolistics, Inc. (now DuPont), but other microprojectile or acceleration methods are within the scope of this invention. Of course, other "gene guns" may be used to introduce DNA into cells.

Several modifications of the microprojectile bombardment method were made by the inventors. For example, stainless steel mesh screens were introduced below the stop plate of the bombardment apparatus, i.e., between the gun and the cells. Furthermore, modifications to existing techniques were developed by the inventors for precipitating DNA onto the microprojectiles.

Another newly emerging technique for the introduction of DNA into plant cells is electroporation of intact cells. The details of this technique are described in Krzyzek and Laursen (PCT publication WO 92/12250). Similar to particle bombardment, the efficiency of DNA delivery into cells by electroporation can be determined by using the β-glucuronidase gene. The method of electroporation of intact cells and by extension intact tissues, e.g., immature embryos, was developed by Krzyzek and Laursen and represents improvements over published procedures. Generation of fertile plants using these techniques were described by Spencer et al. (Spencer et al., 1994) and Laursen et al. (1994).

It is contemplated that other methods may also be used for introduction of DNA into plant cells.

F. Microprojectile Bombardment

For bombardment, friable, embryogenic Type-II callus (Armstrong & Green, 1985) was initiated from immature embryos essentially as set forth above. The callus was initiated and maintained on N6 medium (Chu et al., 1975) containing 2 mg/l glycine, 2.9 g/l L-proline, 100 mg/l casein hydrolysate, 13.2 mg/l dicamba or 1 mg/l 2,4-D, 20 g/l sucrose, pH 5.8, solidified with 2 g/l Gelgro® (ICN Biochemicals). Suspension cultures initiated from these callus cultures were used for bombardment.

In the case of SC82, suspension culture SC82 was initiated from Type-II callus maintained in culture for three months. SC82 cells were grown in liquid medium for approximately four months prior to bombardment. SC82 cells were also cryopreserved five months after suspension culture initiation, stored frozen for five months, thawed and used for bombardment.

Prior to bombardment, recently subcultured suspension culture cells were sieved through 1000 μm stainless steel mesh. From the fraction of cell clusters passing through the sieve, approximately 0.5 ml packed cell volume (PCV) were pipetted onto 5 cm filters (Whatman #4) and vacuum-filtered in a Buchner funnel. The filters were transferred to petri dishes containing three 7 cm filters (Whatman #4) moistened with 2.5 ml suspension culture medium.

The dish containing the filters with the suspension cells was positioned 6 cm below the lexan plate used to stop the nylon microprojectile. With respect to the DNA, when more than a single plasmid was used, plasmid DNA was precipitated in an equimolar ratio onto tungsten particles (average diameter approximately 1.2 μm, GTE Sylvania) using a modification of the protocol described by Klein et al., (1987). In the modified procedure, tungsten was incubated in ethanol at 65° C. for 12 hours prior to being used for precipitation. The precipitation mixture included 1.25 mg tungsten particles, 25 μg plasmid DNA, 1.1 M $CaCl_2$ and 8.7 mM spermidine in a total volume of 575 μl. After adding the components in the above order, the mixture was vortexed at 4° C. for 10 minutes, centrifuged (500×G) for 5 minutes and 550 μl of supernatant was decanted. From the remaining 25 μl of suspension, a 1 μl aliquot was pipetted onto the microprojectile for bombardment.

Each plate of suspension cells was bombarded twice at a vacuum of 28 inches Hg. In bombarding the embryogenic suspensions of A188 X B73, 100 μm or 1000 μm stainless steel screens were placed about 2.5 cm below the stop plate in order to increase the number of foci while decreasing their size and also to ameliorate injury to the bombarded tissue. After bombardment, the suspension cells and the supporting filter were transferred onto solid medium or the cells were scraped from the filter and resuspended in liquid culture medium.

Figure 1B:
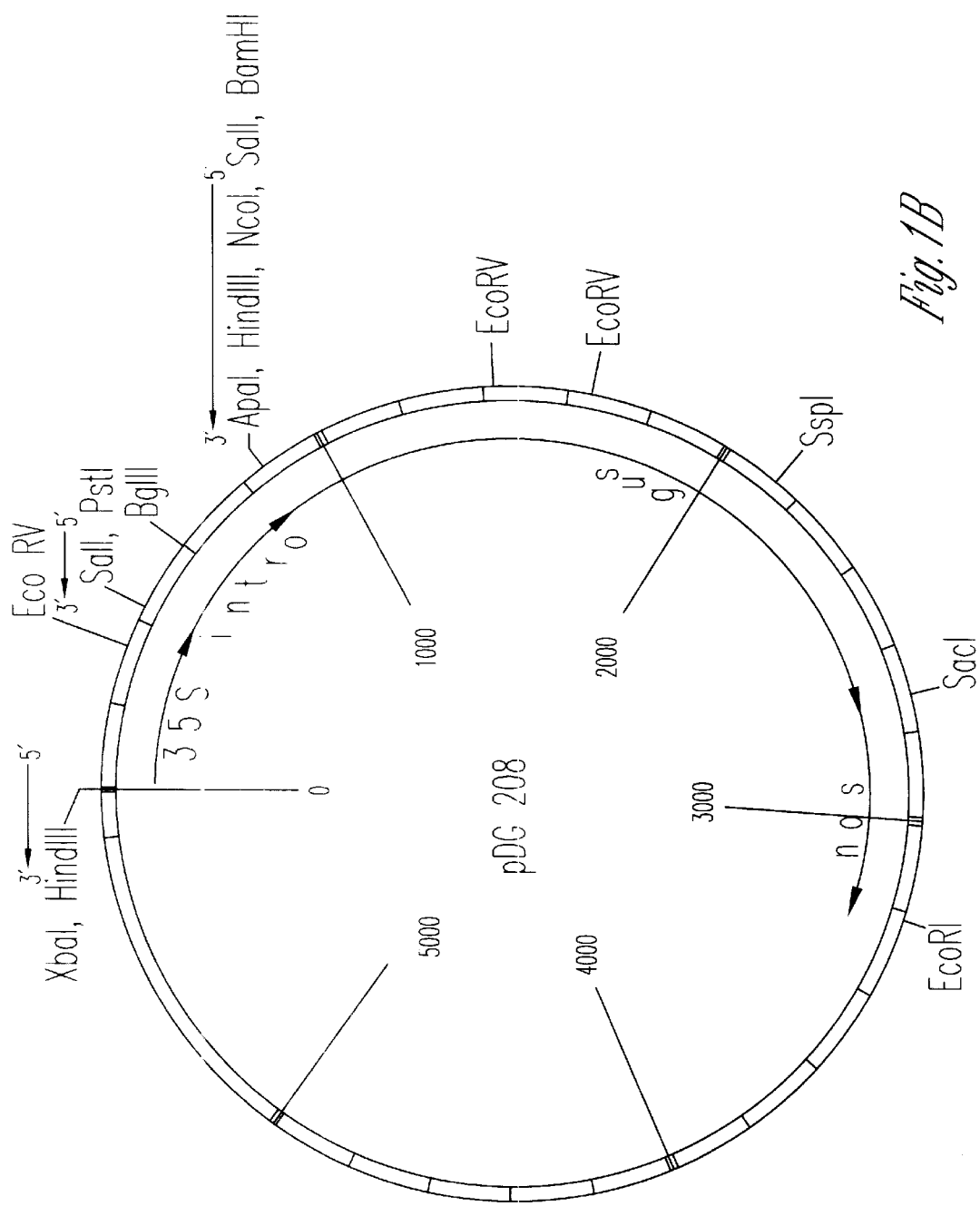
FIG. 1B. Map of plasmid pDPG208 containing the uidA gene.
Figure 1C:
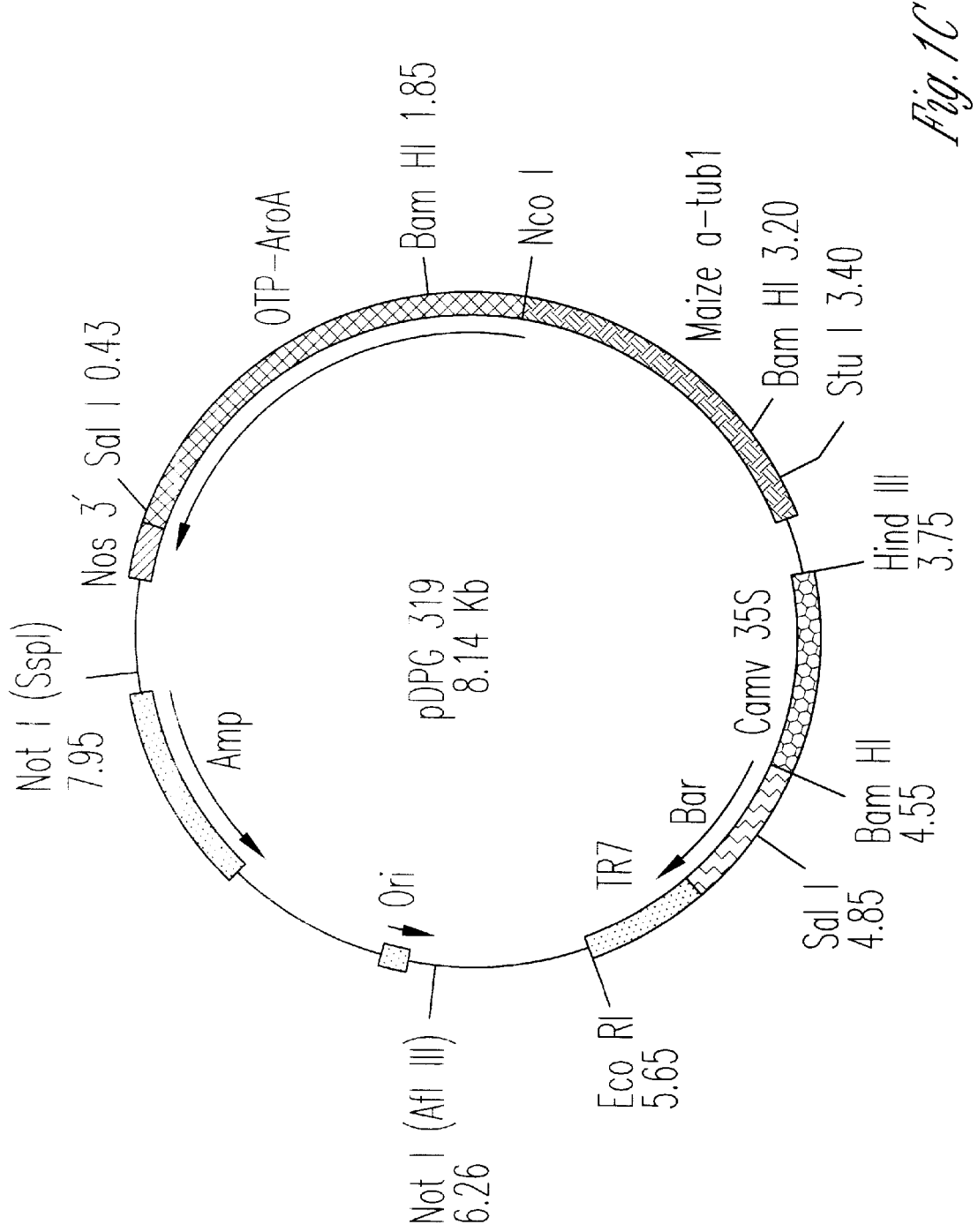
FIG. 1C. Map of plasmld pDPG319 containing the aroA gene and the α-tubulin promoter in addition to the bar expression cassette derived from pDPG165.
Figure 1D:
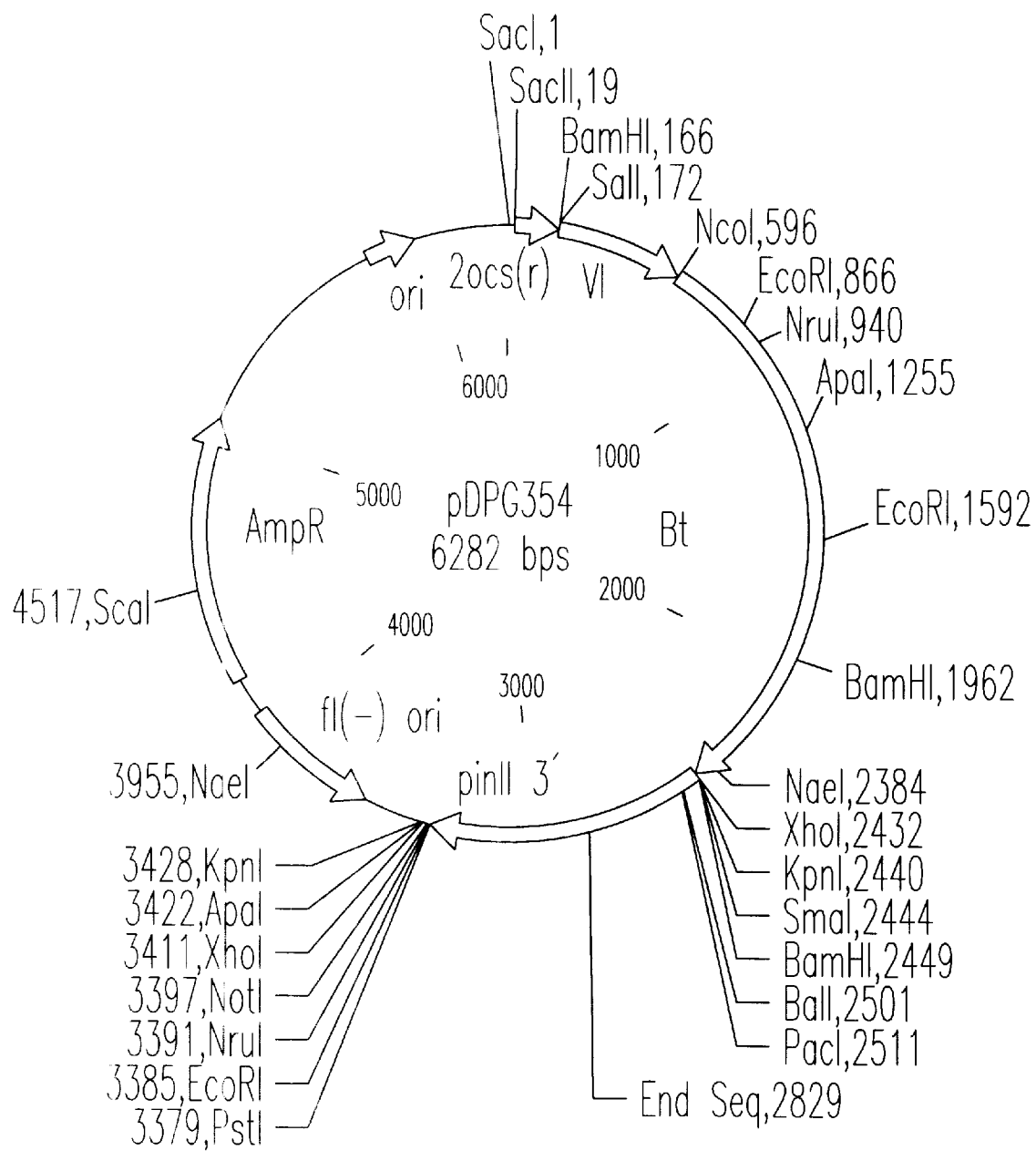
FIG. 1D. Map of plasmid pDPG354 containing a synthetic Bt gene.
Figure 1E:
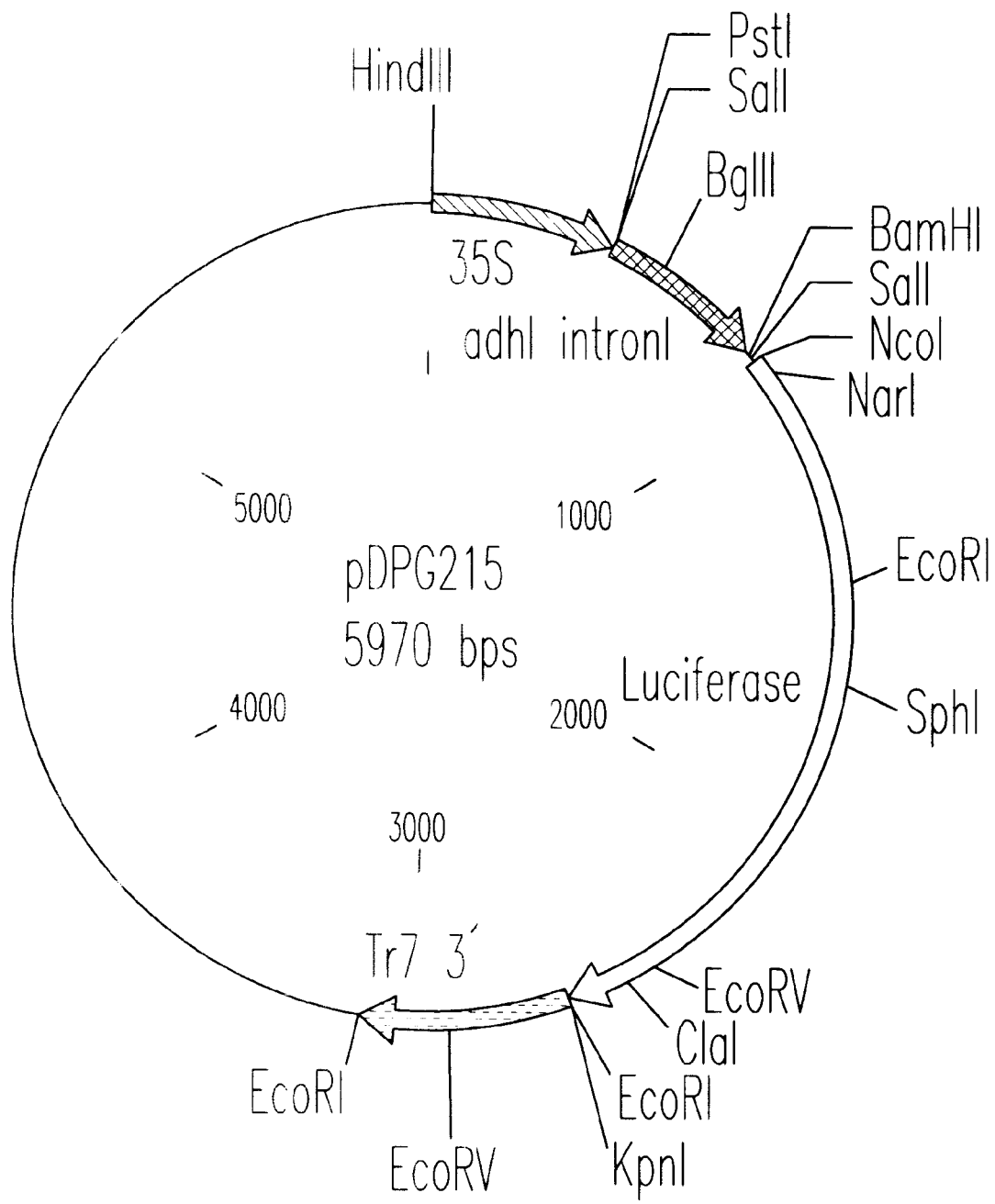
FIG. 1E. Map of plasmid pDPG215 containing a luciferase gene.
Figure 1F:
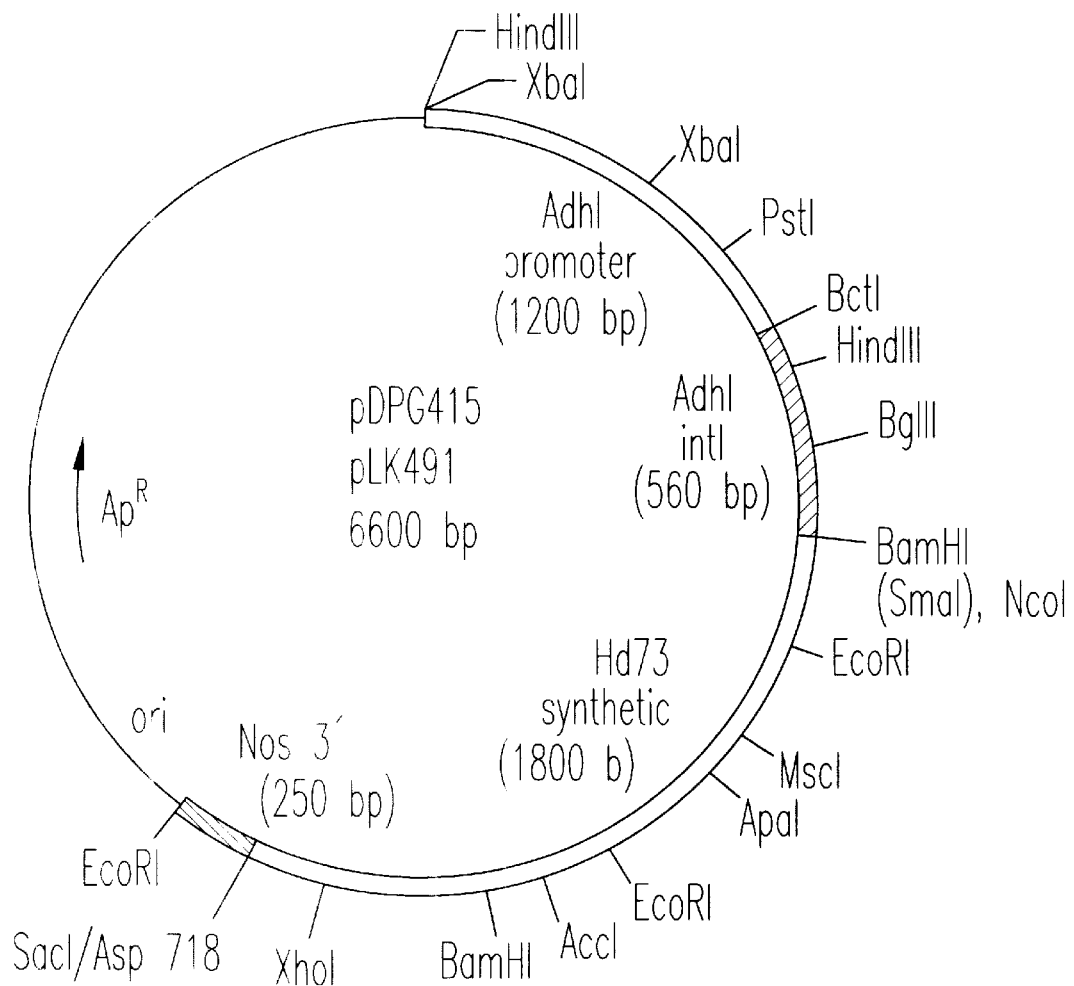
FIG. 1F. Map of plasmid pDPG415 containing a synthetic Bt gene.
Figure 1G:
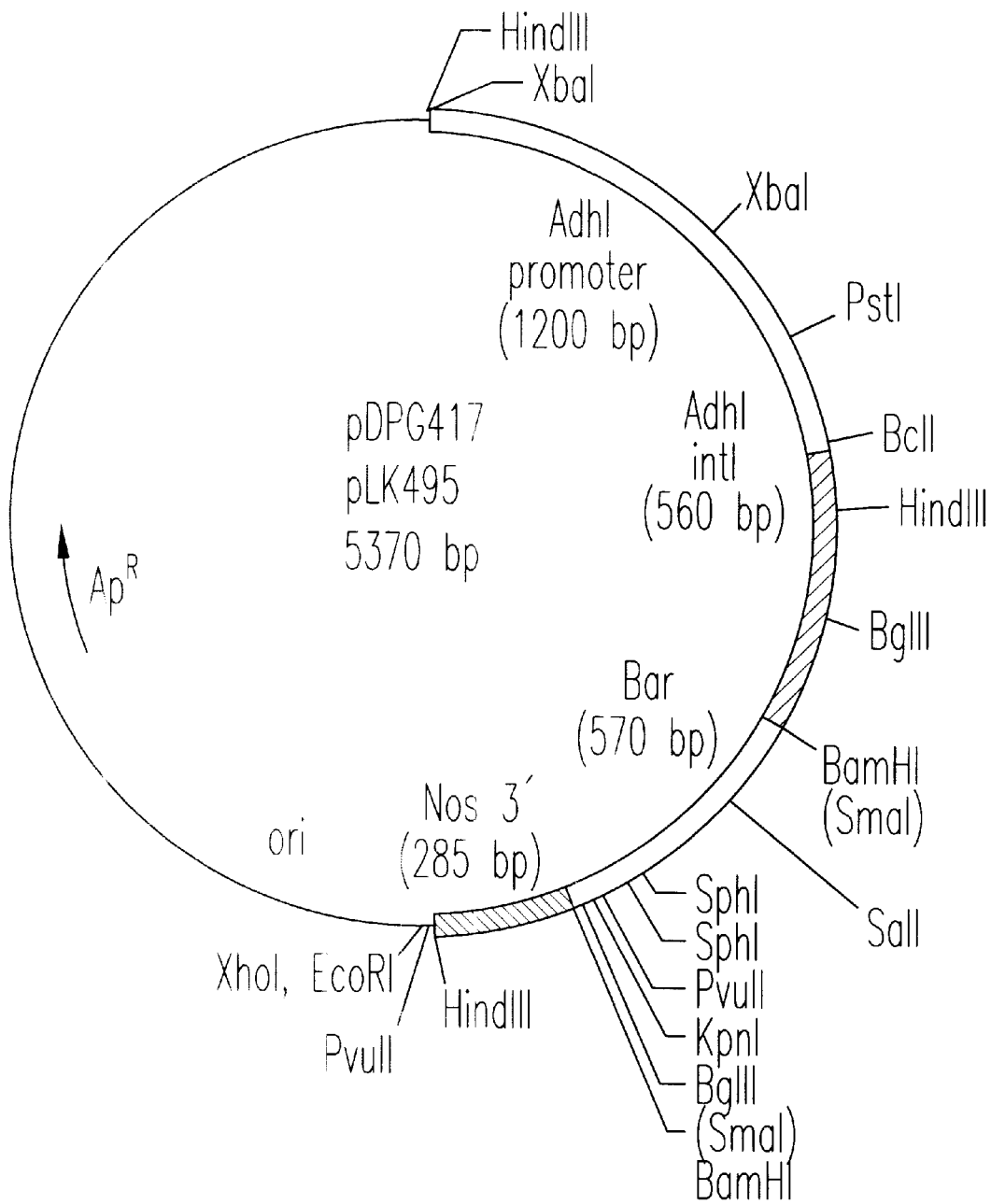
FIG. 1G. Map of plasmid pDPG417 containing a bar gene.
Figure 1H:
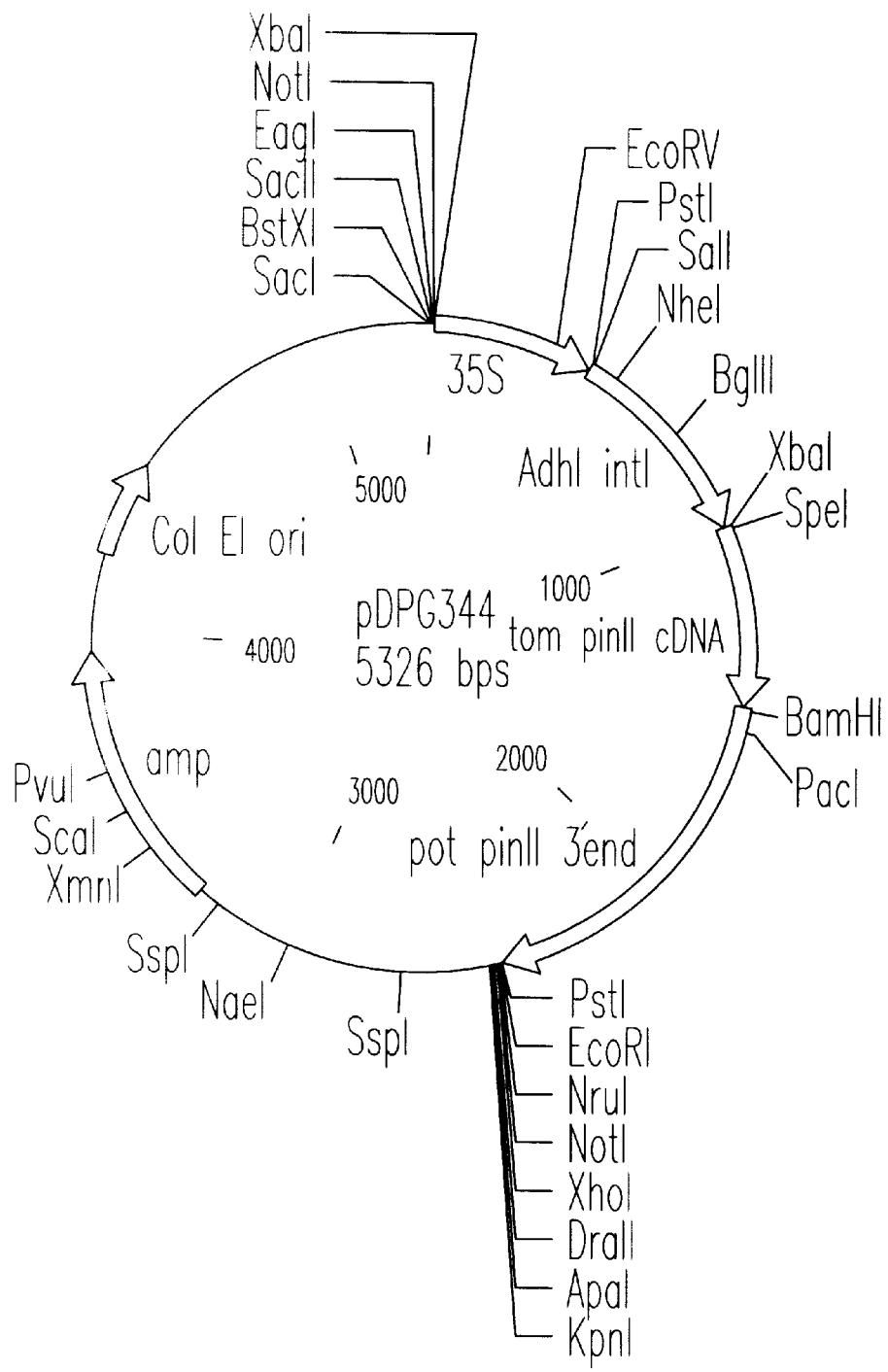
FIG. 1H. Map of plasmid pDPG344 containing the proteinase inhibitor II gene from tomato.

Cells from embryogenic suspension cultures of maize were bombarded with the bar-containing plasmid pDPG165 (FIG. 1A) alone or in combination with a plasmid encoding GUS, pDPG208 (FIG. 1B). In studies in which a GUS plasmid was included, two of the filters containing bombarded cells were histochemically stained 48 h post-bombardment. The total number of foci (clusters of cells) per filter transiently expressing GUS was at least 1000. In two separate studies designed to quantitate transiently expressing cells (using an SC82 (A188 x B73) suspension culture), the mean number of GUJS-staining foci per filter was 1472 and 2930. The number of cells in individual foci that expressed GUS averaged 2 to 3 (range 1 to 10). Although histachemical staining can be used to detect cells transformed with the gene encoding GUS, those cells will no longer grow and divide after staining. For detecting stable transformants and growing them further, e.g., into plants, selective systems compatible with viability are required.

G. Microprojectile Bombardment—AT824

Suspension culture AT824 was subcultured-to fresh medium 409 two days prior to particle bombardment. Cells were plated on solid 409 medium 16 to 24 hours before bombardment (about 0.5 ml packed cell volume per filter). Tissue was treated with 409 medium containing 200 mOsm sorbitol (medium 431) for one hour prior to bombardment.

DNA was introduced into cells using the DuPont Biolistics PDS1000He particle bombardment device.

DNA was precipitated onto gold particles as follows. A stock solution of gold particles was prepared by adding 60 mg of 1 μm gold particles to 1000 μl absolute ethanol and incubating for at least three hours at room temperature followed by storage at −20° C. Twenty to 35 μl sterile gold particles were centrifuged in a microcentrifuge for one minute. The supernatant was removed and one ml sterile water was added to the tube, followed by centrifugation at 2000 rpm for five minutes. Microprojectile particles are resuspended in 30 μl of DNA solution (30 μg total DNA) containing 10 μg each of the following vectors: pDPG165 (bar), pDPG344 (tomato proteinase inhibitor II gene), and pDPG354 (*B. thuringiensis* crystal toxin protein gene). Two hundred twenty microliters sterile water, 250 μl 2.5 M CaCl$_2$ and 50 μl spermidine were added. The mixture was thoroughly mixed and placed on ice, followed by vortexing at 4° C. for 10 minutes and centrifugation at 500 rpm for five minutes. The supernatant was removed and the pellet resuspended in 600 μl absolute ethanol. Following centrifugation at 500 rpm for five minutes the pellet was resuspended in 36 μl of absolute ethanol.

Ten μl of the particle preparation were dispensed on the surface of the flyer disk and the ethanol was allowed to dry completely. Particles were accelerated by a helium blast of approximately 1100 psi. One day following bombardment, cells were transferred to liquid medium 409 (10 ml). Tissue was subcultured twice per week. During the first week there was no selection pressure applied.

H. Further Optimization of Ballistic Transformation

This example describes the optimization of the ballistic transformation protocol. Both physical and biological parameters for bombardment have been addressed. Physical factors are those that involve manipulating the DNA/microprojectile precipitate or those that affect the flight and velocity of either the macro- or microprojectiles. Biological factors include all steps involved in manipulation of cells immediately after bombardment. The prebombardment culturing conditions, such as osmotic environment, the bombardment parameters, and the plasmid configuration have been adjusted to yield the maximum numbers of stable transformants.

Physical Parameters

Gap Distance

The variable nest (macro holder) can be adjusted to vary the distance between the rupture disk and the macroprojectile, i.e., the gap distance. This distance can be varied from 0 to 2 cm. The predicted effects of a shorter gap are an increase of velocity of both the macro- and microprojectiles, an increased shock wave (which leads to tissue splattering and increased tissue trauma), and deeper penetration of microprojectiles. Longer gap distances would have the opposite effects but may increase viability and, therefore, the total number of recovered stable transformants.

The effect of gap distance was investigated by bombarding an embryogenic suspension with pDPG208. Plates were shot in triplicate at gaps of 3, 6, 9, and 12 mm. Tissue was assayed for GUS activity and foci were counted. Using a 3 mm gap, GUS foci were the most numerous and well distributed across the filter. The gas shock wave appeared to be the greatest at this distance as shown by the degree of tissue splattering. Previous studies performed at this gap size also have shown poor tissue recovery. Gaps of 6 mm and 9 mm showed little to no tissue splattering. GUS foci were well distributed across the filter but were fewer in number than those in the 3 mm samples. Samples bombarded with a gap distance of 12 mm showed nearly equivalent numbers of GUS foci as with sample bombarded at 6 mm and 9 mm but they were located almost exclusively at the center of the filter. No tissue splattering was observed. Based on these observations, it is suggested that bombardments be conducted with a gap distance of 6 to 9 mm.

Flight Distance

The fixed nest (contained within the variable nest) can be varied between 0 and 2 cm in predetermined increments by the placement of spacer rings to adjust the flight path traversed by the macroprojectile. Short flight paths allow for greater stability of the macroprojectile in flight but reduce the overall velocity of the microprojectiles. Increased stability in flight increases the number of centered GUS foci. Greater flight distances (up to some point) increase velocity but also increase instability in flight.

The effect of the macroprojectile flight path length was investigated using E1 suspension cells. The flight distances tested were 0, 1.0, 1.5, and 2.0 cm. Samples were bombarded with pDPG208 GUS vector and were assayed 48 hours after bombardment for GUS activity. The number of GUS foci was the greatest at a flight path length of 1.0 cm and least at 0 cm. No tissue splattering was observed at 0 cm, very little at 1.0 cm, and a greater amount at 1.5 and 2.0 cm. Based on these observations, it is recommended that bombardments be done with a flight path length of 1.0 cm.

Tissue distance

Placement of tissue within the gun chamber should have significant effects on microprojectile penetration. Increasing the flight path of the microprojectiles will decrease velocity and trauma associated with the shock wave. A decrease in velocity will also result in shallower penetration of the microprojectiles.

Helium pressure

By manipulation of the type and number of rupture disks, pressure can be varied between 400 and 2000 psi within the gas acceleration tube. Optimum pressure for stable transformation has been determined to be between 1000 and 1200 psi.

Biological Parameters

Culturing conditions and other factors can influence the physiological state of the target cells and may have profound effects on transformation and integration efficiencies. First, the act of bombardment could stimulate the production of ethylene which could lead to senescence of the tissue. The addition of antiethylene compounds could increase transformation efficiencies. Second, it is proposed that certain points in the cell cycle may be more appropriate for integration of introduced DNA. Hence synchronization of cell cultures may enhance the frequency of production of transformants. Third, the degree of tissue hydration may also contribute to the amount of trauma associated with bombardment as well as the ability of the microprojectiles to penetrate cell walls.

It has also been reported that slightly plasmolyzed yeast cells allow increased transformation efficiencies (Armaleo et al., 1990). It was hypothesized that the altered osmotic state of the cells helped to reduce trauma associated with the penetration of the microprojectile. Lastly, the growth and cell cycle stage may be important with respect to transformation.

Osmotic adjustment

It has been suggested that osmotic pretreatment could potentially reduce bombardment associated injury as a result of the decreased turgor pressure of the plasmolyzed cell. Two studies were done in which E1 suspension cells were osmotically adjusted with media supplemented with sorbitol. Cells were plated onto osmotic media 24 hours prior to bombardment. The osmotic values of the media were 200, 400, and 600 mOSM/kg. Samples were bombarded with either pDPG208 (GUS) or pDPG165 (bar). GUS samples were assayed and foci were counted and plotted. Cells osmotically adjusted at 400 mOSM/kg showed an approximately 25% increase in the number of transient GUS foci. Samples bombarded with bar were selected in liquid (2 mg/l bialaphos) and thin plated on medium containing 3 mg/l bialaphos. Cells treated with 600 mOSM/kg medium grew more slowly than cells treated with media of other osmotic strengths in this study.

A second study investigated the effects of short duration osmotic adjustment at 500 mOSM/kg on both transient GUS expression and stable transformation. The rationale for the short duration of osmotic adjustment was that cells should be plasmolyzed just before bombardment, using longer time periods of pretreatment may allow the cells to adjust to the osmoticum (i.e. re-establishing turgor). The first control was bombarded (0 minutes, no new medium) followed by cells pretreated for 45 minutes and 90 minutes with 500 mOSM/kg medium with either pDPG208 or pDPG165. Since the pretreatment required media changes (i.e. fresh 500 mOSM/kg media), a set of controls was also washed using fresh medium without the osmoticum. After bombardment the cells were put onto solid medium to recover overnight followed by resuspension in liquid medium. After one week, liquid selection was started using 2 μg/ml bialaphos. Cells were plated on 3 μg/ml bialaphos at 0.1 ml PCV eleven days after bombardment. Transient GUS activity was assayed 48 hours after bombardment.

The number of cells transiently expressing GUS increased following subculture into both fresh medium and osmotically adjusted medium. Pretreatment times of 90 minutes showed higher numbers of GUS expressing foci than shorter times. Cells incubated in 500 mOSM/kg medium for 90 minutes showed an approximately 3.5-fold increase in transient GUS foci than the control.

I. Identification of Transformed Cells Using Selectable Markers

It is believed that DNA is introduced into only a small percentage of cells in any one study. In order to provide a more efficient system for identification of those cells receiving DNA and integrating it into their genomes one may desire to employ a means for selecting those cells that are stably transformed. One exemplary embodiment of such a method is to introduce into the host cell a marker gene which confers resistance to some normally inhibitory agent, e.g. an antibiotic or herbicide. The potentially transformed cells are then exposed to the agent. In the population of surviving cells are those cells wherein generally the resistance-conferring gene has been integrated and expressed at sufficient levels to permit cell survival. Cells may be tested further to confirm stable integration of the exogenous DNA. Using embryogenic suspension cultures, stable transformants are recovered at a frequency of approximately one per 1000 transiently expressing foci.

One of the difficulties in cereal transformation, e.g., corn, has been the lack of an effective selective agent for transformed cells, from totipotent cultures (Potrykus, 1989). Stable transformants were recovered from bombarded non-embryogenic Black Mexican Sweet (BMS) maize suspension culture cells, using the neo gene and selection with the aminoglycoside, kanamycin (Klein, 1989). This approach, while applicable to the present invention, is not preferred because many monocots are insensitive to high concentrations of aminoglycosides (Dekeyser et al., 1989; Hauptmann et al., 1988). The stage of cell growth, duration of exposure and concentration of the antibiotic may be critical to the successful use of aminoglycosides as selective agents to identify transformants (Lyznik et al., 1989; Yang et al., 1988; Zhang et al., 1988). For example, D'Halluin et al. (1992) demonstrated that using the neo gene and selecting with kanamycin transformants could be isolated following electroporation of immature embryos of the genotype H99 or Type I callus of the genotype PA91.

One herbicide which has been demonstrated as a desirable selection agent is the broad spectrum herbicide bialaphos (Gordon-Kamm et al., 1990; Casas et al., 1993; and Weeks et al., 1993). Bialaphos is a tripeptide antibiotic produced by *Streptomyces hygroscopicus* and is composed of phosphinothricin (PPT), an analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism (Ogawa et al., 1973). Synthetic PPT, the active ingredient in the herbicides Basta® or Ignite® is also effective as a selection agent. Inhibition of GS in plants by PPT causes the rapid accumulation of ammonia and death of the plant cells.

The organism producing bialaphos and other species of the genus Streptomyces also synthesizes an enzyme phosphinothricin acetyl transferase (PAT) which is encoded by the bar gene in *Streptomyces hygroscopicus* and the pat gene in *Streptomyces viridochromogenes*. The use of the herbicide resistance gene encoding phosphinothricin acetyl transferase (PAT) is referred to in the published German patent application DE 3642 829 A, wherein the gene is isolated from *Streptomyces viridochromogenes*. In the bacterial source organism this enzyme acetylates the free amino group of PPT preventing auto-toxicity (Thompson et al., 1987). The bar gene has been cloned (Murakami et al., 1986; Thompson et al., 1987) and expressed in transgenic tobacco, tomato and potato plants (De Block, 1987) and Brassica (De Block, 1989). In previous reports, some transgenic plants which expressed the resistance gene were completely resistant to commercial formulations of PPT and bialaphos in greenhouses.

PCT Application No. WO 87/00141 refers to the use of a process for protecting plant cells and plants against the action of glutamine synthetase inhibitors. This application also refers to the use of such of a process to develop herbicide resistance in determined plants. The gene encoding resistance to the herbicide BASTA® (Hoechst, phosphinothricin) or Herbiace® (Meiji Seika, bialaphos) was said to be introduced by Agrobacterium infection into tobacco (*Nicotiana tabacum* cv Petit Havan SR1), potato (*Solanum tuberosum* cv Benolima) and tomato (*Lycopersicum esculentum*) and conferred on plants resistance to application of herbicides.

An exemplary embodiment of vectors capable of delivering DNA to plant host cells is the plasmid, pDPG165. The plasmid pDPG165 is illustrated in FIG. 1A. A very important component of this plasmid for purposes of genetic transformation is the bar gene which encodes a marker for selection of transformed cells exposed to bialaphos or PPT.

J. Selection of bar Transformants Using Bialaphos in the Cell Line SC82 Following Particle Bombardment The suspension culture (designated SC82) used in the initial studies was derived from embryogenic Type-II callus of A188 X B73. Following bombardment, cells on filters were resuspended in nonselective liquid medium, cultured for one to two weeks and transferred to filters overlaying solid medium containing 1 or 3 mg/l bialaphos. The degree of inhibition of tissue growth during selection was dependent upon the density of the cells on the filter and on the concentration of bialaphos used. At the density plated (0.5 PCV/filter), growth of cells cultured on 1 mg/l bialaphos was only partially inhibited (~30–50% of nonselected growth) and after three to four weeks much of this tissue was transferred as discrete clumps (~5 mm in diameter) to identical medium. On medium containing 3 mg/l bialaphos, the growth of cells on the original selection filter was severely inhibited (~10% of nonselected growth) and selection was carried out without removing the tissue from the original filter.

Using either selection protocol (1 or 3, mg/l bialaphos), resistant cell colonies emerged on the selection plates of SC82 bombarded with pDPG165 approximately six to seven weeks after bombardment. Bialaphos-resistant calli were maintained and expanded on selection medium. Much of this tissue was embryogenic. No colony growth occurred on plates to which cells were added from untransformed suspension cultures. These were controls which confirm the prediction that cells without the bar gene are not resistant to bialaphos.

Colonies on solid supports are visible groups of cells formed by growth and division of cells plated on such support. The cells capable of growth are those that are resistant to the presence of the herbicide bialaphos, said resistance resulting from integration and expression of the bar gene. Exposure of cells was to 1 mg/l bialaphos. Bialaphos-resistant cultures maintained on selection media were embryogenic. One transformant recovered in this study was designated B-3-14-7 and is also referred to as E2/E5 or B16.

As a confirmation that the cells forming the colonies had indeed incorporated the bar gene and were expressing it, bialaphos-resistant callus lines were analyzed for activity of the bar gene product, phosphinothricin acetyl transferase (PAT), by thin-layer chromatography. Protein extracts from eleven callus lines (E1 to E11) isolated from SC82 bombardment studies contained PAT activity and activity levels varied approximately 10-fold among the isolates.

Still further and more direct confirmation of the presence of the bar gene was obtained by analysis of the genomic DNA of potential transformants by DNA gel blots. The sources of DNA which were electrophoresed through the gel were the bialaphos-resistant callus lines designated E1 to E11 and a non-selected control, EO. After the DNA was electrophoresed through the gel and transferred to nylon membranes, the resulting blot was hybridized with a $^{32}$P-labeled bar gene sequence from the plasmid pDPG165. The radioactivity used per blot was approximately $25 \times 10^6$ Cerenkov cpm.

Genomic DNA from all eleven bialaphos-resistant isolates contained bar-hybridizing sequences. The hybridization in all isolates to a fragment migrating slightly larger than 2 kb may be due to contaminating pUC19 sequences contained in this bar probe preparation; no such hybridization occurred in subsequent studies using the same genomic DNA and a different preparation of the bar probe. Hybridization to a 1.9 kb fragment in eight of the it isolates indicated that these isolates contained intact copies of the 1.9 kb bar expression unit. The estimated copy numbers of the intact unit ranged from one or two (E1, E7, E8, E10, E11) to approximately 20 (E3, E4, E6). Hybridization with the bar probe in isolate B16 occurred only to a single, higher molecular weight fragment (~3 kb).

To establish that the PAT coding sequence was intact in isolate B16 (also known as E2 or E5) genomic DNA was digested with SmaI, which releases a 559 bp fragment containing the PAT structural gene (FIG. 1A), and subjected to DNA gel blot analysis using $^{32}$p-labeled bar. This analysis confirmed the presence of a single intact copy of bar. Expression of PAT in these isolates may not be dependent on the 35S promoter or the Tr7 3' end. The hybridization patterns of some of the isolates were identical (E2 and E5; E7 and E8; E3, E4, and E6); therefore, it is probable that some isolates did not arise from independent transformation events but represent transformants that were separated during selection.

Seven hybridization patterns were unique, likely representing seven independent single-cell transformation events. The patterns and intensities of hybridization for the seven transformants were unchanged during four months in culture, providing evidence for the stability of the integrated sequences. The seven independent transformants were derived from two separate bombardment studies. Four independent transformants representing isolates E2/E5, E3/E4/E6, E1 and E7/E8, were recovered from a total of four original filters from a first study and the three additional independent transformants, E9, E10, and E11, were selected from tissue originating from six bombarded filters in a second study.

K. Transformation of Cell. Line AT824 Using Bialaphos Selection Following Particle Bombardment—Selection in Liquid Medium The suspension culture (designated AT824) used in this study was derived from an elite B73-derived inbred. The culture was maintained in medium 409. Four filters were bombarded as described in the present example.

Following one week culture in liquid medium 409 without selection pressure, tissue was transferred to liquid medium 409 containing 1 mg/L bialaphos. Cells were transferred twice per week into fresh medium containing 1 mg/L bialaphos for two weeks. Tissue was thin plated three weeks following bombardment at a concentration of 0.1 ml packed cell volume per petri dish containing medium 425 (with 3 mg/L bialaphos). Transformants were identified as discreet colonies six weeks following bombardment. It is the experience of the inventors that all cell lines that grow on 3 mg/L bialaphos contain the bar gene. Fifty transformed cell lines were recovered from this study.

L. Transformation of Cell Line AT824 Usinq Bialaphos Selection Following Particle Bombardment—Solid Medium Selection Cells in study S10 were bombarded as described earlier in this example, except the gold participle-DNA preparation was made using 25 µl pDPG319 DNA (bar gene and aroA expression cassette containing the α-tubulin promoter). Following particle bombardment, cells remained on solid 279 medium in the absence of selection for one week. At this time cells were removed from solid medium, resuspended in liquid 279 medium, replated on Whatman filters at 0.5 ml PCV per filter, and transferred to 279 medium containing 1 mg/L bialaphos. Following one week, filters were transferred to 279 medium containing 3 mg/L bialaphos. One week later, cells were resuspended in liquid 279 medium and plated at 0.1 ml PCV on 279 medium containing 3 mg/L bialaphos. Nine transformants were identified seven weeks following bombardment.

M. Regeneration of Plants from SC82

One efficient regeneration system involved transfer of embryogenic callus to MS (Murashige & Skoog, 1962)

medium containing 0.25 mg/l 2,4-dichlorophenoxyacetic acid and 10.0 mg/l 6-benzyl-aminopurine. Tissue was maintained on this medium for approximately two weeks and subsequently transferred to MS medium without growth regulators (Shillito et al., 1989). Shoots that developed after two to four weeks on growth regulator-free medium were transferred to MS medium containing 1% sucrose and solidified with 2 g/l Gelgro®$^R$ in Plant Con$^R$ containers where rooting occurred.

Another successful regeneration scheme involved transfer of embryogenic callus to N6 (Chu et al., 1975) medium containing 6% sucrose and no growth regulators (Armstrong & Green, 1985) for two weeks followed by transfer to MS medium without growth regulators as described above. Regeneration was performed at 25° C. under fluorescent lights (250 microeinsteins·m$^{-2}$·s$^{-1}$). After approximately two weeks developing plantlets were transferred to a Plant Con® container containing medium 501. When plantlets had developed three leaves and two to three roots they were transferred to soil, hardened off in a growth chamber (85% relative humidity, 600 ppm $CO_2$, 250 microeinsteins·m$^{-2}$·s$^{-1}$), and grown to maturity either in a growth chamber or a greenhouse.

Regeneration of plants from transformed cells requires careful attention to details of tissue culture techniques. One of the major factors is the choice of tissue culture media. There are many media which will support growth of plant cells in suspension cultures, but some media give better growth than others at different stages of development. Moreover, different cell lines respond to specific media in different ways. A further complication is that treatment of cells from callus initiation through transformation and ultimately to the greenhouse as plants, requires a multivariate approach. A progression consisting of various media types, representing sequential use of different media, is needed to optimize the proportion of transformed plants that result from each cell line.

A preferred embodiment for use on cell lines SC82, at least initially, is the combination of culture media 227, 171, 101, 501. Media 227 is a good media for the selective part of the studies, for example, to use for growth of callus in the presence of bialaphos. This media contains the growth regulator dicamba. NAA and 2,4-D are growth regulators in other media.

Thus, it can be seen from Table 1 that the various media are modified so as to make them particularly applicable to the development of the transformed plant at the various stages of the transformation process. For example, subculture of cells in media 171 after applying the selective agent, yields very small embryos. Moreover, it is believed that the presence of BAP in the media facilitates development of shoots. Myo-inositol is believed to be useful in cell wall synthesis. Shoot elongation and root development proceeds after transfer to media 101. 101 and 501 do not contain the growth regulators that are required for earlier stages of regeneration.

Transfer of regenerating plants is preferably completed in an agar-solidified media adapted from a nutrient solution developed by Clark (1982), media 501. The composition of this media facilitates the hardening of the developing plants so that they can be transferred to the greenhouse for final growth as a plant. The salt concentration of this media is significantly different from that of the three media used in the earlier stages, forcing the plant to develop its own metabolic pathways. These steps toward independent growth are required before plants can be transferred from tissue culture vessels (e.g. petri dishes, plant cans) to the greenhouse.

Approximately 50% of transformed callus lines derived from the initial SC82 studies were regenerable by the routes tested. Transgenic plants were regenerated from four of seven independent SC82 transformants and 10 of 20 independent SC716 transformants.

Regeneration of transformed SC82 selected cell lines yielded 76 plants transferred to the soilless mix, and 73 survived. The plants were regenerated from six bialaphos-resistant isolates, representing four of seven clonally independent transformants. Eighteen protocols were used successfully to regenerate the 76 plants (Table 2). Differences in morphology between cell lines deemed some protocols more suitable than others for regeneration.

TABLE 2

EFFECTS OF PROGRESSION OF MEDIA ON THE NUMBER OF PLANTS REGENERATED (SC82) *

| CELL LINE | 227B 142 101 501 | 227B 173 101 501 | 227B 171 101 501 | 227B 227A 205 101 501 | 227B 227A 209 101 501 | 227B 227A 173 101 501 | 227B 171 173 101 501 | 227B 52 173 101 501 | 227B 52 173 101 501 | 227B 52 171 101 501 | 227B 201B 171 173 101 501 | 227B 201B 173 101 501 | 227B 178 101 501 | 227B 201B 205 171 101 501 | 227B 227B 177 101 501 | 227B 201B 205 177 101 501 | 227B 201B 1 178 101 501 | 227B 201B 52 171 101 501 | # OF PLANTS |
|---|---|---|---|---|---|---|---|---|---|---|---|---|---|---|---|---|---|---|---|
| B3-14-4 | 1 | X | 14 | X | X | X | 1 | 1 | X | 2 | X | X | 5 | X | 5 | X | X | X | 29 |
| B3-14-9 | X | X | 1 | 1 | X | 4 | 1 | X | X | X | X | X | X | 1 | X | 1 | X | X | 9 |
| B3-14-7 | X | X | X | X | X | X | X | X | X | X | 6 | 2 | X | X | X | X | X | 1 | 9 |
| B3-14-6 | X | X | X | X | 1 | X | X | X | X | X | X | X | X | X | X | X | X | X | 1 |
| B3-14-3 | X | X | X | X | X | X | X | X | X | X | X | X | X | X | X | X | X | X | 0 |
| B3-14-2 | X | X | X | X | X | X | X | X | X | X | X | X | X | X | X | X | X | X | 0 |
| B3-14-1 | X | X | X | X | X | X | X | X | X | X | X | X | X | X | X | X | X | X | 0 |
| B3-14-5 | X | X | X | X | X | X | X | X | X | X | X | X | X | X | X | X | X | X | 0 |
| B3-13-5 | X | X | X | X | X | X | X | X | X | X | X | X | X | X | X | X | X | X | 0 |
| B3-13-2 | X | 1 | 13 | X | X | X | 3 | 2 | 2 | X | X | X | X | X | 1 | X | X | X | 22 |
| B3-13-1 | X | 3 | X | 1 | X | X | X | X | 1 | X | X | X | X | X | X | X | 1 | X | 6 |
| TOTAL | 1 | 4 | 28 | 2 | 1 | 4 | 5 | 3 | 3 | 2 | 6 | 2 | 5 | 1 | 6 | 1 | 1 | 1 | 76 |

* = See table 1 for media codes.
X = This media progression was either attempted and unsuccessful or not attempted.
227A = 227 with $10^{-7}$M ABA.
227B = 227 with 1 mg/l bialaphos.

Prior to regeneration, the callus was transferred to either a) an N6-based medium containing either dicamba or 2,4-D or b) an MS-based medium containing 2,4-D. These steps allowed further embryoid development prior to maturation. Most of the maturation media contained high BAP levels (5 to 10 mg/l) to enhance shoot development and cause proliferation. An MS-based medium with low 2,4-D (0.25 mg/l) and high BAP (10 mg/l), as described by Shillito et al. (1989) was found to be quite effective for regeneration.

Likewise, an MS-based medium containing 1 μm NAA, 1 μm IAA, 2 μm 2-IP, and 5 mg/l BAP (modified from Conger et al., 1987) also promoted plant regeneration of these transformants. After plantlets recovered by any of the regenerative protocols had grown to 5 cm, they were transferred to a nutrient solution described by Clark (1982) supplemented with 2% sucrose and solidified with Gelgro®. Plantlets which were slow to develop roots were treated with 3 μl droplets of 0.3% IBA at the base of the shoot to stimulate rooting. Plants with well-developed root systems were transferred to a soilless mix and grown in controlled environmental chambers from five to 10 days, prior to transfer to the greenhouse.

N. Regeneration of AT824 Transformants

Transformed tissue was first transferred to solid medium 223 and incubated for two weeks. Transformants may be initially subcultured on any solid culture that supports callus growth, e.g., 223, 425, 409 and so forth. Subsequently transformants were subcultured one to three times, but usually twice on 189 medium (first passage in the dark and second passage in low light) and once or twice on 101 medium in petri dishes before being transferred to 607 medium in Plant Con® containers. Variations in the regeneration protocol were normal based on the progress of plant regeneration. Hence some of the transformants were first subcultured once on 425 medium, twice on 189 medium, once or twice on 101 medium followed by transfer to 501 medium in Plant Cons® containers. As shoots developed on 101 medium, the light intensity was increased by slowly adjusting the distance of the plates from the light source located overhead. All subculture intervals were for about two weeks at 24° C. Transformants that developed three shoots and two to three roots were transferred to soil.

Plantlets in soil were incubated in an illuminated growth chamber and conditions were slowly adjusted to adapt or condition the plantlets to the drier and more illuminated conditions of the greenhouse. After adaptation/conditioning in the growth chamber, plants were transplanted individually to five gallon pots of soil in the greenhouse.

O. Recovery of Fertile Plants

To recover progeny the regenerated, genetically transformed maize plants (designated $R_0$), were backcrossed with pollen collected from nontransformed plants derived from seeds. Alternatively pollen was collected from $R_0$ plants and used to pollinate nontransformed plants. Progeny (designated $R_1$) that contained and expressed bar were recovered from crosses in which the transformant was used as a male or female parent.

Pollination of transgenic $R_0$ ears with non-transformed B73 pollen resulted in kernel development. In addition, kernels developed from pistillate flowers on male inflorescences that were pollinated with non-transformed B73 pollen. Kernels on transformed $R_0$ plants from SC82 developed normally for approximately 10 to 14 days post-pollination but after this period the kernels ceased development and often collapsed. Most plants exhibited premature senescence at this time. A total of 153 kernels developed sporadically on numerous plants: eight of 37 E2/E5 plants, two of 22 E10 plants, and three of six E11 plants. Viable progeny were recovered by embryo rescue from 11 E2/E5 plants and one E10 plant.

Fertile plants from over 250 transgenic lines have produced over 59,000 seed (about 227 $R_1$ seed per transgenic line). These plants were derived from 11 different cell lines. In addition, both male and female fertility has been observed in many of these cells lines. Kernels routinely mature on plants for which the transformant is either the male or the female parent. Embryo rescue was only necessary under unusual circumstances.

P. Embryo Rescue

In cases where embryo rescue was required, developing embryos were excised from surface disinfected kernels 10 to 20 days post-pollination and cultured on medium containing MS salts, 2% sucrose and 5.5 g/l Seakem agarose. Large embryos (>3 mm) were germinated directly on the medium described above. Smaller embryos were cultured for approximately one week on the above medium containing $10^{-5}$M abscisic acid and transferred to growth regulator-free medium for germination. Embryos that became bacterially contaminated were transferred to medium containing 300 μg/ml cefoxitin. Developing plants were subsequently handled as described for regeneration of $R_0$ plants.

Viable progeny, recovered from seven SC82 E2/E5 plants and one SC82 E10 plant, were sustained by embryo rescue. This method consisted of excising embryos from kernels that developed on $R_0$ plants. Embryos ranged in size from about 0.5 to 4 mm in length. Small embryos were cultured on maturation medium containing abscisic acid while larger embryos were cultured directly on germination medium.

Pollen obtained from transformed $R_1$ plants has been successfully employed to pollinate B73 ears and a large number of seeds have been recovered. The fertility characteristics of the $R_1$ generation has been confirmed both from a standpoint of the pollen's ability to fertilize nontransformed ears, and the ability of $R_1$ ears to be fertilized by pollen from non-transformed plants.

Example II

Transformation of Immature Embryos by Particle Bombardment

Immature embryos of maize (Koziel et al., 1993), barley (Wan & Lemaux, 1994), sorghum (Casas et al., 1993), wheat (Weeks et al., 1993) and rice (Christou et al., 1991) have been demonstrated to be a suitable target for production of transformed plants via microprojectile bombardment. The following example exemplifies the transformation of maize via microprojectile bombardment of immature embryos. Although the process is exemplified with the genotype HiII (Armstrong et al., 1991), the method is not limited to this genotype and has been successfully applied to other genotypes of maize including H99, PA91, A188 x B73 and various crosses of the HiII genotype to elite inbred lines.

A. Bombardment of Immature Embryos

Immature embryos (1.2 to 2.0 mm in length) were excised from surface-sterilized, greenhouse-grown ears of Hi-II 11 to 12 days post-pollination. The Hi-II genotype was developed from an A188 x B73 cross for high frequency development of Type II callus from immature embryos (Armstrong et al., 1991). Approximately 30 embryos per petri dish were plated axis side down on a modified N6 medium containing 1 mg/l 2,4-D, 100 mg/l casein hydrolysate, 6 mM L-proline, 0.5 g/l 2-(N-morpholino) ethanesulfonic acid (MES), 0.75 g/l $MgCl_2$, and 2% sucrose solidified with 2 g/l Gelgro®, pH 5.8 (#735 medium) Embryos were cultured in the dark for two days at 24° C.

Approximately four hours prior to bombardment, embryos were transferred to the above culture medium with the sucrose concentration increased from 3% to 12%. When embryos were transferred to the high osmoticum medium they were arranged in concentric circles on the plate, starting 2 cm from the center of the dish, positioned such that their coleorhizal end was orientated toward the center of the dish. Usually two concentric circles were formed with 25 to 35 embryos per plate.

Preparation of gold particles carrying plasmid DNA was as described herein. Particles were prepared containing 10 μg pDPG215 (luciferase), pDPG415 (Bt), and pDPG417 (bar) or 30 μg pDPG265 containing the maize R and C1B genes for anthocyanin biosynthesis.

The plates containing embryos were placed on the third shelf from the bottom, 5 cm below the stopping screen. The 1100 psi rupture discs were used. Each plate of embryos was bombarded once. A total of 420 embryos were bombarded on 14 plates with the luciferase, bar, and Bt genes. Embryos were allowed to recover overnight on high osmotic strength medium prior to initiation of selection. A set of plates was also bombarded with the ClB vector pDPG265. Red spots representing transient expression of anthocyanin pigments were observed 24 hours after DNA introduction.

B. Transformation of Immature Embryos of the Genotype Hi-II Using Bialaphos as a Selective Agent Following Particle Bombardment Embryos were allowed to recover following bombardment on high osmoticum medium (735, 12% sucrose) overnight (16–24 hours) and were then transferred to selection medium containing 1 mg/l bialaphos (#739, 735 plus 1 mg/l bialaphos or #750, 735 plus 0.2M mannitol and 1 mg/l bialaphos). Embryos were maintained in the dark at 24° C. After three to four weeks on the initial selection plates about 90% of the embryos had formed Type II callus and were transferred to selective medium containing 3 mg/l bialaphos (#758, medium #735 plus 3 mg/l bialaphos). Responding tissue was subcultured about every two weeks onto fresh selection medium (#758). Nineteen transformants were identified six to eight weeks after bombardment. Plants were regenerated following the procedures outlined herein. Regenerated plants were transferred to the greenhouse, pollinated by inbred plants and seed harvested.

Example III

Transformation by Electroporation

A. Electroporation Study EP413: Stable Transformation of Cells Using PDPG165 and pDPG208

Transformation of *Zea mays* via electroporation and production of fertile transgenic plants have been demonstrated by D'Halluin et al. (1992) and Laursen et al. (1994). D'Halluin et al. (1992) demonstrated production of fertile transformants of *Zea mays* following electroporation of maize Type I callus or immature embryo whereas Laursen et al. (1994) demonstrated transformation of maize suspension culture cells and recovery of fertile transgenic plants. The following exemplifies electroporation of maize suspension cells, but the method is equally applicable to other maize cell types including Type I callus and immature embryos and other genotypes of maize.

Maize suspension culture cells were enzyme treated and electroporated using conditions described in Krzyzek and Laursen (PCT Publication WO 92/12250). AT824 suspension culture cells, three days post subculture, were sieved through 1000 μm stainless steel mesh and washed, 1.5 ml packed cells per 10 ml, in incubation buffer (0.2 M mannitol, 0.1% bovine serum albumin, 80 mM calcium chloride, and 20 mM 2-(N-morpholino)-ethane sulfonic acid, pH 5.6). Cells were then treated for 90 minutes in incubation buffer containing 0.5% pectolyase Y-23 (Seishin Pharmaceutical, Tokyo, Japan) at a density of 1.5 ml packed cells per 5 ml of enzyme solution. During the enzyme treatment, cells were incubated in the dark at approximately 25° C. on a rotary shaker at 60 rpm. Following pectolyase treatment, cells were washed once with 10 ml of incubation buffer followed by three washes with electroporation buffer (10 mM HEPES, 0.4 mM mannitol). Cells were resuspended in electroporation buffer at a density of 1.5 ml packed cells in a total volume of 3 ml.

Linearized plasmid DNA, 100 μg of EcoRI digested pDPG165 and 100 μg of EcoRI digested pDPG208, was added to 1 ml aliquots of electroporation buffer. The DNA/electroporation buffer was incubated at room temperature for approximately 10 minutes. To these aliquots, 1 ml of suspension culture cells/electroporation buffer (containing approximately 0.5 ml packed cells) were added. Cells and DNA in electroporation buffer were incubated at room temperature for approximately 10 minutes. One-half ml aliquots of this mixture were transferred to the electroporation chamber (Puite, 1985) which was placed in a sterile 60×15 mm petri dish. Cells were electroporated with a 70, 100, or 140 volt (V) pulse discharged from a 140 microfarad (μf) capacitor.

Approximately 10 minutes post-electroporation, cells were diluted with 2.5 ml 409 medium containing 0.3 M mannitol. Cells were then separated from most of the liquid medium by drawing the suspension up in a pipet, and expelling the medium with the tip of the pipet placed against the petri dish to retain the cells. The cells, and a small amount of medium (approximately 0.2 ml) were dispensed onto a filter (Whatman #1, 4.25 cm) overlaying solid 227 medium (Table 1) containing 0.3 M mannitol. After five days, the tissue and the supporting filters were transferred to 227 medium containing 0.2 M mannitol. After seven days, tissue and supporting filters were transferred to 227 medium without mannitol.

B. Transformation of AT824 Using Bialaphos Selection Following Electroporation

Cells of AT824 were electroporated and allowed to recover from electroporation as described above. Five days later, tissue growing on filters was removed from the filter and transferred as clumps (approximately 0.5 cm in diameter) to the surface of solid selection medium. The selection medium consisted of 227 medium supplemented with 1 mg/L bialaphos. Three weeks later, slowly growing tissue was transferred, as 0.5 cm clumps, to 227 medium containing 3 mg/L bialaphos. Three to four weeks later, callus sectors that continued to grow were transferred to fresh 227 medium containing 3 mg/L bialaphos. Callus lines that continued to grow after this subculture were considered to be transgenic and perpetuated further, by transfer to fresh selection medium every two weeks. Seven AT824 callus lines were selected in this example. Three AT824 callus lines were recovered from 140 µf, 70 V electroporations and four AT824 callus lines were recovered from electroporation at 140 µf, 140 V.

Two bialaphos resistant callus lines selected in this example were randomly chosen and assayed for phosphinothricin acetyltransferase (PAT) activity. PAT is the bar gene product, and PAT activity is determined by the ability of total protein extracts from potentially transformed cells to acetylate phosphinothricin (PPT), using $^{14}$C-acetyl coenzyme A as the acetyl donor. This transfer is detected, using thin layer chromatography and autoradiography, by a shift in the mobility of $^{14}$C labelled compound from that expected for $^{14}$C-acetyl coenzyme A to that expected for $^{14}$C-N-acetyl PPT. The assay used for detection of PAT activity has been described in detail (Adams et al., published PCT application no. WO91/02071; Spencer et al., 1990). All three callus lines tested contained PAT activity.

In this example, suspension culture cells were electroporated with a second plasmid, pDPG208, encoding β-glucuronidase (GUS). Detection of GUS activity can be performed histochemically using 5-bromo-4-chloro-3-indolyl glucuronide (x-gluc) as the substrate for the GUS enzyme, yielding a blue precipitate inside of cells containing GUS activity. This assay has been described in detail (Jefferson, 1987). One of the seven AT824 callus lines selected in this example, EP413-13, contained cells that turned blue in the histochemical assay.

Southern blot analysis was performed on three bialaphos resistant callus lines to determine the presence and integration of the bar gene in genomic callus DNA. Southern blot analysis was performed as follows. Genomic DNA was isolated using a procedure modified from Shure et al. (1983). Approximately one gram of callus tissue from each line was lypholyzed overnight in 15 ml polypropylene tubes. Freeze-dried tissue was ground to a powder in the tube using a glass rod. Powdered tissue was mixed thoroughly with 3 ml extraction buffer (7.0 M urea, 0.35 M NaCl, 0.05 M Tris-HCl pH 8.0, 0.01 M EDTA, 1% sarcosine). Tissue/buffer homogenate was extracted with 3 ml phenol/chloroform. The aqueous phase was separated by centrifugation, and precipitated twice using 1/10 volume of 4.4 M ammonium acetate pH 5.2, and an equal volume of isopropanol. The precipitate was washed with 75% ethanol and resuspended in 100–500 µl TE (0.01 M Tris-HCl, 0.001 M EDTA, pH 8.0). Genomic DNA was digested with a 3-fold excess of restriction enzymes, electrophoresed through 0.8% agarose (FMC), and transferred (Southern, 1975) to Nytran® (Schleicher and Schuell) using 10×SCP (20×SCP: 2 M NaCl, 0.6 M disodium phosphate, 0.02 M disodium EDTA). Filters were prehybridized in 6×SCP, 10% dextran sulfate, 2% sarcosine, and 500 µg/ml heparin (Chomet et al., 1987) for approximately 10 minutes. Filters were hybridized overnight at 65° C. in 6×SCP containing 100 µg/ml denatured salmon sperm DNA and $^{32}$P-labelled probe. Probe was generated by random priming (Feinberg & Vogelstein, 1983) Hybridized filters were washed in 2×SCP, 1% SDS at 65° C. for 30 minutes and visualized by autoradiography using Kodak XAR5 film.

In this example, genomic DNA isolated from bialaphos resistant callus lines was digested with HindIII and EcoRI, which release a 1.9 kb bar fragment from pDPG165 (FIG. 1A). Genomic DNA was probed with $^{32}$p labelled 0.6 kb SmaI bar fragment from pDPG165. (FIG. 1A). All three EP413 callus lines analyzed contained DNA that hybridized to the bar probe. Copy number in the transformed callus ranged from one to two copies (EP413-3) to greater than 20 copies of bar (EP413-1). Furthermore, the restriction digest used, yielded bar-hybridizing fragments in callus DNA samples that were larger than the bar fragment released from pDPG165 in the same restriction digest. This result is indicative of stable integration of introduced DNA into the maize genome.

Thirty-nine plants were regenerated from seven of the eight bialaphos resistant callus lines selected in this example. Plants were regenerated from six AT824 callus lines. For plant regeneration, callus growing on 227 medium containing 3 mg/L bialaphos, was transferred to 189 medium (Table 1). Somatic embryos matured on 189 medium after one, two, or three two-week subculture periods in the dark at 25° C. As somatic embryos developed on 189 medium, clumps of tissue containing these embryos were transferred to growth regulator free 101 medium (Table 1) and placed in the light (25–250 µE M$^{-2}$ s$^{-1}$) Plantlets developed on this medium after one, two, or three subculture periods. Plantlets were subsequently transferred to 501 medium (Table 1) in Plant Con$^R$ containers for rooting and further growth. Regenerates (R$_0$ plants) were subsequently transferred to a soilless mix in 0.5 liter pots and acclimated to ambient humidity in a growth chamber (200–450 µE M$^{-2}$ s$^{-1}$; 14 h photoperiod). The soilless mix has been described in detail (Adams et al., published PCT application no. WO91/02071). Plants were then transferred to a soilless mix in 16 liter pots and grown to maturity in a greenhouse.

Plants regenerated from five different EP413 callus lines were assayed for PAT activity as described for callus earlier in this example. All five plants contained PAT activity. Three plants regenerated from the single EP413 callus line that exhibited GUS activity (EP413-13) were analyzed for GUS activity. All three EP413-13 R$_0$ plants were positive for GUS activity. Files of blue cells were observed in leaf tissue of EP413-13 plants upon incubation with X-Gluc.

EP413 R$_0$ plants were also analyzed for the presence and integration of bar by Southern blot. DNA was isolated from leaf tissue as described for callus except that fresh, rather than lypholyzed tissue was used. Prior to the addition of extraction buffer, fresh leaf tissue was frozen in liquid nitrogen and ground to a fine powder in a 15 ml polypropylene tube using liquid nitrogen and a glass rod. DNA was isolated from four EP413 R$_0$ plants, each representing a different callus line. DNA was analyzed, digested with HindIII and BglII, or undigested, for hybridization to bar. R$_0$ DNA was probed with $^{32}$p labelled 0.6 kb SmaI bar fragment from pDPG165 (FIG. 1A). HindIII/BglII digestion of pDPG165 releases a fragment containing 35S-bar of approximately 1.3 kb (FIG. 1A). Genomic DNA from all four plants contained at least one copy of the 1.3 kb HindIII/BglII 35S-bar fragment. In addition, undigested genomic DNA from all four plants exhibited hybridization to bar only in high molecular weight DNA (>20 kb), indicating integration of pDPG165 into maize chromosomal DNA.

Progeny were recovered from outcrosses made between electroporation-derived, transgenic R$_0$ plants and non-transformed inbred plants. Four EP413-3 R$_0$ plants were the first of the plants to reach maturity and flower. One of the plants was outcrossed as the male to a CD inbred plant. This cross resulted in 22 kernels. Sixteen of these kernels were planted in soilless mix and all germinated. Approximately two weeks post-germination, the progeny (R$_1$) plants were analyzed for PAT activity. Three of 16 plants contained PAT activity.

Four transgenic EP413-3 $R_0$ plants were also outcrossed as the female, using pollen collected from nontransformed inbred plants. Kernels developed on ears of all four EP413-3 $R_0$ plants. Thirty-seven kernels were recovered from an ear on an EP413-3 $R_0$ plant treated with pollen collected from a seed-derived, non-transformed FBLL inbred plant. Sixteen of these kernels were planted in soil and 12 germinated. Eight of these plants were analyzed for PAT activity; three of eight were positive for PAT activity.

These eight plants were also analyzed by Southern blot hybridization for the presence of bar. Genomic DNA isolated from these eight EP413-3 $R_1$ plants was digested with restriction enzymes HindIII and BglII, which release a 1.3 kb fragment containing bar from pDPG165. In addition to DNA from the eight EP413-3 $R_1$ plants, DNA isolated from EP413-3 callus and DNA from the EP413-3 $R_0$ plant yielding these eight $R_1$ plants was included in the analysis. Genomic DNA was probed with $^{32}$P labelled 0.6 kb SmaI bar fragment from pDPG165. Hybridization to bar was detected in the DNA isolated from callus, $R_0$ and the three $R_1$ plants that contained PAT activity. Each of the bar-positive plants contained the expected 1.3 kb HindIII/BglII fragment from pDPG165 as well as an additional, larger bar-hybridizing fragment of approximately 2.0 kb. This result, as well as the PAT activity found to be present in EP413-3 $R_1$ plants, conclusively demonstrates the sexual transmission to progeny of a functional gene introduced into maize cells by electroporation.

EXAMPLE IV

Analysis of Integration of Exogenous DNA in Transformants and Progeny Plants

Transformed plants derived from particle bombardment of cultured cells or immature embryos or derived from electroporation are analyzed in a similar manner. Although analysis of plants derived from particle bombardment of cultured cells are disclosed herein, similar analysis could be undertaken on any transformed plant.

A. General Methods for Assays

A method to detect the presence of phosphinothricin acetyl transferase (PAT) activity is to use an in vitro enzyme reaction followed by thin layer chromatography.

Various protein extracts prepared from homogenates of potentially transformed cells, and from control cells that have neither been transformed nor exposed to bialaphos selection, were assayed by incubation with PPT and $^{14}$C-Acetyl Coenzyme A followed by thin layer chromatography. Twenty-five μg of protein extract were loaded per lane. The source in lanes E1 to E11 were SC82 transformants; B13 was a BMS (Black Mexican Sweet corn nonembryogenic) bar transformant. E0 was a nonselected, nontransformed control.

All lanes except the nontransformed control exhibit PAT activity by the formation of a compound with the appropriate mobility expected for $^{14}$C-N-Acetyl PPT. Variation in activity levels among the transformants was approximately 10-fold, as demonstrated by the relative intensity of the bands. The results of this assay provide confirmation of the expression of the bar gene which codes for PAT. For analysis of PAT activity in plant tissue, 100–200 mg of leaf tissue was extracted in sintered glass homogenizers and assayed as described previously.

DNA analysis was performed as follows. Genomic DNA was isolated using a procedure modified from Shure et al. (1983). Approximately 1 gm callus tissue was ground to a fine powder in liquid N2 using a mortar and pestle. Powdered tissue was mixed thoroughly with 4 ml extraction buffer (7.0 M urea, 0.35 M NaCl, 0.05 M Tris-HCl pH 8.0, 0.01 M EDTA, 1% sarcosine). Tissue/buffer homogenate was extracted with 4 ml phenol/chloroform. The aqueous phase was separated by centrifugation, passed through Miracloth®, and precipitated twice using 1/10 volume of 4.4 M ammonium acetate, pH 5.2 and an equal volume of isopropanol. The precipitate was washed with 70% ethanol and resuspended in 200–500 μl TE (0.01 M Tris-HCl, 0.001 M EDTA, pH 8.0). Plant tissue may also be employed for the isolation of DNA using the foregoing procedure.

The presence of a gene in a transformed cell may be detected through the use of polymerase chain reaction (PCR). Using this technique, specific fragments of DNA can be amplified and detected following agarose gel electrophoresis. For example the bar gene may be detected using PCR. Two hundred to 1000 ng genomic DNA is added to a reaction mix containing 10 mM Tris-HCl pH 8.3, 1.5 mM $MgCl_2$, 50 mM KCl, 0.1 mg/ml gelatin, 200 μM each DATP, dCTP, dGTP, dTTP, 0.5 μM each forward and reverse DNA primers, 20% glycerol, and 2.5 units Taq DNA polymerase. The forward primer is CATCGAGACAAGCACGGT-CAACTTC (position 114 to position 147 of SEQ ID NO:3). The reverse primer is AAGTCCCTGGAGGCACAGGGCT-TCAAGA (position 364 to position 391 of SEQ ID NO:3). PCR amplification of bar using these primers requires the presence of glycerol, but this component is not needed for most other applications. The reaction is run in a thermal cycling machine as follows: three minutes at 94° C., 39 repeats of the cycle one minute at 94° C., one minute at 50° C., 30 seconds at 72° C., followed by five minutes at 72° C. Twenty μl of each reaction mix is run on a 3.5% NuSieve gel in TEE buffer (90 mM Tris-borate, 2 mM EDTA) at 50V for two to four hours. Using these primers a 279 base pair fragment of the bar gene is amplified.

For Southern blot analysis genomic DNA was digested with a 3-fold excess of restriction enzymes, electrophoresed through 0.8% agarose (FMC), and transferred (Southern, 1975) to Nytran® (Schleicher and Schuell) using 10×SCP (20×SCP: 2 M NaCl, 0.6 M disodium phosphate, 0.02 M disodium EDTA). Filters were prehybridized at 65° C. in 6×SCP, 10% dextran sulfate, 2% sarcosine, and 500 μg/ml heparin (Chomet et al., 1987) for 15 minutes. Filters were hybridized overnight at 65° C. in 6×SCP containing 100 μg/ml denatured salmon sperm DNA and $^{32}$P-labeled probe. The 0.6 kb SmaI fragment from pDPG165 and the 1.8 kb BamHI/EcoRI fragment from pCEV5 were used in random priming reactions (Feinberg & Vogelstein, 1983) to generate labeled probes for detecting sequences encoding PAT or GUS, respectively. Filters were washed in 2×SCP, 1% SDS at 65° C. for 30 minutes and visualized by autoradiography using Kodak XAR5 film. Prior to rehybridization with a second probe, the filters were boiled for 10 min. in distilled $H_2O$ to remove the first probe and then prehybridized as described above.

B. Assays for Integration of Exogenous DNA and Expression of DNA in $R_0$ $R_1$ Plants Studies were undertaken to determine the expression of the transformed gene(s) in transgenic $R_0$ and $R_1$ plants. Functional activity of PAT was assessed by localized application of a commercial herbicide formulation containing PPT to leaves of SC82 $R_0$ and $R_1$ plants. No necrosis was observed on leaves of $R_0$ plants containing either high levels (E2/E5), or low levels (E3/E4) of PAT. Herbicide was also applied to leaves of E2/E5 progeny segregating for bar.

Twenty-one $R_0$ plants, representing each of the four regenerable transformed SC82 callus lines, were also analyzed for expression of the bar gene product, PAT, by thin-layer chromatographic techniques. Protein extracts from the leaves of the plants were tested.

All 21 plants tested contained PAT activity. Furthermore, activity levels were comparable to levels in the callus lines from which the plants were regenerated. The nontransformed plant showed no PAT activity (no band is in the expected position for acetylated PPT in the autoradiograph from the PAT chromatogram). A band appears in the BMS lane that is not in lanes containing protein extracts from the plant leaves. This extra band was believed to be an artifact.

As another method of confirming that genes had been delivered to cells and integrated, genomic (chromosomal) DNA was isolated from a nontransformed plant, the four regenerable callus lines and from two $R_0$ plants derived from each callus line. The transformed callus and all plants regenerated from transformed callus contained sequences that hybridized to the bar probe, indicating the presence of DNA sequences that were complementary to bar. Furthermore, in all instances, hybridization patterns observed in plant DNA were identical in pattern and intensity to the hybridization profiles of the corresponding callus DNA.

DNA from E3/E4/E6 callus and the desired $R_0$ plants contained approximately 20 intact copies of the 1.9 kb bar expression unit (Cauliflower Mosaic Virus 35S promoter-bar-Agrobacteriumtranscript 7 3'-end) as well as numerous other bar-hybridizing fragments. E11 callus and plant DNA contained one to two copies of the intact expression unit and five to six additional non-intact hybridizing fragments. E10 callus and plants contained one to two copies of the intact bar expression unit. E2/E5 DNA contained a single fragment of approximately 3 kb that hybridized to the probe. To confirm that the hybridizing sequence observed in all plants was integrated into the chromosomal DNA, undigested genomic DNA from one plant derived from each independent transformant was analyzed by DNA gel blot hybridization. Hybridization to bar was observed only in high molecular weight DNA providing evidence for the integration of bar into the maize genome.

EXAMPLE V

Analysis of Transformant B16

A detailed analysis of SC82 transformant B16 was undertaken. The B16 integration event was mapped to the long arm of chromosome 3 by use of waxy translocation lines of maize provided by the Maize Genetics Cooperation, Sarah Hake, and Paul Chomet. The integration event was specifically mapped using waxy translocations wx09A and wx08A. The examples that follow provide further characterization of the B16 transformant.

A. DNA Analysis of the Transformant B16

DNA analysis of the Ignite-resistant line, B16, involved restriction digest mapping and Southern blot hybridization analysis to determine the number of plasmid DNA insertions into genomic DNA and to define the organization and identity of the integrated plasmid DNA. This analysis was also used to determine the location of plasmid pDPG165 insert/maize genomic DNA junctions. DNA isolation, restriction digests, and Southern blot hybridization were performed as described in Gordon-Kamm et al. (1990). A restriction map of pDPG165, the plasmid used for transformation of B16, is shown in FIG. 1A. It was shown in Gordon-Kamm et al. (1990) that a HindIII/EcoRI digest of B16 callus or $R_0$ DNA, probed with bar, yielded a fragment of approximately 3 kb (B16 was referred to as "E2/E5" in Gordon-Kamm et al., 1990) Unique HindIII and EcoRI sites flank the bar expression cassette in pDPG165 (FIG. 1A), and digestion of pDPG165 with EcoRI/HindIII released a fragment of 1.9 kb containing bar. This indicated that either the HindIII site or the EcoRI site, or both, were missing or rearranged in the plasmid DNA that integrated in B16. This analysis, as well as the intensity of bar hybridization observed, indicated that B16 contained a single copy of the bar gene. It was also demonstrated in Gordon-Kamm et al. that a SmaI digest of B16 $R_0$ and $R_1$ DNA yielded a single, approximately 0.6 kb fragment that hybridized to bar, demonstrating an intact copy of bar.

Figure 2:
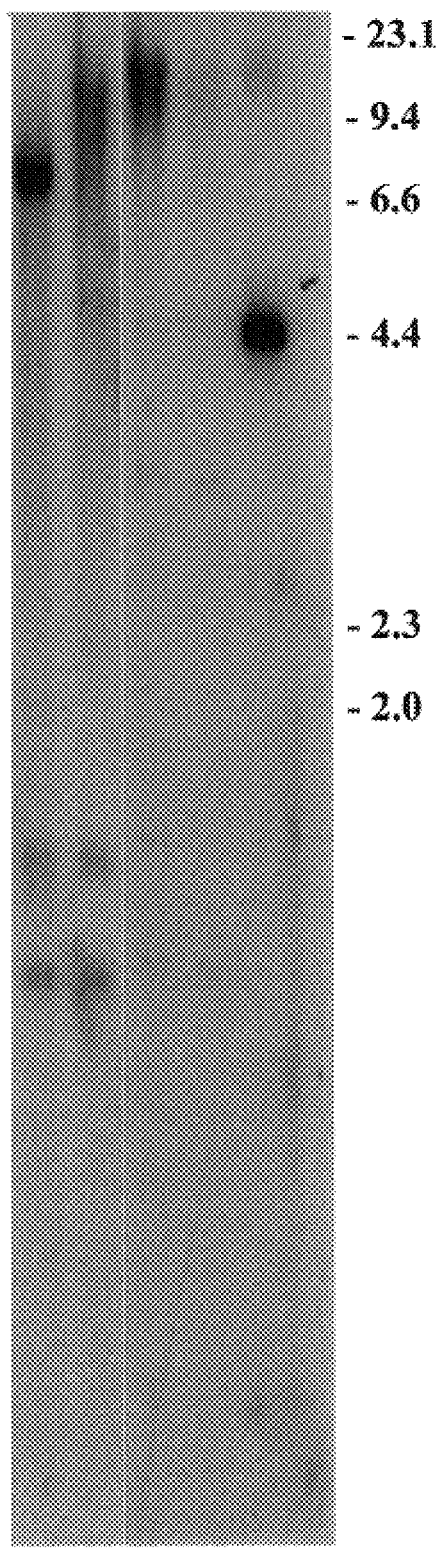
FIG. 2. Analysis of number of insertion sites in B16 by Southern blot hybridization. B16 DNA was digested with NsiI (lane 1), StuI (lane 2), or XhoI (lane 3). DNA From a nontransformed hybrid plat was digested with XhoI as a negative control (lane 4). Lane 5 contained EcoRI digested pDPG 165 loaded to represent approximately one copy of pDPG 165 per maize genome. The DNA was probed with $^{32}$P-labelled pDPG 165.
Figure 3:
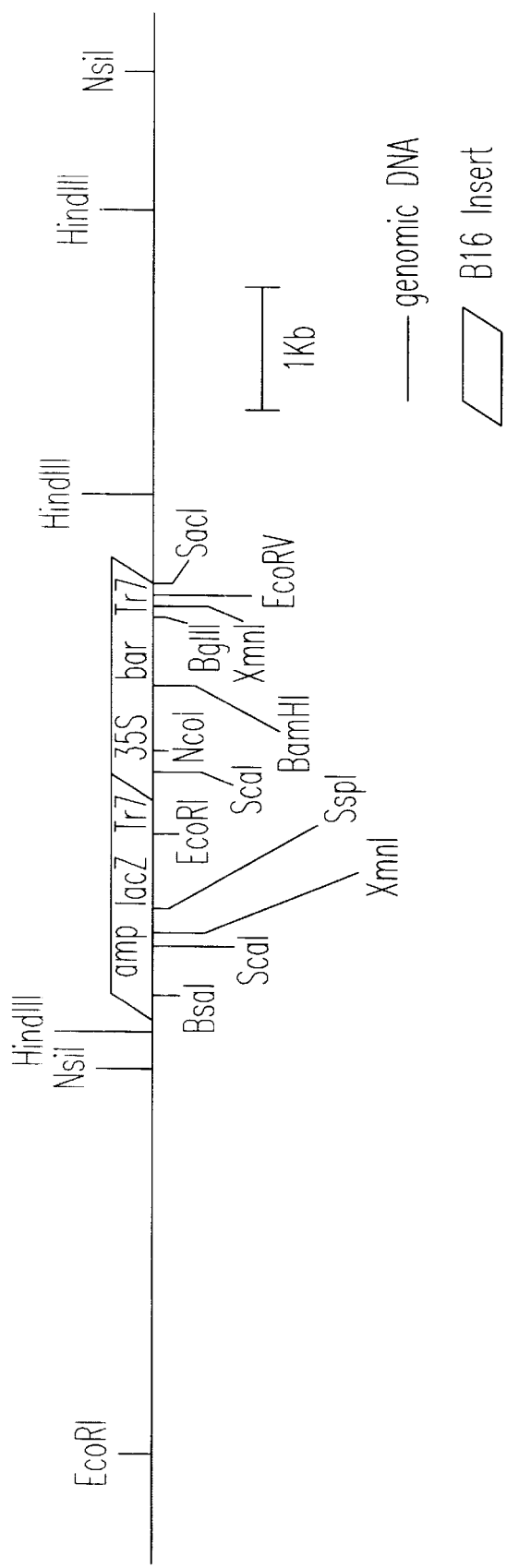
FIG. 3. Restriction map of the pDPG 165 DNA insertion and flanking maize DNA sequences in B16.

Subsequent analyses were performed using DNA isolated from plants of a hybrid line, DK591GR, into which the B16 integration event was introgressed according to Example VI. To confirm that B16 contained a single pDPG165 insertion site, B16 DNA was digested with restriction enzymes that do not cut within pDPG165, and was probed with the entire pDPG165 plasmid. Digestion of B16 DNA with two of these enzymes, XhoI and StuI, yielded pDPG165 hybridization to unresolved, high molecular weight genomic DNA. Digestion of B16 DNA with NsiI yielded a single fragment of approximately 8 kb that hybridized to pDPG165, indicative of a single insertion site (FIG. 2). A restriction map of the pDPG165 derived DNA insertion and flanking maize genomic DNA is shown in FIG. 3; this restriction map was derived from analyses described below.

Plasmid pDPG165 contains unique BamHI and BglII sites that flank the bar gene. Digestion of B16 DNA with BamHI/BglII yielded, as expected, an approximately 0.6 kb fragment that hybridized to bar. B16 and pDPG165 DNA were digested with BamHI/EcoRI or BglII/HindIII and probed with bar. Comparing the size of bar-hybridizing restriction fragments generated from B16 genomic DNA with those derived from pDPG165 demonstrated that the genomic fragments were significantly larger than the plasmid fragments. This analysis indicated that both the HindIII and EcoRI sites that flank the bar expression cassette in pDPG165 were not cutting in B16, or were missing, or were rearranged as to their original orientation to bar in pDPG165.

A series of restriction digests of B16 DNA were probed various parts of pDPG165 to map the EcoRI and HindIII sites internal to and/or flanking the pDPG165 insertion, as well as to determine specifically what parts of pDPG165 were integrated in B16. Two identical Southern blots were produced; each blot was probed with three different probes. Six pDPG165 fragments were isolated for use as probes, representing nonoverlapping pieces of the entire vector: a HindIII/BamHI fragment containing 35S, a SmaI fragment containing bar, a BglII/EcoRI fragment containing Tr7, an EcoRI/SspI fragment containing lacZ, a SspI/AlwNI fragment containing the β-lactamase gene (amp), and an AlwNI/HindIII fragment containing the ColE1 origin of replication (FIG. 1A).

Five of the six probes hybridized to B16 DNA; the probe containing the ColE1 origin of replication did not hybridize to B16 DNA, indicating that the B16 insertion lacked the AlwNI/HindIII fragment containing the ColE1 origin. Digestion of B16 DNA with NsiI/BamHI yielded two fragments that hybridized to the pDPG165 probes, one approximately 3 kb and one approximately 5 kb. The bar and 35S probes hybridized to different NsiI/BamHI fragments as expected, given that a unique BamHI site exists between bar and 35S in pDPG165 (FIG. 1A). The bar probe hybridized to the 5 kb B16 NsiI/BamHI fragment, indicating that there is a genomic NsiI site 3' to bar, approximately 5 kb from the BamHI site between 35S and bar (FIG. 3). The 35S probe hybridized to the 3 kb NsiI/BamHI fragment, indicating the presence of a genomic NsiI site about 3 kb 5' to bar (FIG. 3). The lacZ and amp probes both hybridized to the 3 kb NsiI/BamHI fragment, indicating possible fragmentation and recombination of parts of pDPG165 prior to, or during integration into B16. The Tr7 probe hybridized to both NsiI/BamHI fragments, providing further evidence for pDPG165 recombination prior to or during the B16 integration event.

Probing EcoRI-digested B16 DNA with the pDPG165 probes described above indicated that there is an EcoRI site internal to the B16 insertion, its orientation to bar being different than in pDPG165, probably due to recombination (FIG. 3). The 35S, bar, and TR7 probes hybridized to an unresolved EcoRI fragment >20 kb while the lacZ and amp probes hybridized to an EcoRI fragment of about 5 kb. This result indicated again that recombination of at least two fragments of pDPG165 had occurred, with a fragment containing at least partial copies of lacZ, amp, and Tr7 lying upstream relative to bar. The fragment containing lacZ, amp, and Tr7 appears to be in the opposite orientation to bar, as compared to the orientation in pDPG165, due to the fact that Tr7 hybridization was observed to only the B16 EcoRI fragment that hybridized to 35S and bar (FIG. 3). The data also indicates that there is a genomic EcoRI site about 5 kb upstream (relative to bar) from the internal EcoRI site.

The orientation of the recombined pDPG165 fragments in B16 was further demonstrated by the hybridization of the pDPG165 probes to an EcoRI/BamHI digest of B16 DNA. Hybridization of the 35S probe was observed to a single EcoRI/BamHI fragment of approximately 1 kb, corresponding to the small EcoRI/BamHI fragment internal to the B16 insert as the result of pDPG165 recombination (FIG. 3). The lacZ and amp probes hybridized to a 5 kb fragment in the EcoRI/BamHI digest, perhaps corresponding to the 5 kb EcoRI fragment containing the upstream plasmid-genomic DNA junction that was positive for lacZ and amp hybridization above. The bar probe hybridized to a large, unresolved (>20 kb) fragment in the B16 EcoRI/BamHI digest. This fragment contains the downstream (relative to bar) plasmid-genomic DNA junction. As would be expected, based on the restriction map in FIG. 3, the Tr7 probe hybridized to two fragments in the B16 EcoRI/BamHI digest. Tr7 hybridization was observed to the internal 1 kb EcoRI/BamHI fragment and the >20 kb downstream EcoRI/BamHI (or only BamHI) junction fragment described above (FIG. 3).

Probing a HindIII B16 digest with the pDPG165 probes revealed the same pattern of hybridization for all five probes. Two bands were observed, one approximately 4.5 kb and one approximately 6.5 kb. The single HindIII site present in pDPG165 (FIG. 1A) appears to be missing in the B16 insertion, based on the fact that probing a BglII/HindIII digest of B16 DNA with bar yielded a larger bar-hybridizing fragment than the same digest of pDPG165 (see above). This observation, along with the fact that the same HindIII restriction pattern was observed for B16 DNA, regardless of the probe, indicates that one genomic HindIII site flanking the insert may be partially digesting, perhaps the result of partial methylation, resulting in two HindIII fragments that hybridize to all five probes. This was further demonstrated by probing an EcoRI/HindIII digest of B16 DNA with the six pDPG165 probes. One fragment, approximately 1.3 kb, hybridized to the lacZ and amp probes, indicating the presence of a genomic HindIII site, 1.3 kb upstream from the internal EcoRI site (FIG. 3). Probing the EcoRI/HindIII digest with 35S, bar, and Tr7 resulted in two fragments that hybridized to all three probes, one approximately 3.2 kb and one approximately 5.2 kb. This result indicated that there is one genomic HindIII site about 3.2 kb downstream from the internal EcoRI site and this HindIII site is only partially digested. There is second genomic HindIII site 5.2 kb downstream from the internal EcoRI site (FIG. 3). In the B16 analysis described in Gordon-Kamm et al. (1990) it appears that the downstream HindIII site proximal to bar cut to completion yielding only one EcoRI/HindIII fragment of about 3.2 kb that hybridized to bar.

Several additional restriction sites, present in pDPG165, have been confirmed to be present in the B16 insert (FIG. 3). The ends of the B16 insert were more clearly defined by comparing fragment sizes in digests of pDPG165 and B16 DNA. The upstream end was more clearly defined by digesting pDPG165 and B16 DNA with EcoRI in combination with SspI, Asp700, ScaI, BsaI, or AlwNI. These digests were probed with the EcoRI/SspI lacZ fragment. The size of the hybridizing fragments from B16 digests matched those from the corresponding pDPG165 digests up to and including the BsaI site. Therefore, the upper end of the insert occurs in the approximately 700 base pair region between the BsaI and AlwNI sites of pDPG165. The downstream end of the B16 insert was mapped in a similar manner. B16 and pDPG165 DNA were digested with BamHI in combination with Asp700, EcoRV, SacI, or EcoRI. The size of the hybridizing fragments from B16 digests matched those from the corresponding pDPG165 digests down to and including SacI. The downstream end of the insert occurs in the approximately 200 base pair region between the SacI and EcoRI sites in Tr7.

B. Expression Analysis of the Transformant B16

1. Production of Purified PAT Protein

To produce and purify PAT protein, a PAT fusion protein was expressed in *E. coli*. The bar gene was isolated as an EcoRI/PstI fragment from pIJ4104 (White et al., 1990) and ligated into EcoRI/PstI digested pMAL-p1 (New England Biolabs, Beverly, Mass.). The pMAL-p1 vector contains the *E. coli* malE gene located upstream of the polylinker region into which the bar gene was cloned. Expression of the malE-bar fusion resulted in production of a maltose binding protein (MBP)::PAT fusion protein. The MBP::PAT fusion protein was expressed in *E. coli*, purified, and cleaved according to the manufacturer's recommendations. Cleavage was accomplished using the specific protease factor Xa; the pMAL-p2 vector encodes a factor Xa cleavage site just upstream of the polylinker into which bar was inserted. SDS-PAGE analysis (Laemelli, 1970) of the cleavage reaction resulted in two major protein bands as detected by Comassie staining. One band was approximately 43 kD, corresponding to the molecular weight of the maltose binding protein. The other band was approximately 22 kD, corresponding to the molecular weight of PAT (Thompson et al., 1987). The cleavage reaction was concentrated and desalted in a Microcon-10 protein concentrator (Amicon, Beverly, Mass.) and resuspended in 30 mM MOPS (3-[N-Morholino]propane-sulfonic acid) pH 8.0. The concentrated cleavage reaction was applied to a MonoQ column (Pharmacia, Piscataway, N.J.) using an FPLC system (Pharmacia). The column was washed with 30 mM MOPS pH 8.0 and eluted with a linear gradient of NaCl from 0 to 350 mM. Fractions were assayed for PAT by dot blot using a polyclonal anti-PAT antibody (see below). Dot blots were performed as described (Harlow & Lane, 1988) using a 1:200 dilution of anti-PAT followed by a 1:2000 dilution of anti-rabbit IgG-peroxidase (Boehringer Mannheim, Indianapolis, Ind.) and visualized calorimetrically using chloronapthol (Harlow & Lane, 1988). Fractions exhibiting antigenicity eluted between 100–200 mM NaCl. These fractions were tested for purity by Western blot and pooled.

2. Production of Anti-PAT Antibody

Approximately 1500 µg of PAT protein was gel-purified (SDS-PAGE) following proteolytic cleavage of the MBP: :PAT fusion protein. Gel slices containing PAT were sent to East Acres Biologicals (Southbridge, Mass.) for preparation of rabbit anti-PAT antibody. Using Western blots (see below), purified IgG fractions were tested and found to have immunoaffinity for cleaved PAT fusion protein and PAT produced in plant tissues expressing the bar gene.

3. Quantification of PAT in B16 Plants

Tissue samples from various plant tissues were weighed and ground fresh in sintered glass homogenizers with 100–500 µl of extraction buffer. (150 mM NaCl, 1% NP-40 (octylphenoxypolyetoxyethanol), 0.1% SDS, 50 mM Tris HCl pH 8.0). Extracts were clarified by microcentrifugation for five minutes. Total soluble protein in the extracts was quantified according to Bradford (1976). Fifteen to 250 µg of protein from B16 plant extracts were electrophoresed (SDS PAGE) with purified PAT standards for quantification. Five to seven PAT standards, representing a range of ten to 200 µg, were loaded per gel to generate a standard curve. For Western blotting, proteins were electrophoretically transferred to nitrocellulose using a semi-dry electroblotter (Integrated Separation Systems, Enprotech, Inc., Hyde Park, Mass.). Nitrocellulose protein blots were washed for ten minutes in 50 ml of 1×TBS/ 0.3% Tween-20 (TBS/T). Blots were then incubated in 50 ml of 5% non-fat dry milk/TBS/T containing a 1:500 dilution of anti-PAT antibody for one hour, followed by 4×50 ml washes in milk/TBS/T for ten minutes each. Blots were incubated in 50 ml of milk/TBS/T and a 1:2000 dilution of anti-rabbit IgG-peroxidase (Boehringer Mannheim) for one hour and washed three times for ten minutes each in milk/TBS/T and one final wash in TBS/T. PAT protein on Western blots was visualized using the Enhanced Chemiluminescent System (ECL) from Amersham (Arlington Heights, Ill.). Autoradiograms produced using the ECL system were scanned and quantitation was accomplished using Whole Band Analysis on Bio Image software on a Sun SPARCstation IPC computer (hardware and software package supplied by Millipore Corporation, Bio Image Products, Ann Arbor, Mich.). Standards were plotted using Sigma Plot (Jandel Scientific, San Rafael, Calif.) and linear regression analysis and interpolation of experimental values was accomplished using Lotus 123 software (Lotus Development Corporation, Cambridge, Mass.).

PAT levels were initially determined in leaf tissue of several different hybrids that were converted with the B16 transformation event. PAT levels were fairly consistent from hybrid to hybrid, ranging from 0.5–1 ng of PAT per µg of total soluble protein in the five hybrids tested. One hybrid line converted with the B16 transformation event, DK591, was chosen for further analysis. A summary of PAT levels observed in various B16/DK591 tissues is shown in Table 1. PAT levels were highest in vegetative tissues, based on ng/µg total soluble protein. PAT levels detected in coleoptile, leaf, root, prop root, stalk, cob, and husk were in the range of 1–4.6 ng PAT per µg of total soluble protein. This range corresponds to 0.1–0.46% of total soluble protein. PAT levels determined in a developmental analysis of $F_2$ seed ranged from 0.8 ng/µg total soluble protein in unfertilized ovules to less than 0.1 ng/µg of total soluble protein in mature seed (a band was apparent but below the lowest standard). No PAT protein was detected in B16/DK591 pollen or hybrid seed.

TABLE 3

PAT Levels in Various B16/DK591 Tissues Determined by Western Blotting.

| Tissue (age) | PAT concentration (ng/µg total protein) proteprotein) in( | PAT concentration (ng/mg fresh weight) |
|---|---|---|
| Coleoptile (6 days) | 1.8 ng/µg | 13.8 ng/mg |
| Leaf (24 days) | 1.0 ng/µg | 55.6 ng/mg |
| Leaf (44 days) | 2.8 ± 0.1 ng/µg | 166.0 ± 24.2 |
| Leaf (93 days) | 2.1 ng/µg | 106.1 ng/mg |
| $F_2$ ovule (0 days pp) | 0.8 ng/µg | 5.5 ng/mg |
| Immature $F_2$ seed (16 | 0.3 ng/µg | 3.4 ng/mg |
| Immature $F_2$ seed (27 | 0.3 ng/µg | 5.7 ng/mg |
| Mature dry $F_2$ seed (45 | <0.1 ng/µg | |
| zHybrid seed ($F_1$) | not detecteda | |
| Root (24 days) | 1.3 ng/µg | 8.1 ng/mg |
| Root (44 days) | 1.9 ± 0.3 ng/µg | 19.8 ± 2.4 ng/mg |
| Prop root (49 days) | 2.4 ng/µg | 67.2 ng/mg |
| Cob (56 days) | 2.2 ng/µg | 2.5 ng/mg |
| Husk (56 days) | 1.1 ng/µg | 4.2 ng/mg |
| Silk | not detected[a] | |
| Stalk (24 days) | 2.0 ng/µg | 15.7 ng/mg |
| Stalk (77 days) | 4.6 ± 0.4 ng/µg | 11.2 ± 2.7 ng/mg |
| Immature tassel (49 | 2.0 | 30.8 ng/mg |
| Pollen | not detected[b] | |

[a]<0.05 ng/µg
[b]<0.08 ng/µg

C. Isolation of Maize Genomic DNA Sequences Situated Adjacent to pDPG165 DNA Sequences in the B16 Integration Event The maize genomic DNA sequences that are situated adjacent to pDPG165 DNA sequences in the B16 integration event are isolated using various techniques that are familiar to a practitioner of skill in the art.

1. Polymerase Chain Reaction (PCR) Techniques

DNA sequences flanking pDPG165 plasmid sequences in transformant B16 are cloned using polymerase chain reaction (PCR) techniques, including RAGE (rapid amplification of genomic ends) and IPCR (Inverse PCR). It is anticipated that other PCR methods may be useful for cloning of genomic DNA sequence adjacent to a plasmid integration site and are familiar to a practitioner of skill in the art.

Maize genomic DNA sequences adjacent to the B16 integration event described herein are cloned using rapid amplification of genomic DNA ends (RAGE) (Mizobuchi & Frohman, 1993). The restriction map of the B16 integration event (FIG. 3) provides information as to DNA sequences that are present in the pDPG165 derived portion of the B16 integration event and that are situated immediately adjacent to maize genomic DNA sequences. It is possible using the software oligo™, and inputting DNA sequences derived from pDPG165 that are adjacent to maize genomic DNA sequences in the B16 integration event and DNA sequences from the plasmid vector that is used in the RAGE technique, to design a pair of matched oligonucleotide primers that following PCR using the RAGE technique will generate a DNA fragment that will begin in pDPG165 derived sequences, span adjacent maize genomic DNA sequences, and end in DNA sequences derived from the plasmid vector that was used in the RAGE technique. Using this technique it is necessary to design oligonucleotide primers for RAGE that will begin in each of the two ends of the integrated pDPG165 derived DNA, span maize genomic DNA on either end of the integrated plasmid DNA sequences and terminate in RAGE plasmid DNA. As a result of using the RAGE technique, two PCR DNA products are produced, and each PCR product contains maize genomic DNA sequences that are located adjacent to pDPG165 sequences in the B16 integration event. A practitioner of skill in the art optimizes the PCR amplification protocol so as to maximize the yield of desirable DNA product and minimize the production of non-specific DNA products. Sambrook et al. (1989) provide instruction for optimization of PCR amplification of DNA.

Alternatively, maize genomic DNA sequences adjacent to the B-16 integration event described herein are cloned using Inverse PCR (IPCR) (Ochman et al., 1990). The restriction map of the B16 integration event (FIG. 3) provides information as to DNA sequences that are present in the pDPG165 derived portion of the B16 integration event and that are situated immediately adjacent to maize genomic DNA sequences. It is possible using the software Oligo™, and inputting DNA sequences derived from pDPG165 that are adjacent to maize genomic DNA sequences in the B16 integration event, to design a pair of matched oligonucleotide primers that following PCR using the IPCR technique with generate a DNA fragment that will begin in pDPG165 derived sequences, span ligated adjacent maize genomic DNA sequences, and end in pDPG165 derived sequences. Using this technique it is necessary to design oligonucleotide primers for IPCR that will begin in each of the two ends of the integrated pDPG165 derived DNA sequences and result in amplification of genomic DNA on either end of the insertion that is ligated together using the IPCR technique. As a result of using the IPCR technique, a single PCR DNA product is produced, and the PCR product contains maize genomic DNA sequences that are located adjacent to pDPG165 sequences in the B16 integration event. A practitioner of skill in the art optimizes the PCR amplification protocol so as to maximize the yield of desirable DNA product and minimize the production of non-specific DNA products. Sambrook et al. (1989) provide instruction for optimization of PCR amplification of DNA.

2. Plasmid Based Cloning

The restriction enzyme digestion map of the B16 integration event (FIG. 3) provides sufficient information for a practitioner of skill in the art to clone flanking maize DNA sequences in the B16 integration event from a plasmid library. The maize genomic DNA sequences flanking each side of the pDPG165 derived sequences in the B16 integration event are cloned separately, because it is difficult to clone large DNA fragments in plasmid vectors. For example, approximately five kilobase pair EcoRI DNA fragments produced following restriction enzyme digestion of maize genomic DNA containing the B16 integration event are enriched using gel electrophoresis and said EcoRI DNA fragments are cloned in a plasmid vector. The plasmid library produced is screened by hybridization to the amp or lacZ gene. A clone is identified that contains the amp and lacZ genes derived from pDPG165 and approximately 3.5 kilobases of maize genomic DNA which flanks said pDPG165 DNA in the B16 integration event. Similarly, flanking maize DNA from the opposite end of the B16 integration event is cloned from gel electrophoresis enriched approximately 5 kilobase pair NsiI-BamHI DNAs fragments derived from restriction enzyme digested B16 genomic cloned in a plasmid vector. A clone is identified by screening said NsiI-BamHI plasmid library with the bar gene which contains the bar gene and approximately 4 kilobases of flanking maize genomic DNA.

DNA fragments generated from other restriction enzyme digestions are also cloned in plasmid libraries. The fragments cloned are those DNA elements which based on the restriction enzyme digestion map of the B16 insertion event will produce a cloned DNA fragment that contains DNA derived from pDPG165 and flanking maize genomic DNA. Sambrook et al. (1989, incorporated herein by reference) provide detailed instructions for production of plasmid libraries and identification of DNA sequences from said libraries.

3. λ Phage Cloning

The methods described above for cloning of flanking maize DNA fragments using a plasmid library are followed except a λ phage library prepared from B16 genomic DNA is used. Because a recombinant λ phage contains a larger DNA insert than is possible in a phage, the B16 insertion event is also cloned as a single DNA fragment containing pDPG165 derived DNA sequences and maize DNA flanking both sides of the pDPG165 insert. A method of cloning a DNA of unknown sequence which is located adjacent to a second DNA element of known sequence are disclosed in U.S. Pat. No. 4,732, 856 (incorporated herein by reference). Sambrook et al. (1989, incorporated herein by reference) provide detailed instructions for production of λ phage libraries and identification of DNA sequences from said libraries.

4. Isolation of Intact Maize DNA Sequence into which pDPG165 DNA Sequences Were Integrated A λ phage library is prepared from maize genomic DNA that does not contain the B16 integration event. Said λ library is screened using genomic DNA that flanks the B16 integration event which was isolated using RAGE or plasmid or λ phage libraries as described herein. A λ clone is identified which contains the intact maize genomic DNA sequence into which pDPG165 was integrated in the B16 transformation event. Sambrook et al. (1989, incorporated herein by reference) provide detailed instructions for production of λ phage libraries and identification of DNA sequences from said libraries.

EXAMPLE VI

Introgression of a Gene Encoding Phosphinothricin Acetyltransferase into Elite Inbreds of Maize Backcrossing can be used to improve an inbred plant. Backcrossing transfers a specific desirable trait from one inbred source to an inbred that lacks that trait. This can be accomplished, for example, by first crossing a superior inbred (A) (recurrent parent) to a donor inbred (non-recurrent parent), which carries the appropriate gene(s) for the trait in question. The progeny of this cross are then mated back to the superior recurrent parent (A) followed by selecting in the resultant progeny for the desired trait to be transferred from the non-recurrent parent. After five or more backcross generations with selection for the desired trait, the progeny are heterozygous for loci controlling the characteristic being transferred, but are like the superior parent for most or almost all other genes. The last backcross generation would be selfed to give pure breeding progeny for the gene(s) being transferred.

Therefore, through a series of breeding manipulations, a selected gene encoding phosphinothricin acetyltransferase may be moved from one corn line into an entirely different corn line without the need for further recombinant manipulation. Introduced transgenes are valuable in that they behave genetically as any other corn gene and can be manipulated by breeding techniques in a manner identical to any other corn gene. Exemplary procedures of this nature have been successfully carried out by the inventors. In these backcrossing studies, the transformant B16 as well as two other transformants were introgressed into three elite inbred lines by backcrossing. It is possible from these three inbreds to make a large number of hybrids of commercial importance. Seven of the possible hybrids have been made and were field tested for yield and other agronomic characteristics and herbicide tolerance. Additional backcrossing to a further 116 inbred lines is underway.

The elite inbreds FBLL and FBLA were backcrossed five times to the B16 transformant. A third inbred, 78551, was backcrossed six times to the B16 transformant. These three inbreds comprise one parent of each of seven elite commercial corn hybrids. At each backcross generation plants containing the bar gene were identified based on resistance to phosphinothricin. Following five generations of backcrossing to a recurrent elite inbred parent, it is anticipated that the transformed line will be present in a genetic background that is at least 97% identical to the recurrent parent. Following backcross conversion, the plants were self-pollinated twice in order to identify plants homozygous for the introgressed gene of interest, i.e., the B16 insertion event. Hybrids were produced by crossing two inbred parents, one of which contained the introgressed B16 insertion event.

EXAMPLE VII

Yield Analysis of a Transformant Containing a Gene Encoding Phosphinothricin Acetyltransferase A. Field Design Seven hybrids containing the B16 transformation event were field tested for yield and other agronomic traits. These hybrids are referred to as GR hybrids and were produced according to the methods of Example VI. Yield data was collected from the hybrids.

The study was arranged in a split plot design. The main plots consisted of hybrids and each main plot spanned two rows and four ranges. Treatments were randomly assigned for each hybrid to the two-row subplot in each range. Treatments were: 1) the unconverted hybrid, unsprayed, 2) the converted hybrid, 0X rate of phosphinothricin (i.e. water only), 3) the converted hybrid, 1X rate of phosphinothricin, and 4) the converted hybrid, 4X rate of phosphinothricin. The 1X field application rate is 0.40 kg active ingredient/hectare. Main plots were separated by two rows of buffer to absorb spray drift. So within one range, there were two rows of experimental material, two rows of buffer, two rows of experimental material, etc. The total width of one repeat depended on the number of hybrids to be tested at each location. Two hybrids were tested at the locations in Group A, five hybrids at Group B locations and five hybrids at Group C locations. Thus, one repeat of the study without surrounding borders was four ranges long and six, 22, or 30 rows wide for Group A, Group B, and Group C, respectively. The study was replicated three times. The replicates were stacked or arranged side-by-side. A sample field design map is shown in FIG. 4.

Field studies were grown under standard agronomic conditions at 12 locations in Indiana, Tennessee, Illinois, Wisconsin, Minnesota, Iowa, and Nebraska. The early hybrids (DK 381 and DK 485) were grown at locations in the 100–105 relative maturity range, whereas the mid-maturity hybrids (DK 512, DK 554, DK 580, DK 591, and DK 623) were grown at locations in the 105–120 relative maturity range. Limited seed quantities of DK 554GR restricted the number of sites including versions of DK 554. Data from sites where there were adverse environmental conditions during the growing condition were excluded from the combined analysis. The following traits were evaluated: shelled grain weight, grain moisture at harvest, test weight, dropped ears, stalk lodging, root lodging, barrenness, stay green, intactness, seedling vigor, plant height, ear height, 50% pollen shed, 50% silking, and greensnap. Test weight estimates were obtained using meters installed on the combines. Stay green, intactness, and seedling vigor were rated on a 1 to 9 scale, with 9 representing the most favorable rating. Yield estimates were computed using the shelled grain weights, adjusted to 15.5% moisture. The percentages of plants not exhibiting dropped ears, stalk lodging, root, lodging, or barrenness were computed based on final stand counts for each subplot. Silk delay was calculated for each entry as the interval between 505 pollen shed and 50% silking. Data were analyzed using the SAS GLM procedure. Only hybrids to which no phosphinothricin was applied were compared in order to remove any effects of herbicide application rates and/or weed competition on grain yield. The discussion herein will concentrate on results relating to grain yield.

When all hybrids and locations were averaged, the increase in grain yield was about 4.8 bushes/acre (Table 4). T-test analysis of the data indicated that the yield increase over the unconverted hybrids, which do not contain a gene encoding PAT, is statistically significant. Furthermore, there is a 99% confidence interval that the increase in yield in the tested hybrids is between 1.25 and 8.35 bushels/acre. Furthermore, there is a statistically significant increase in seedling vigor in GR hybrids. Table 5, however, indicates that there was a larger increase in yield in certain hybrids, e.g., DK485 and DK512, and negligible yield increases in other hybrids, e.g., DK 591. Across all locations the yield increase averaged up to over 10 bushels per acre depending on the particular hybrid analyzed. The objective of backcross conversions is to recover the genotype of the recurrent parent plus the trait to be introgressed. Following five backcross generations, converted lines are expected to contain greater than 98% recurrent germplasm and are therefore expected to perform similarly to the unconverted hybrid. Therefore, it is common following backcross conversions for hybrids to demonstrate yields that are randomly distributed around the unconverted hybrid mean. It is indeed unexpected to observe the means for yield of hybrids produced from nine different backcross converted inbreds to all be increased relative to the unconverted control hybrid, and this result certainly indicates that the hybrid containing a phosphinothricin acetyltransferase gene tends to have higher yield. Although the yield increases for only the individual hybrids DK 485 and DK 512 were statistically significant, the results when averaged across all locations and all hybrids indicated that the presence of a phosphinothricin acetyltransferase gene in these hybrids leads to a statistically significant increase in yield.

TABLE 4

Agronomic Performance of Hybrids Compared to The Counterpart Hybrids with the B16 Integration Event Introgressed

| Trait | N | Increase in GR Hybrid | SE |
| --- | --- | --- | --- |
| Yield (bu/A) | 137 | 4.8** | 1.38 |
| Grain Moisture (%) | 137 | 0.1 | 0.09 |
| Test Weight (#/bu) | 85 | 0.2 | 0.13 |

TABLE 4-continued

Agronomic Performance of Hybrids Compared to The Counterpart Hybrids with the B16 Integration Event Introgressed

| Trait | N | Increase in GR Hybrid | SE |
|---|---|---|---|
| Not Ear Dropped (%) | 137 | −0.1 | 0.04 |
| Not Stalk Lodged (%) | 137 | 0 | 0.19 |
| Not Root Lodged (%) | 137 | 0 | 0.11 |
| Not Barren (%) | 81 | 0.6 | 0.44 |
| Intactness (1-9) | 76 | −0.5 | 0.83 |
| Seedling Vigor (1-9) | 95 | 0.5** | 0.09 |
| Plant Height (in.) | 138 | 1.3** | 0.42 |
| Ear Height (in.) | 111 | 0.1 | 0.49 |
| 50% Pollen Shed (gdu) | 119 | 1.2 | 2.21 |
| 50% Silk (gdu) | 80 | 1.5 | 3.28 |
| Silk Delay (gdu) | 80 | 1.4 | 2.28 |
| Stay Green (1-9) | 118 | 0.1 | 0.09 |
| Green Snap (%) | 34 | 0.3 | 1.94 |

**Indicates that the mean difference is greater than zero at the α = 0.01 level of significance.

TABLE 5

GR Hybrid Yield Performance Relative to Unconverted Counterpart

| Hybrid | Yield (bu/A) | Increase In Yield |
|---|---|---|
| DK381 | 149.7 | |
| DK381GR | 152.7 | 3.0 |
| DK485 | 155.8 | |
| DK485GR | 166.3** | 10.5 |
| DK512 | 159.6 | |
| DK512GR | 168.8** | 9.2 |
| DK554 | 164.6 | |
| DK554GR | 167.3 | 2.7 |
| DK580 | 171.7 | |
| DK580GR | 180.0 | 8.3 |
| DK591 | 183.2 | |
| DK591GR | 183.3 | 0.1 |
| DK623 | 166.4 | |
| DK623GR | 169.3 | 2.9 |

No herbicide application to GR hybrids.
**indicates a difference from the mean of the unconverted version at the 0.01 level of significance.

Table 6 shows data in a hybrid by hybrid and location by location fashion. Three separate analyses of these data were conducted depending on the number of locations at which a set of hybrids were tested, i.e., data set one comprised DK 381 and DK485 at 5 locations, data set two comprised DK 512, DK 580, DK 591, and DK 623 at 9 locations, and data set three comprised DK 512, DK 554, DK 580, DK 591, and DK 623 at 3 locations. Yield differences between the unconverted and GR hybrids were significant at the 0.99 confidence level in analysis of the data comprising set one and set two. Numerically, the GR hybrid version of DK 554 out yielded the unconverted hybrid, but the power of the test was not significant to detect statistical differences, i.e., there were not enough observations. The statistical significance of the yield increases in data sets one and two and the numerical increase in the yield in data set three indicated that there was a yield increase in GR hybrids. The yield increase observed in the GR hybrids was not an artifact produced by the backcross conversion program as these same GR hybrids showed no significant differences for grain moisture, test weight, ear drop, stalk lodging, root lodging, barrenness, stay green, intactness, seedling vigor, plant height, ear height, time to 50%. pollen shed, time to 50% silking, silk delay, and green snap. Therefore, the only observed change in agronomic performance in GR hybrids in the absence of herbicide application was a significant increase in grain yield.

TABLE 6

Yield Performance of Unconverted and GR Hybrids (Unsprayed) By Location (bu/A)

| Hybrid | Location | Unconverted Hybrid | GR Hybrid | Increase In Yield |
|---|---|---|---|---|
| DK381 | Waterman, IL | 127.9 | 126.3 | −1.6 |
| | Dayton, IA | 141.4 | 153.4 | 12.0 |
| | Owatonna, MN (1) | 156.5 | 153.1 | −2.8 |
| | Owatonna, MN (2) | 152.8 | 152.5 | −0.3 |
| | Olivia, MN | 170.1 | 177.5 | 7.4 |
| DK485 | Waterman, IL | 154.9 | 159.1 | 4.2 |
| | Dayton, IA | 159.0 | 164.7 | 5.7 |
| | Owatonna, MN (1) | 147.4 | 158.1 | 10.7 |
| | Owatonna, MN (2) | 140.4 | 154.1 | 13.7 |
| | Olivia, MN | 177.1 | 195.3 | 18.2 |
| DK512 | Waterman, IL | 164.7 | 171.7 | 7.0 |
| | Dayton, IA | 169.2 | 178.8 | 9.6 |
| | Windfall, IN | 142.4 | 150.8 | 8.4 |
| | Atlantic, IA | 210.1 | 197.8 | −12.3 |
| | Mason City, IL | 172.1 | 179.1 | 7.0 |
| | North Liberty, IA | 173.6 | 172.6 | −1.0 |
| | Union City, TN | 113.9 | 139.6 | 25.7 |
| | Washington, IN | 153.4 | 182.3 | 28.9 |
| | Thomasboro, IL | 137.1 | 146.8 | 9.7 |
| DK554 | Waterman, IL | 145.9 | 157.8 | 11.9 |
| | Dayton, IA | 171.4 | 173.0 | 1.6 |
| | Windfall, IN | 176.5 | 171.0 | −5.5 |
| DK580 | Waterman, IL | 163.4 | 173.9 | 10.5 |
| | Dayton, IA | 177.9 | 182.0 | 4.1 |
| | Windfall, IN | 173.4 | 185.7 | 12.3 |
| | Atlantic, IA | 218.2 | 191.9 | −26.3 |
| | Mason City, IL | 190.8 | 172.7 | −18.1 |
| | North Liberty, IA | 211.0 | 199.1 | −11.9 |
| | Union City, TN | 136.5 | 150.6 | 14.1 |
| | Washington, IN | 179.6 | 201.0 | 21.4 |
| | Thomasboro, IL | 152.8 | 150.5 | −2.3 |
| DK591 | Waterman, IL | 167.7 | 171.0 | 3.3 |
| | Dayton, IA | 176.7 | 176.8 | 0.1 |
| | Windfall, IN | 202.1 | 180.6 | −21.5 |
| | Atlantic, IA | 237.0 | 223.3 | −13.7 |
| | Mason City, IL | 198.8 | 183.4 | −15.4 |
| | North Liberty, IA | 206.6 | 211.4 | 4.8 |
| | Union City, TN | 134.1 | 146.6 | 12.5 |
| | Washington, IN | 191.5 | 200.6 | 9.1 |
| | Thomasboro, IL | 140.5 | 155.8 | 15.3 |
| DK623 | Waterman, IL | 169.5 | 163.7 | −5.8 |
| | Dayton, IA | 173.4 | 181.5 | 8.1 |
| | Windfall, IN | 146.4 | 152.2 | 5.8 |
| | Atlantic, IA | 165.1 | 182.9 | 17.8 |
| | Mason City, IL | 184.7 | 162.3 | −22.4 |
| | North Liberty, IA | 196.9 | 206.4 | 9.5 |
| | Union City, TN | 125.4 | 146.2 | 20.8 |
| | Washington, IN | 193.7 | 206.4 | 12.7 |
| | Thomasboro, IL | 121.8 | 121.9 | 0.1 |

EXAMPLE VIII

Marker Assisted Breeding

The identification of maize lines that are bred for increased yield may be readily assisted by using a PAT gene integration event preferably the B16 integration event, as presently disclosed, as well as other integration events involving a gene encoding phosphinothricin acetyltransferase as identified using the methods of the present invention. Techniques for isolating nucleic acids and proteins are well known to those of skill in the art (Sambrook et al., 1989), and may be used in conjunction with the integration events of the present invention to selectively segregate plants that have increased yield.

It is contemplated that PAT gene integration events will be useful as DNA probes for marker assisted breeding. In the process of marker assisted breeding DNA sequences are used to follow desirable agronomic traits (Tanksley et al., 1989) in the process of plant breeding. It is anticipated that a PAT gene integration event probe will be useful for identification of plants with enhanced yield.

Marker assisted breeding using a PAT gene integration event is undertaken as follows. Seed of plants with the desired yield are planted in soil in the greenhouse or in the field. Leaf tissue is harvested from the plant for preparation of DNA at any point in growth at which approximately one gram of leaf tissue can be removed from the plant without compromising the viability of the plant. Genomic DNA is isolated using a procedure modified from Shure et al. (1983). Approximately one gram of leaf tissue from a seedling is lypholyzed overnight in 15 ml polypropylene tubes. Freeze-dried tissue is ground to a powder in the tube using a glass rod. Powdered tissue is mixed thoroughly with 3 ml extraction buffer (7.0 M urea, 0.35 M NaCI, 0.05 M Tris-HCI ph 8.0, 0.01 M EDTA, 1% sarcosine). Tissue/buffer homogenate is extracted with 3 ml phenol/ chloroform. The aqueous phase is separated by centrifugation, and precipitated twice using 1/10 volume of 4.4 M ammonium acetate pH 5.2, and an equal volume of isopropanol. The precipitate is washed with 75% ethanol and resuspended in 100–500 µl TE (0.01 M Tris-HCI, 0.001 M EDTA, pH 8.0). Genomic DNA is digested with a 3-fold excess of restriction enzymes, electrophoresed through 0.8% agarose (FMC), and transferred (Southern, 1975) to Nytran (Schleicher and Schuell) using 10×SCP (20×SCP: 2 M NaCI, 0.6 M disodium phosphate, 0.02 M disodium EDTA).

One of skill in the art will recognize that many different restriction enzymes will be useful and the choice of restriction enzyme will depend on the DNA sequence of the PAT gene integration event that is used as a probe and the DNA sequence in the maize genome surrounding the PAT gene integration event. One will select a restriction enzyme that produces a DNA fragment following hybridization that is identifiable as that PAT gene integration event. Table 7 lists a number of exemplary restriction enzymes and their target sequences.

It is expected that one or more restriction enzymes will be used to digest genomic DNA either singly or in combinations. Filters are prehybridized in 6×SCP, 10% dextran sulfate, 2% sarcosine, and 500 µl g/ml denatured salmon sperm DNA and $^{32}$P-labelled wilt gene probe generated by random priming (Feinberg & Vogelstein, 1983). Hybridized filters are washed in 2×SCP, 1% SDS at 65° for 30 minutes and visualized by autoradiography using Kodak XAR5 film. Those of skill in the art will recognize that there are many different ways to isolate DNA from plant tissues and that there are many different protocols for Southern hybridization that will produce identical results. Those of skill in the art will recognize that a Southern blot can be stripped of radioactive probe following autoradiography and reprobed with a different PAT gene integration event probe. In this manner one identifies each of the various PAT gene integration events that is present in the plant.

TABLE 7

RESTRICTION ENZYMES

| Aat II | GACGT/C | BspH I | T/CATGA |
|---|---|---|---|
| Acc I | GT/MKAC | BspM I | ACCTGC (4/8) |
| Acc II | GC/CG | BspM II | T/CCGGA |
| Acc III | T/CCGGA | Bsr I | ACTGG (1/−1) |
| Aci I | CCGC (2/2) | BsrB I | GAGCGG (−3/−3) |
| Acy I | GR/CGYC | BstE II | G/GTNACC |
| Afl II | C/TTAAG | BstN I | CC/WGG |

TABLE 7-continued

RESTRICTION ENZYMES

| Afl III | A/CRYGT | BstX I | CCANNNNN/NTGG |
|---|---|---|---|
| Age I | A/CCGGT | Cac8 I | GCN/NGC |
| Aha III | TTT/AAA | Cau II | CC/SGG |
| Alu I | AG/CT | Cfr I | Y/GGCCR |
| AlwN I | CAGNNN/CTG | Cfr10 I | R/CCGGY |
| Aoc I | CC/TNAGG | Cla I | AT/CGAT |
| Apa I | GGGCC/C | CviJ I | RG/CY |
| ApaB I | GCANNNN/TGC | CviR I | TG/CA |
| ApaL I | G/TGCAC | Dde I | C/TNAG |
| Asc I | GG/CGCGCC | Dpn I | GA/TC |
| Asu I | G/GNCC | Dra I | TTT/AAA |
| Asu II | TT/CGAA | Dra II | RG/GNCCY |
| Ava I | C/YCGRG | Dra III | CACNNN/GTG |
| Ava II | G/GWCC | Drd I | GACNNNN/NNGTC |
| Ava III | ATGCAT | Drd II | GAACCA |
| Avr III | C/CTAGG | Dsa I | C/CRYGG |
| Bae I | ACNNNNGTAYC | Ema1105 I | GACNNN/NNGTC |
| Bal I | TGG/CCA | Eci I | TCCGCC |
| BamH I | G/GATCC | Eco3 II | GGTCTC (1/5) |
| Bbv I | GCAGC (8/12) | Eco47 III | AGC/GCT |
| Bbv II | GAAGAC (2/6) | Eco52 I | C/GGCCG |
| Bcc I | CCATC | Eco57 I | CTGAAG (16/14) |
| Bcef I | ACGGC (12/13) | EcoN I | CCTNN/NNNAGG |
| Bcg I | GCANNNNNNCG (12/10) | EcoR I | G/AATTC |
| Bcl I | T/GATCA | EcoR II | /CCWGG |
| Bet I | W/CCGGW | Ecor V | GAT/ATC |
| Bgl I | GCCNNNN/NGGC | Esp I | GC/TNAGC |
| Bgl II | A/GATCT | Esp3 I | CGTCTC (1/5) |
| Bin I | GGATC (4/5) | Fau I | CCCGC (4/6) |
| Bpu10 I | CCTNAGC (−5/2) | Fin I | GTCCC |
| Bpu1102 I | GC/TNAGC | Fnu4H I | GC/NGC |
| Bsp1286 I | GDGCH/C | FnuD II | CG/CG |
| Bsp106 I | AT/CGAT | Fok I | GGATG (9/13) |
| BspC I | CGAT/CG | Fse I | GGCCGG/CC |
| BsaA I | YAC/GTR | Fsi I | R/AATTY |
| BasB I | GATNN/NNATC | Gdi II | YGGCCG (−5/−1) |
| BseP I | GCGCGC | Gsu I | CTGGAG (16/14) |
| Bsg I | GTGCAG (16/14) | Hae I | WGG/CCW |
| Bsi I | CTCGTG (5/1) | Hae II | RGCGC/Y |
| BsiY I | CCNNNNN/NNGG | Hae III | GG/CC |
| Bsm I | GAATGC (1/−1) | Hga I | GACGC (5/10) |
| BsmA I | GTCTC (1/5) | HgiA I | GWGCW/C |
| Bsp50 I | CG/CG | HgaC I | G/GYRCC |
| BspG I | CG/CGCTGGAC | HgiE II | ACCNNNNNNGGT |
| HgiJ II | GRGCY/C | Pst I | CTGCA/G |
| Hha I | GCG/C | Pvu I | CGAT/CG |
| Hind II | GTY/RAC | Pvu II | CAG/CTG |
| Hind III | A/AGCTT | RleA I | CCCACA (12/9) |
| Hinf I | G/ANTC | Rsa I | GT/AC |
| Hinl I | GY/CGYC | Rsr II | CG/GWCCG |
| Hpa I | GTT/AAC | Sac I | GAGCT/C |
| Hpa II | C/CGG | Sac II | CCGC/GG |
| Hph I | GGTGA (8/7) | Sal I | G/TCGAC |
| Kpn I | GGTAC/C | Sap I | GCTCTTC (1/4) |
| Ksp632 I | CTCTTC (1/4) | Sau3A I | /GATC |
| Ksp I | CCGC/GG | Sau96 I | G/GNCC |
| Mae I | C/TAG | Sau I | CC/TNAGG |
| Mae II | A/CGT | Sca I | AGT/ACT |
| Mae III | /GTNAC | ScrF I | CC/NGG |
| Mbo I | /GATC | Sdu I | GDGCH/C |
| Mbo II | GAAGA (8/7) | Sec I | C/CNNGG |
| Mcr I | CGRY/CG | SfaN I | GATC (5/9) |
| Mfe I | C/AATTG | Sfc I | CTYRAG |
| Mlu I | A/CGCGT | Sfe I | C/TYRAG |
| Mly I | GACTC (5/5) | Sfi I | GGCCNNNN/NGGCC |
| Mme I | TCCRAC (20/18) | SgrA I | CR/CCGGYG |
| Mnl I | CCTC (7/7) | Sma I | CCC/GGG |
| Mse I | T/TAA | Sna I | GTATAC |
| Msp I | C/CGG | SnaB I | TAC/GTA |
| Mst I | TGC/GCA | Spe I | A/CTAGT |
| Mst II | CC/TNAGG | Sph I | GCATG/C |
| Mwo I | GCNNNNN/NNGC | Spl I | C/TGACG |
| Nae I | GCC/GGC | Srf I | GCCC/GGGC |

TABLE 7-continued

RESTRICTION ENZYMES

| | | | |
|---|---|---|---|
| Nar I | GG/CGCC | Sse838 I | CCTGCA/GG |
| Nci I | CC/SGG | Ssp I | AAT/ATT |
| Nco I | C/CATGG | Stu I | AGG/CCT |
| Nde I | CA/TATG | Sty I | C/CWWGG |
| Nhe I | G/CTAGC | Swa I | ATTT/AAAT |
| Nla III | CATG/ | Taq I | T/CGA |
| Nla IV | GGN/NCC | Taq II | GACCGA (11/9) |
| Not I | GC/GGCCGC | Tfi I | GAWTC |
| Nru I | TCG/CGA | Tsp45 I | GTSAC |
| Nsi I | ATGCA/T | TspE I | AATT |
| Nsp I | RCATG/Y | Tth111 I | GACN/NNGTC |
| NspB II | CMG/CKG | Tth111 II | CAARCA (11/9) |
| Pac I | TTAAT/TAA | Vsp I | AT/TAAT |
| Pal I | GG/CC | Xba I | T/CTGAGA |
| Pfl1108 I | TCGTAG | Xcm I | CCANNNNN/NNNNTGG |
| PflM I | CCANNNN/NTGG | Xho I | C/TCGAG |
| Ple I | GAGTC (4/5) | Xho II | R/GATCY |
| PmaC I | CAC/GTG | Xma I | C/CCGGG |
| Pme I | GTTT/AAAC | Xma III | C/GGCCG |
| PpuM I | RG/GWCCY | Xmn I | GAANN/NNTTC |
| PshA I | GACNN/NNGTC | | |
| PspA I | C/CCGGG | | |

Each lane of the Southern blot represents DNA isolated from one plant. Through the use of a multiplicity of PAT gene integration events as probes on the same genomic DNA blot, the integration event composition of each plant is determined. Correlations are established between the contributions of particular integration events to increasing the yield of the plant. Only those plants that contain the desired combination of integration events are advanced to maturity and used for pollination. DNA probes corresponding to PAT gene integration events are useful markers during the course of plant breeding to identify and combine particular integration events without having to grow the plants and assay the plants for agronomic performance.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

References

The references listed below are incorporated herein by reference to the extent that they supplement, explain, provide a background for, or teach methodology, techniques and/or compositions employed herein.

Adams et al., PCT Publication WO 91/02071
Armaleo et al., *Current Genetics*, 17:97–103, 1990
Armstrong et al., *Maize Genetics Coop Newsletter*, 65:92–93, 1991
Armstrong & Green, *Planta*, 164:207–214, 1985
Bayer et al., Helvetica Chimica Acta, 55:224–239, 1972
Bradford, *Anal. Biochem.*, 72:248–254, 1976
Casas et al., *Proc. Natl. Acad. Sci USA*, 90:11212–11216, 1993
Chomet et al., *EMBO J*, 6:295–302, 1987
Christou et al., *Plant Physiol*, 87:671–674, 1988
Christou, et al., *Bio/Technology*, 9:957–962, 1991
Chu et al., *Scientia Sinica*, 18:659–668, 1975
Clark, *J. of Plant Nutrition*, 5:1039, 1982
Conger et al., *Plant Cell Rep*, 6:345–347, 1987
De Block et al., *Plant Physiol*, 91:694–701, 1989
De Block et al., *EMBO J.*, 6:2513–2518; 1987
DE 3642 B29 A. (German Patent Application)
D'Halluin et al., *The Plant Cell*, 4:1495–1505, 1992
Dekeyser et al., *Plant Physiol*, 90:217–223, 1989
Demain et al., In: *Biochemistry and Genetic Reaulation of Commercially Important Antibiotics*, Ed.: Vining, L., Addison-Wesley Publishing Co., 1983
European Patent EP 0,242,236
European Patent EP 0,242,246
Feinberg & Vogelstein, *Anal Biochem*, 132:6–13, 1983
Fromm et al., *Nature*, 312:791–793, 1986
Gordon-Kamm et al., *Plant Cell*, 2:603–618, 1990
Gordon-Kamm et al., *Plant Cell*, 2:603–618, 1990
Hallauer et al., In: *Corn and Corn Improvement*, Eds: Sprague & Dudley, Agronomy Society of American Publishing, 1988
Harlow & Lane, *Antibodies: A laboratory manual*, Cold Spring Harbor, 1988
Hauptmann et al., *Plant Physiol*, 86:602–606, 1988
Jefferson, P1 *Mol Biol Repr*, 5:387–405, 1987
Klein et al., *Nature*, 327:70–73, 1987
Klein et al., *Plant Physiol*, 91:440–444, 1989
Koziel et al., *Bio/Technology*, 11:194–200, 1993
Krzyzek & Laursen, PCT Publication WO 92/12250
Krzyzek et al., U.S. patent application Ser. No. 07/635,279, filed Dec. 28, 1990
Laemelli, *Nature*, 227:680–685, 1970
Lande, & Thompson, *Genetics*, 124:743–756, 1990
Laursen et al., *Plant Molecular Biology*, 24:51–61, 1994
Leemans et al., *British Crop Protection Conference—Weeds*, 3:867–870, 1987
Lorz et al., *Mol Gen Genet*, 199:178–182, 1985
Lyznik et al., *Plant Mol Biol*, 13:151–16, 1989
Mizobuchi, & Frohman, *Biotechniques*, 15:215–216, 1993
Murakami et al., *Mol Gen Genet*, 205:42–50, 1986
Murashige & Skoog, *Physiol Plant*, 15:473–497, 1962
Nester et al., *Ann. Rev. Plant Physiol*, 35:387–413, 1984
Ogawa et al., *Sci. Rep., Meija Seika*, 13:42–48, 1973
PCT Patent Application, Publication No. WO 87/00141
PCT Patent Application, Publication No. WO 87/05629, published Sep. 24, 1987, 1987
Potrykus, *Trends Biotechnol*, 7:269–273, 1989
Sambrook et al., *Molecular Cloning, A Laboratory Manual*, 2nd ed. Cold Spring Harbor Laboratory Press, 1989
Shillito et al., *Bio/Technol*, 7:581–587, 1989
Shure et al., *Cell*, 35:225–233, 1983
Southern, *J Mol Biol*, 98:503–517, 1975
Spencer et al., *Theor. Appl. Genet.*, 79:625–631, 1990
Spencer et al., *NATO ASI Series*, Vol H 81 Plant Molecular Biology, pp. 559–565, 1994
Sprague & Eberhart, In: *Corn and Corn Improvement*, 2nd Ed., Eds.: Dudley & Sprague, Iowa State University Press, 1977
Tanksley et al., *Bio/Technology*, 7:257–264, 1989
Thompson et. al., *EMBO J.*, 6:2519–2523, 1987
Thompson et al., *EMBO J*, 6:2519–2623, 1987
Twell et al., *Plant Physiol*, 91:1270–1274, 1989
U.S. Pat. No. 4,732,856.

Wan & Lemaux, *Plant Physiol.*, 104:37–48, 1994
U.S. patent application Ser. No. 07/974,379
U.S. patent application Ser. No. 08/113,561
U.S. patent application Ser. No. 08/233,067
U.S. Pat. No. 5,273,894
U.S. Pat. No. 5,276,268

Wang et al., *Plant Molecular Biology*, 11:433–439, 1988
Weeks et al., *Plant Physiol.*, 102:1077–1084, 1993
White et. al., *Nucl. Acids Res.*, 18:1062, 1990
Yang et al., *Plant Cell Rep*, 7:421–425, 1988
Zhang et al., *Plant Cell Rep*, 7:379–384, 1988

What is claimed is:

1. A fertile transgenic maize plant which incorporates a bar gene encoding phosphinothricin acetyl transferase, wherein the bar gene integration event, designated B16, is present in seed deposited under ATCC designation 203059.
2. The seed of the plant of claim 1.
3. The transformed maize plant of claim 1, wherein the bar gene encoding phosphinothricin acetyl transferase is the bar gene of *Streptomyces hygroscopicus*.
4. An inbred maize plant, the genome of which comprises a bar gene, said bar gene introduced into said inbred maize by backcrossing with a transformant containing the bar gene integration event, designated B16, which is present in seed deposited under ATCC designation 203059.
5. Progeny of the plant of claim 4.
6. The seed of the plant of claim 4.
7. The seed of the plant of claim 6.
8. A hybrid maize plant, the genome of which comprises a bar gene, said hybrid maize plant prepared by crossing a first and second inbred maize plant, wherein one said inbred maize plants comprises a bar gene introduced into said inbred from a transformant containing a bar gene integration event, designated B16, which is present in seed deposited under ATCC designation 203059.
9. Progeny of the plant of claim 8.
10. The seed of the plant of claim 8.
11. The seed of the plant of claim 9.
12. A hybrid maize plant produced by crossing two inbred parents, wherein one of the parents contains an introgressed bar gene integration event, designated B16, which is present in seed deposited under ATCC designation 203059.
13. Progeny of the plant of claim 12.
14. The seed of the plant of claim 12.
15. The seed of the plant of claim 14.
16. A crossed fertile transgenic maize plant comprising DNA encoding phosphinothricin acetyl transferase, said crossed plant being prepared by a process comprising:
    (a) obtaining a fertile transgenic maize plant which comprises a bar gene encoding phosphinothricin acetyl transferase integrated into its chromosomal DNA, wherein the bar gene integration event, designated B16, is present in seed deposited under ATCC designation 203059; and
    (b) crossing said fertile transgenic maize plant with a second maize plant to obtain a crossed transgenic maize plant incorporating DNA encoding phosphinothricin acetyl transferase.
17. A crossed fertile transgenic maize plant comprising DNA encoding phosphinothricin acetyl transferase, said crossed plant being prepared by a process comprising:
    (a) obtaining a fertile transgenic maize plant which comprises a bar gene encoding phosphinothricin acetyl transferase integrated into its chromosomal DNA, wherein the bar gene integration event, designated B16, is present in seed deposited under ATCC designation 203059;
    (b) crossing said fertile transgenic maize plant with a second maize plant to obtain a transgenic maize plant incorporating DNA encoding phosphinothricin acetyl transferase;
    (c) performing at least one backcross of said transgenic maize plant to obtain a backcrossed fertile transgenic maize plant chromosomally incorporating DNA encoding phosphinothricin acetyl transferase.
18. A crossed fertile transgenic maize plant comprising DNA encoding phosphinothricin acetyl transferase, said crossed plant being prepared by a process comprising:
    (a) obtaining a fertile transgenic maize plant which comprises a bar gene encoding phosphinothricin acetyl transferase integrated into its chromosomal DNA, wherein the bar gene integration event, designated B16, is present in seed deposited under ATCC designation 203059; and
    (b) crossing said fertile transgenic maize plant with a second maize plant to obtain a crossed transgenic maize plant incorporating DNA encoding phosphinothricin acetyl transferase; wherein said DNA encoding phosphinothricin acetyl transferase is inherited through a male parent.
19. A crossed fertile transgenic maize plant comprising DNA encoding phosphinothricin acetyl transferase, said crossed plant being prepared by a process comprising:
    (a) obtaining a fertile transgenic maize plant which comprises a bar gene encoding phosphinothricin acetyl transferase integrated into its chromosomal DNA, wherein the bar gene integration event, designated B16, is present in seed deposited under ATCC designation 203059;

(b) crossing said fertile transgenic maize plant with a second maize plant to obtain a transgenic maize plant incorporating DNA encoding phosphinothricin acetyl transferase;

(c) performing at least one Backcross of said transgenic maize plant to obtain a backcrossed fertile transgenic maize plant chromosomally incorporating DNA encoding phosphinothricin acetyl transferase; wherein said DNA encoding phosphinothricin acetyl transferase is inherited through a male parent.

20. A crossed fertile transgenic maize plant comprising DNA encoding, phosphinothricin acetyl transferase, said crossed plant being prepared by a process comprising:

(a) obtaining a fertile transgenic maize plant which comprises a bar gene encoding phosphinothricin acetyl transferase integrated into its chromosomal DNA, wherein the bar gene integration event, designated B16, is present in seed deposited under ATCC designation 203059; and (b) crossing said fertile transgenic maize plant with a second maize plant to obtain a crossed transgenic maize plant incorporating DNA encoding phosphinothricin acetyl transferase; wherein said DNA encoding phosphinothricin acetyl transferase is inherited through a female parent.

21. A crossed fertile transgenic maize plant comprising DNA encoding phosphinothricin acetyl transferase, said crossed plant being prepared by a process comprising:

(a) obtaining a fertile transgenic maize plant which comprises a bar gene encoding phosphinothricin acetyl transferase integrated into its chromosomal DNA, wherein the bar gene integration event, designated B16, is present in seed deposited under ATCC designation 203059;

(b) crossing said fertile transgenic maize plant with a second maize plant to obtain a transgenic maize plant incorporating DNA encoding phosphinothricin acetyl transferase;

(c) performing at least one backcross of said transgenic maize plant to obtain a backcrossed fertile transgenic maize plant chromosomally incorporating DNA encoding phosphinothricin acetyl transferase;

wherein said DNA encoding phosphinothricin acetyl transferase is inherited through a female parent.

22. The fertile transgenic maize plant of claim 16, 17, 18, 19, 20, or 21, wherein said second maize plant lacks DNA encoding phosphinothricin acetyl transferase.

23. The fertile transgenic maize plant of claim 16, 17, 18, 19, 20, or 21, wherein said second maize plant is non-transgenic.

24. The fertile transgenic maize plant of claim 16, 17, 18, 19, 20, or 21, wherein said second maize plant is transgenic.

25. The fertile transgenic maize plant of claim 16, 17, 18, 19, 20, or 21, wherein said second maize plant is an inbred.

26. The fertile transgenic maize plant of claim 16, 17, 18, 19, 20, or 21, wherein said crossed maize plant is a hybrid.

27. The fertile transgenic maize plant of claim 16, 17, 18, 19, 20, or 21, wherein said crossed fertile transgenic maize plant comprising a bar gene integrated into its chromosomal DNA contains a bar gene integration event, designated B 16, wherein said integration event is present in seed deposited under the ATCC designation 203059.

28. A crossed fertile transgenic maize plant comprising DNA encoding phosphinothricin acetyl transferase, said crossed plant being prepared by a process comprising:

(a) obtaining a fertile transgenic maize plant which comprises a bar gene encoding phosphinothricin acetyl transferase, wherein the bar gene integration event, designated B16, is present in seed deposited under ATCC designation 203059;

(b) crossing said fertile transgenic maize plant with a second maize plant to obtain a third transgenic maize plant incorporating DNA encoding phosphinothricin acetyl transferase; and (c) crossing said third fertile transgenic maize plant with a fourth maize plant to obtain a fifth transgenic maize plant incorporating DNA encoding phosphinothricin acetyl transferase.

29. The maize plant of claim 28, wherein said second and fourth maize plants have the same genotype.

30. The maize plant of claim 28, wherein said second and fourth maize plants have different genotypes.

31. Seed of a fertile, transgenic maize plant, said seed comprising DNA encoding phosphinothricin acetyl transferase and capable of being cultivated to produce a transgenic maize plant having resistance to a herbicide comprising phosphinothricin, said seed prepared by a process comprising the steps of:

(a) obtaining a fertile transgenic maize plant which comprises a bar gene encoding phosphinothricin acetyl transferase, wherein the bar gene integration event, designated B16, is present in seed deposited under ATCC designation 203059;

(b) breeding said parental plant with a second fertile maize plant to produce a plurality of progeny fertile, transgenic maize plants, said progeny maize plants including plants that express DNA encoding phosphinothricin acetyl transferase;

(c) selecting from progeny maize plants a plant having resistance to a herbicide comprising phosphinothricin; and (d) obtaining seed from said selected progeny maize plant.

32. The seed of claim 31, wherein the progeny maize plants are two generations removed from the parental transgenic maize plant.

33. The seed of claim 31, wherein the progeny maize plants having resistance to a herbicide comprising phosphinothricin are selected by testing plants for resistance to said herbicide.

34. The seed of claim 31, wherein said second fertile maize plant is a non-transgenic maize plant.

35. The seed of claim 31, wherein said second fertile maize plant is pollinated with pollen from a male parental transgenic maize plant.

36. The seed of claim 31, wherein said parental maize plant is pollinated with pollen from said second fertile maize plant and wherein said maize plant is a female parental transgenic maize plant.

37. The seed of claim 31, wherein the progeny maize plants having resistance to a herbicide comprising phosphinothricin are selected by hybridization with a $^{32}$P-labeled bar gene sequence probe.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 807 base pairs
      (B) TYPE: nucleic acid
      (C) STRANDEDNESS: single
      (D) TOPOLOGY: linear (xi) SEQUENCE DESCRIPTION: SEQ ID NO:1:

```
AGATCTGGAG CGACGTCCTG GGGGCCGGTC CGGTGCTGCC CGGGGACGAC TTCTTCTCCC      60

TCGGCGGCAC CTCCATCTCG GCGTTGCGGG TGGTCTCGCG CATCCGCAAG GAACTCGGCG     120

TGCCACTCCG GCTCGCCGTG ATCTTCGAGA CGCCGTCCCT GGAAGCGGTG GCCGAATCCG     180

TACTCCGCGA ACTGAAGGGG ACGTAGTAAA GAGGTGCCCG CCACCCGCTT TCGCAGAACA     240

CCGAAGGAAG ACCACACGTG AGCCCAGAAC GACGCCCGGT CGAGATCCGT CCCGCCACCG     300

CCGCCGACAT GGCGGCGGTC TGCGACATCG TCAATCACTA CATCGAGACG AGCACGGTCA     360

ACTTCCGTAC GGAGCCGCAG ACTCCGCAGG AGTGGATCGA CGACCTGGAG CGCCTCCAGG     420

ACCGCTACCC CTGGCTCGTC GCCGAGGTGG AGGGCGTCGT CGCCGGCATC GCCTACGCCG     480

GCCCCTGGAA GGCCCGCAAC GCCTACGACT GGACCGTCGA GTCGACGGTG TACGTCTCCC     540

ACCGGCACCA GCGGCTCGGA CTGGGCTCCA CCCTCTACAC CCACCTGCTG AAGTCCATGG     600

AGGCCCAGGG CTTCAAGAGC GTGGTCGCCG TCATCGGACT GCCCAACGAC CCGAGCGTGC     660

GCCTGCACGA GGCGCTCGGA TACACCGCGC GCGGGACGCT GCGGGCAGCC GGCTACAAGC     720

ACGGGGGCTG GCACGACGTG GGGTTCTGGC AGCGCGACTT CGAGCTGCCG GCCCCGCCCC     780

GCCCCGTCCG GCCCGTCACA CAGATCT                                        807
```

(2) INFORMATION FOR SEQ ID NO:2:

(i) SEQUENCE CHARACTERISTICS:
      (A) LENGTH: 183 amino acids
      (B) TYPE: amino acid
      (C) STRANDEDNESS: single
      (D) TOPOLOGY: linear (xi) SEQUENCE DESCRIPTION: SEQ ID NO:2:

```
Met Ser Pro Glu Arg Arg Pro Val Glu Ile Arg Pro Ala Thr Ala Ala
1               5                   10                  15

Asp Met Ala Ala Val Cys Asp Ile Val Asn His Tyr Ile Glu Thr Ser
            20                  25                  30

Thr Val Asn Phe Arg Thr Glu Pro Gln Thr Pro Gln Glu Trp Ile Asp
        35                  40                  45

Asp Leu Glu Arg Leu Gln Asp Arg Tyr Pro Trp Leu Val Ala Glu Val
    50                  55                  60
```

```
Glu Gly Val Val Ala Gly Ile Ala Tyr Ala Gly Pro Trp Lys Ala Arg
 65                  70                  75                  80

Asn Ala Tyr Asp Trp Thr Val Glu Ser Thr Val Tyr Val Ser His Arg
                 85                  90                  95

His Gln Arg Leu Gly Leu Gly Ser Thr Leu Tyr Thr His Leu Leu Lys
            100                 105                 110

Ser Met Glu Ala Gln Gly Phe Lys Ser Val Val Ala Val Ile Gly Leu
        115                 120                 125

Pro Asn Asp Pro Ser Val Arg Leu His Glu Ala Leu Gly Tyr Thr Ala
    130                 135                 140

Arg Gly Thr Leu Arg Ala Ala Gly Tyr Lys His Gly Gly Trp His Asp
145                 150                 155                 160

Val Gly Phe Trp Gln Arg Asp Phe Glu Leu Pro Ala Pro Pro Arg Pro
                165                 170                 175

Val Arg Pro Val Thr Gln Ile
            180
```

(2) INFORMATION FOR SEQ ID NO:3:

(i) SEQUENCE CHARACTERISTICS:
  (A) LENGTH: 615 base pairs
  (B) TYPE: nucleic acid
  (C) STRANDEDNESS: single
  (D) TOPOLOGY: linear (xi) SEQUENCE DESCRIPTION: SEQ ID NO:3:

```
GAATTCGAGC TCGGTACCCG GGGATCTACC ATGAGCCCAG AACGACGCCC GGCCGACATC    60

CGCCGTGCCA CCGAGGCGGA CATGCCGGCG GTCTGCACCA TCGTCAACCA CTACATCGAG   120

ACAAGCACGG TCAACTTCCG TACCGAGCCG CAGGAACCGC AGGAGTGGAC GGACGACCTC   180

GTCCGTCTGC GGGAGCGCTA TCCCTGGCTC GTCGCCGAGG TGGACGGCGA GGTCGCCGGC   240

ATCGCCTACG CGGGCCCCTG GAAGGCACGC AACGCCTACG ACTGGACGGC CGAGTCGACC   300

GTGTACGTCT CCCCCCGCCA CCAGCGGACG GGACTGGGCT CCACGCTCTA CACCCACCTG   360

CTGAAGTCCC TGGAGGCACA GGGCTTCAAG AGCGTGGTCG CTGTCATCGG GCTGCCCAAC   420

GACCCGAGCG TGCGCATGCA CGAGGCGCTC GGATATGCCC CCGCGGCAT GCTGCGGGCG    480

GCCGGCTTCA AGCACGGGAA CTGGCATGAC GTGGGTTTCT GGCAGCTGGA CTTCAGCCTG   540

CCGGTACCGC CCCGTCCGGT CCTGCCCGTC ACCGAGATCT GATGACCCGG GGGATCCCTG   600

CAGGCATGCA AGCTT                                                   615
```

(2) INFORMATION FOR SEQ ID NO:4:

(i) SEQUENCE CHARACTERISTICS:
  (A) LENGTH: 183 amino acids
  (B) TYPE: amino acid
  (C) STRANDEDNESS: single
  (D) TOPOLOGY: linear (xi) SEQUENCE DESCRIPTION: SEQ ID NO:4:

```
Met Ser Pro Glu Arg Arg Pro Ala Asp Ile Arg Arg Ala Thr Glu Ala
  1               5                  10                  15

Asp Met Pro Ala Val Cys Thr Ile Val Asn His Tyr Ile Glu Thr Ser
             20                  25                  30

Thr Val Asn Phe Arg Thr Glu Pro Gln Glu Pro Gln Glu Trp Thr Asp
             35                  40                  45

Asp Leu Val Arg Leu Arg Glu Arg Tyr Pro Trp Leu Val Ala Glu Val
 50                  55                  60
```

-continued

```
Asp Gly Glu Val Ala Gly Ile Ala Tyr Ala Gly Pro Trp Lys Ala Arg
65                  70                  75                  80

Asn Ala Tyr Asp Trp Thr Ala Glu Ser Thr Val Tyr Val Ser Pro Arg
                85                  90                  95

His Gln Arg Thr Gly Leu Gly Ser Thr Leu Tyr Thr His Leu Leu Lys
            100                 105                 110

Ser Leu Glu Ala Gln Gly Phe Lys Ser Val Val Ala Val Ile Gly Leu
        115                 120                 125

Pro Asn Asp Pro Ser Val Arg Met His Glu Ala Leu Gly Tyr Ala Pro
        130                 135                 140

Arg Gly Met Leu Arg Ala Ala Gly Phe Lys His Gly Asn Trp His Asp
145                 150                 155                 160

Val Gly Phe Trp Gln Leu Asp Phe Ser Leu Pro Val Pro Pro Arg Pro
                165                 170                 175

Val Leu Pro Val Thr Glu Ile
                180
```